US008415148B2

(12) United States Patent
Perrault

(10) Patent No.: US 8,415,148 B2
(45) Date of Patent: Apr. 9, 2013

(54) EXPRESSION SYSTEM

(75) Inventor: Jacques Perrault, Poway, CA (US)

(73) Assignee: San Diego State University Foundation, San Diego, CA (US)

( * ) Notice: Subject to any disclaimer, the term of this patent is extended or adjusted under 35 U.S.C. 154(b) by 0 days.

(21) Appl. No.: 13/196,376

(22) Filed: Aug. 2, 2011

(65) Prior Publication Data

US 2011/0294204 A1 Dec. 1, 2011

Related U.S. Application Data

(62) Division of application No. 11/628,374, filed as application No. PCT/US2005/019371 on Jun. 1, 2005, now Pat. No. 8,012, 747.

(60) Provisional application No. 60/576,169, filed on Jun. 1, 2004.

(51) Int. Cl.
*C12N 15/63* (2006.01)
*C07H 21/04* (2006.01)

(52) U.S. Cl.
USPC ...................................... 435/320.1; 536/24.1

(58) Field of Classification Search ........................ None
See application file for complete search history.

(56) References Cited

U.S. PATENT DOCUMENTS

| | | | |
|---|---|---|---|
| 6,168,943 | B1 | 1/2001 | Rose |
| 2003/0039955 | A1 | 2/2003 | Feng et al. |
| 2003/0044386 | A1 | 3/2003 | Barber |
| 2003/0091592 | A1 | 5/2003 | Barber |

FOREIGN PATENT DOCUMENTS

| | | |
|---|---|---|
| WO | WO 95/10608 | 4/1995 |
| WO | WO 96/34625 | 11/1996 |
| WO | WO 01/19380 | 3/2001 |

OTHER PUBLICATIONS

Whelan et al. Efficient recovery of infectious vesicular stomatitis virus entirely from cDNA clones. Proc Natl Acad Sci U S A. Aug. 29, 1995;92(18):8388-92.*

Cogoni et al., "Suppression of gene expression by homologous transgenes," *Antonie Van Leeuwenhoek*, 1994, 65:205-209.

Cohen et al. "Nonchromosomal antibiotic resistance in bacteria: genetic transformation of *Escherichia coli* by R-factor DNA," *Proc. Natl. Acad. Sci. USA*, 1972, 69:2110-2114.

Eckert et al., "Vaccinia virus-bacteriophage T7 expression vector for complementation analysis of late gene processes," *J Gen Virol.*, 1999, 80(Pt 6):1463-1469.

Elbashir et al., "Duplexes of 21-nucleotide RNAs mediate RNA interference in cultured mammalian cells," *Nature*, 2001, 411:494-498.

Elbashir et al., "RNA interference is mediated by 21- and 22-nucleotide RNAs," *Genes Devel.*, 2001, 15:188-200.

*Fields Virology*, third edition, 1995, ed. B. N. Fields, vol. 1, pp. 1121-1159.

Fuerst et al., "Eukaryotic transient-expression system based on recombinant vaccinia virus that synthesizes bacteriophage T7 RNA polymerase," *Proc. Natl. Acad. Sci. USA*, 1986, 83:8122-8126.

*Fundamental Virology*, second edition, 1991, ed. B. N. Fields, Raven Press, New York, pp. 489-503.

Gallione et al., "Nucleotide sequences of the mRNA's encoding the vesicular stomatitis virus N and NS proteins," *J. Virol.*, 1981, 39: 529-535.

Goeddel et al., "Synthesis of human fibroblast interferon by *E. coli*," *Nucleic Acids Res.*, 1980, 8:4057-4074.

Hellen et al., "Internal ribosome entry sites in eukaryotic mRNA molecules," *Genes Dev.*, 2001, 15(13):1593-1612.

Kennerdell and Carthew, "Use of dsRNA-mediated genetic interference to demonstrate that frizzled and frizzled act in the wingless pathway," *Cell*, 1998, 95:1017-1026.

Latimer et al., "Specificity of monoclonal antibodies produced against phosphorothioate and ribo modified DNAs," *Mol. Immunol.*, 1995, 32:1057-1064.

Lawn et al., "The sequence of human serum albumin cDNA and its expression in *E. coli*," *Nucleic Acids Res.*, 1981, 9:6103-6114.

Mohamed et al., "Transient and inducible expression of vaccinia/T7 recombinant viruses," *Methods Mol. Biol.*, 2004, 269:41-50.

Peyrottes et al., "Oligodeoxynucleoside phosphoramidates (P-NH2): synthesis and thermal stability of duplexes with DNA and RNA targets," *Nucleic Acids Res.* 1996, 24:1841-1848.

Rose and Gallione, "Nucleotide sequences of the mRNA's encoding the vesicular stomatitis virus G and M proteins determined from cDNA clones containing the complete coding regions," *J. Virol.*, 1981, 39:519-528.

Rose and Schubert, "Rhabdovirus genomes and their products," in *The Viruses: The Rhabdoviruses*, 1987, Wagner (ed.), Plenum Publishing Corp., NY, pp. 129-166, 1987.

Rose et al., "A new cationic liposome reagent mediating nearly quantitative transfection of animal cells," *Biotechniques*, 1991, 10:520-525.

Schubert et al., "Expression of a cDNA encoding a functional 241-kilodalton vesicular stomatitis virus RNA polymerase," *Proc. Natl. Acad. Sci. USA*, 1985, 82:7984-7988.

Schultz et al., "Oligo-2'-fluoro-2'-deoxynucleotide N3'—>P5' phosphoramidates: synthesis and properties," *Nucleic Acids Res.*, 1996, 24:2966-2973.

Svoboda et al., "Selective reduction of dormant maternal mRNAs in mouse oocytes by RNA interference," *Development*, 2000, 127:4147-4156.

Timmons and Fire, "Specific interference by ingested dsRNA," *Nature*, 1998, 395:854.

Waterhouse et al., "Virus resistance and gene silencing in plants is induced by double-stranded RNA," *Proc. Natl. Acad. Sci. USA*, 1998, 95:13959.

Whelan, et al., "Efficient recovery of infectious vesicular stomatitis virus entirely from cDNA clones," *Proc. Natl. Acad. Sci. USA*, 1995, 92:8388-8392.

Wianny and Zernicka-Goetz, "Specific interference with gene function by double-stranded RNA in early mouse development," *Nat. Cell Biol.*, 2000, 2:70-75.

Wigler et al., "DNA-mediated transfer of the adenine phosphoribosyltransferase locus into mammalian cells," *Proc. Natl. Acad. Sci. USA*, 1979, 76:1373-1376.

(Continued)

*Primary Examiner* — Michele K Joike
(74) *Attorney, Agent, or Firm* — Fish & Richardson P.C.

(57) ABSTRACT

The present invention relates generally to methods and compositions for expression of polypeptides or delivery of interfering RNAs in various cell types.

9 Claims, 18 Drawing Sheets

OTHER PUBLICATIONS

Yang et al., "Specific Double-Stranded RNA Interference in Undifferentiated Mouse Embryonic Stem Cells," *Mol. Cell Biol.*, 2001, 21:7807-7816.

Authorized Officer David Guzo, International Search Report and Written Opinion of the International Searching Authority in PCT/US05/19371, mailed Aug. 29, 2006, 5 pages.

Authorized Officer Ellen Moyse, International Preliminary Report on Patentability in PCT/US05/19371, issued Dec. 4, 2006, 4 pages.

ATCC Acession No. VR-159, 2 pages, 2011.

Genbank Accession No. J02428, dated Oct. 21, 2002, 4 pages.

Balachandran and Barber, "Vesicular stomatitis virus (VSV) therapy of tumors," *IUBMB Life*, 2000, 50:135-138.

Baltimore et al., "Ribonucleic acid synthesis of vesicular stomatitis virus, II. An RNA polymerase in the virion," *Proc. Natl. Acad. Sci. USA*, 1970, 66:572-576.

Bass, "RNA interference: The short answer," *Nature*, 2001, 411:428-429.

Baulcombe, "RNA as a target and an initiator of post-transcriptional gene silencing in transgenic plants," *Plant Mol. Biol.*, 1996, 32:79-88.

Braun et al., "Immunogenic duplex nucleic acids are nuclease resistant," *J. Immunol.*, 1988, 141:2084-2089.

Britton et al., "Expression of bacteriophage T7 RNA polymerase in avian and mammalian cells by recombinant fowlpox virus," *J. Gen Virol.*, 1996, 77:963-7.

Caplan et al., "Specific inhibition of gene expression by small double-stranded RNAs in invertebrate and vertebrate systems," *Proc. Natl. Acad. Sci. USA*, 2001, 98:9742.

Chaturvedi et al. "Stabilization of triple-stranded oligonucleotide complexes: use of probes containing alternating phosphodiester and stereo-uniform cationic phosphoramidate linkages," *NucleicAcids Res.*, 1996, 24: 2318-2323.

Chen et al., "A self-initiating eukaryotic transient gene expression system based on contransfection of bacteriophage T7 RNA polymerase and DNA vectors containing a T7 autogene," *Nucleic Acids Res.*, 1994, 22(11):2114-2120.

* cited by examiner

Vaccinia-T7 System and pTM1-GFP Plasmid (IRES)

Vaccinia-T7 System and pSP73-GFP Plasmid (no IRES)

VSV-T7 System Expression Compared to Vaccinia-T7

VSV-T7 System with Vaccinia Capping Enzyme
(pSP73-GFP, pTM1-D1, pTM1-D12)

SEQUENCE LISTING

```
<160> NUMBER OF SEQ ID NOS: 6

<210> SEQ ID NO 1
<211> LENGTH: 17304
<212> TYPE: DNA
<213> ORGANISM: Artificial Sequence
<220> FEATURE:
<223> OTHER INFORMATION: pVSV-T7

<400> SEQUENCE: 1

cacctaaatt gtaagcgtta atattttgtt aaaattcgcg ttaaattttt gttaaatcag     60

ctcatttttt aaccaatagg ccgaaatcgg caaaatccct tataaatcaa aagaatagac    120

cgagataggg ttgagtgttg ttccagtttg gaacaagagt ccactattaa agaacgtgga    180

ctccaacgtc aaagggcgaa aaaccgtcta tcagggcgat ggcccactac gtgaaccatc    240

accctaatca agttttttgg ggtcgaggtg ccgtaaagca ctaaatcgga accctaaagg    300

gagcccccga tttagagctt gacggggaaa gccggcgaac gtggcgagaa aggaagggaa    360

gaaagcgaaa ggagcgggcg ctagggcgct ggcaagtgta gcggtcacgc tgcgcgtaac    420

caccacaccc gccgcgctta atgcgccgct acagggcgcg tcccattcgc cattcaggct    480

gcgcaactgt tgggaagggc gatcggtgcg ggcctcttcg ctattacgcc agctggcgaa    540

agggggatgt gctgcaaggc gattaagttg ggtaacgcca gggttttccc agtcacgacg    600

ttgtaaaacg acggccagtg aattgtaata cgactcacta tagggcgaat tgggtaccgg    660

gccccccctc gagttgtaat acgactcact atagggacga agacaaacaa accattatta    720

tcattaaaag gctcaggaga aactttaaca gtaatcaaaa tgtctgttac agtcaagaga    780

atcattgaca acacagtcat agttccaaaa cttcctgcaa atgaggatcc agtggaatac    840

ccggcagatt acttcagaaa atcaaaggag attcctcttt acatcaatac tacaaaaagt    900

ttgtcagatc taagaggata tgtctaccaa ggcctcaaat ccggaaatgt atcaatcata    960

catgtcaaca gctacttgta tggagcatta aaggacatcc ggggtaagtt ggataaagat   1020

tggtcaagtt tcggaataaa catcgggaaa gcaggggata caatcggaat atttgacctt   1080

gtatccttga aagccctgga cggcgtactt ccagatggag tatcggatgc ttccagaacc   1140

agcgcagatg acaaatggtt gcctttgtat ctacttggct tatacagagt gggcagaaca   1200

caaatgcctg aatacagaaa aaagctcatg gatgggctga caaatcaatg caaaatgatc   1260

aatgaacagt ttgaacctct tgtgccagaa ggtcgtgaca tttttgatgt gtggggaaat   1320

gacagtaatt acacaaaaat tgtcgctgca gtggacatgt tcttccacat gttcaaaaaa   1380
```

-continued

```
catgaatgtg cctcgttcag atacggaact attgtttcca gattcaaaga ttgtgctgca   1440
ttggcaacat ttggacacct ctgcaaaata accggaatgt ctacagaaga tgtaacgacc   1500
tggatcttga accgagaagt tgcagatgaa atggtccaaa tgatgcttcc aggccaagaa   1560
attgacaagg ccgattcata catgccttat ttgatcgact ttggattgtc ttctaagtct   1620
ccatattctt ccgtcaaaaa ccctgccttc cacttctggg ggcaattgac agctcttctg   1680
ctcagatcca ccagagcaag gaatgcccga cagcctgatg acattgagta tacatctctt   1740
actacagcag gtttgttgta cgcttatgca gtaggatcct ctgccgactt ggcacaacag   1800
ttttgtgttg gagataacaa atacactcca gatgatagta ccggaggatt gacgactaat   1860
gcaccgccac aaggcagaga tgtggtcgaa tggctcggat ggtttgaaga tcaaaacaga   1920
aaaccgactc ctgatatgat gcagtatgcg aaaagagcag tcatgtcact gcaaggccta   1980
agagagaaga caattggcaa gtatgctaag tcagaatttg acaaatgacc ctataattct   2040
cagatcacct attatatatt atgctacata tgaaaaaaac taacagatat catggataat   2100
ctcacaaaag ttcgtgagta tctcaagtcc tattctcgtc tggatcaggc ggtaggagag   2160
atagatgaga tcgaagcaca acgagctgaa aagtccaatt atgagttgtt ccaagaggat   2220
ggagtggaag agcatactaa gccctcttat tttcaggcag cagatgattc tgacacagaa   2280
tctgaaccag aaattgaaga caatcaaggt ttgtatgcac cagatccaga agctgagcaa   2340
gttgaaggct ttatacaggg gcctttagat gactatgcag atgaggaagt ggatgttgta   2400
tttacttcgg actggaaaca gcctgagctt gaatctgacg agcatggaaa gaccttacgg   2460
ttgacatcgc cagagggttt aagtggagag cagaaatccc agtggctttc gacgattaaa   2520
gcagtcgtgc aaagtgccaa atactggaat ctggcagagt gcacatttga agcatcggga   2580
gaaggggtca ttatgaagga gcgccagata actccggatg tatataaggt cactccagtg   2640
atgaacacac atccgtccca atcagaagca gtatcagatg tttggtctct ctcaaagaca   2700
tccatgactt tccaacccaa gaaagcaagt cttcagcctc tcaccatatc cttggatgaa   2760
ttgttctcat ctagaggaga gttcatctct gtcggaggtg acggacgaat gtctcataaa   2820
gaggccatcc tgctcggcct gagatacaaa aagttgtaca atcaggcgag agtcaaatat   2880
tctctgtaga ctatgaaaaa aagtaacaga tatcacgatc taagtgttat cccaatccat   2940
tcatcatgag ttccttaaag aagattctcg gtctgaaggg gaaaggtaag aaatctaaga   3000
aattagggat cgcaccaccc ccttatgaag aggacactag catggagtat gctccgagcg   3060
ctccaattga caaatcctat tttggagttg acgagatgga cacctatgat ccgaatcaat   3120
taagatatga gaaattcttc tttacagtga aaatgacggt tagatctaat cgtccgttca   3180
gaacatactc agatgtggca gccgctgtat cccattggga tcacatgtac atcggaatgg   3240
cagggaaacg tcccttctac aaaatcttgg ctttttttggg ttcttctaat ctaaaggcca   3300
ctccagcggt attggcagat caaggtcaac cagagtatca cactcactgc gaaggcaggg   3360
cttatttgcc acataggatg gggaagaccc ctcccatgct caatgtacca gagcacttca   3420
gaagaccatt caatataggt ctttacaagg gaacgattga gctcacaatg accatctacg   3480
atgatgagtc actggaagca gctcctatga tctgggatca tttcaattct tccaaatttt   3540
ctgatttcag agagaaggcc ttaatgtttg gcctgattgt cgagaaaaag gcatctggag   3600
cgtgggtcct ggattctatc agccacttca aatgagctag tctaacttct agcttctgaa   3660
caatccccgg tttactcagt ctctcctaat tccagcctct cgaacaacta atatcctgtc   3720
ttttctatcc ctatgaaaaa aactaacaga gatcgatccc gggaccatgg aacaccctag   3780
```

-continued

```
gcttttgcaa aaagctttgc aaagatggat aaagcggaat tctctgacat cgaactggct   3840
gctatcccgt tcaacactct ggctgaccat tacggtgagc gtttagctcg cgaacagttg   3900
gcccttgagc atgagtctta cgagatgggt gaagcacgct tccgcaagat gtttgagcgt   3960
caacttaaag ctggtgaggt tgcggataac gctgccgcca agcctctcat cactacccta   4020
ctccctaaga tgattgcacg catcaacgac tggtttgagg aagtgaaagc taagcgcggc   4080
aagcgcccga cagccttcca gttcctgcaa gaaatcaagc cggaagccgt agcgtacatc   4140
accattaaga ccactctggc ttgcctaacc agtgctgaca atacaaccgt tcaggctgta   4200
gcaagcgcaa tcggtcgggc cattgaggac gaggctcgct tcggtcgtat ccgtgacctt   4260
gaagctaagc acttcaagaa aaacgttgag gaacaactca acaagcgcgt agggcacgtc   4320
tacaagaaag catttatgca agttgtcgag gctgacatgc tctctaaggg tctactcggt   4380
ggcgaggcgt ggtcttcgtg gcataaggaa gactctattc atgtaggagt acgctgcatc   4440
gagatgctca ttgagtcaac cggaatggtt agcttacacc gccaaaatgc tggcgtagta   4500
ggtcaagact ctgagactat cgaactcgca cctgaatacg ctgaggctat cgcaacccgt   4560
gcaggtgcgc tggctggcat ctctccgatg ttccaacctt gcgtagttcc tcctaagccg   4620
tggactggca ttactggtgg tggctattgg gctaacggtc gtcgtcctct ggcgctggtg   4680
cgtactcaca gtaagaaagc actgatgcgc tacgaagacg tttacatgcc tgaggtgtac   4740
aaagcgatta acattgcgca aaacaccgca tggaaaatca acaagaaagt cctagcggtc   4800
gccaacgtaa tcaccaagtg gaagcattgt ccggtcgagg acatccctgc gattgagcgt   4860
gaagaactcc cgatgaaacc ggaagacatc gacatgaatc ctgaggctct caccgcgtgg   4920
aaacgtgctg ccgctgctgt gtaccgcaag gacaaggctc gcaagtctcg ccgtatcagc   4980
cttgagttca tgcttgagca agccaataag tttgctaacc ataaggccat ctggttccct   5040
tacaacatgg actggcgcgg tcgtgtttac gctgtgtcaa tgttcaaccc gcaaggtaac   5100
gatatgacca aaggactgct tacgctggcg aaaggtaaac caatcggtaa ggaaggttac   5160
tactggctga aaatccacgg tgcaaactgt gcgggtgtcg ataaggttcc gttccctgag   5220
cgcatcaagt tcattgagga aaaccacgag aacatcatgg cttgcgctaa gtctccactg   5280
gagaacactt ggtgggctga gcaagattct ccgttctgct tccttgcgtt ctgctttgag   5340
tacgctgggg tacagcacca cggcctgagc tataactgct cccttccgct ggcgtttgac   5400
gggtcttgct ctggcatcca gcacttctcc gcgatgctcc gagatgaggt aggtggtcgc   5460
gcggttaact tgcttcctag tgaaaccgtt caggacatct acgggattgt tgctaagaaa   5520
gtcaacgaga ttctacaagc agacgcaatc aatgggaccg ataacgaagt agttaccgtg   5580
accgatgaga acactggtga aatctctgag aaagtcaagc tgggcactaa ggcactggct   5640
ggtcaatggc tggcttacgg tgttactcgc agtgtgacta agcgttcagt catgacgctg   5700
gcttacgggt ccaaagagtt cggcttccgt caacaagtgc tggaagatac cattcagcca   5760
gctattgatt ccggcaaggg tctgatgttc actcagccga atcaggctgc tggatacatg   5820
gctaagctga tttgggaatc tgtgagcgtg acggtggtag ctgcggttga agcaatgaac   5880
tggcttaagt ctgctgctaa gctgctggct gctgaggtca aagataagaa gactggagag   5940
attcttcgca agcgttgcgc tgtgcattgg gtaactcctg atggtttccc tgtgtggcag   6000
gaatacaaga agcctattca gacgcgcttg aacctgatgt tcctcggtca gttccgctta   6060
cagcctacca ttaacaccaa caaagatagc gagattgatg cacacaaaca ggagtctggt   6120
atcgctccta actttgtaca cagccaagac ggtagccacc ttcgtaagac tgtagtgtgg   6180
```

-continued

```
gcacacgaga agtacggaat cgaatctttt gcactgattc acgactcctt cggtaccatt   6240

ccggctgacg ctgcgaacct gttcaaagca gtgcgcgaaa ctatggttga cacatatgag   6300

tcttgtgatg tactggctga tttctacgac cagttcgctg accagttgca cgagtctcaa   6360

ttggacaaaa tgccagcact tccggctaaa ggtaacttga acctccgtga catcttagag   6420

tcggacttcg cgttcgcgta acgccaaatc aatacgactc cggatctcga acttgtttat   6480

tgcagcttat aatggttaca aataaagcaa tagcatcaca aatttcacaa ataaagcatt   6540

tttttcactg cattctagtt gtggtttgtc caaactcatc aatgtatctt atcatgtctg   6600

gatcctctac gccggacgca tcgtggccgg catcaccggc gccacaggtg cggttgctgg   6660

cgcctatatc gccgacatca ccgatgggga agatcgggct cgccacttcg ggctcatgag   6720

cgtgtatgaa aaaaactaac agagatcgat ctgtttacgc gtcactatga agtgcctttt   6780

gtacttagcc tttttattca ttggggtgaa ttgcaagttc accatagttt ttccacacaa   6840

ccaaaaagga aactggaaaa atgttccttc taattaccat tattgcccgt caagctcaga   6900

tttaaattgg cataatgact taataggcac agccatacaa gtcaaaatgc ccaagagtca   6960

caaggctatt caagcagacg gttggatgtg tcatgcttcc aaatgggtca ctacttgtga   7020

tttccgctgg tatggaccga agtatataac acagtccatc cgatccttca ctccatctgt   7080

agaacaatgc aaggaaagca ttgaacaaac gaaacaagga acttggctga atccaggctt   7140

ccctcctcaa agttgtggat atgcaactgt gacggatgcc gaagcagtga ttgtccaggt   7200

gactcctcac catgtgctgg ttgatgaata cacaggagaa tgggttgatt cacagttcat   7260

caacggaaaa tgcagcaatt acatatgccc cactgtccat aactctacaa cctggcattc   7320

tgactataag gtcaaagggc tatgtgattc taacctcatt tccatggaca tcaccttctt   7380

ctcagaggac ggagagctat catccctggg aaaggagggc acagggttca gaagtaacta   7440

ctttgcttat gaaactggag gcaaggcctg caaaatgcaa tactgcaagc attggggagt   7500

cagactccca tcaggtgtct ggttcgagat ggctgataag gatctctttg ctgcagccag   7560

attccctgaa tgcccagaag ggtcaagtat ctctgctcca tctcagacct cagtggatgt   7620

aagtctaatt caggacgttg agaggatctt ggattattcc ctctgccaag aaacctggag   7680

caaaatcaga gcgggtcttc caatctctcc agtggatctc agctatcttg ctcctaaaaa   7740

cccaggaacc ggtcctgctt tcaccataat caatggtacc ctaaaatact ttgagaccag   7800

atacatcaga gtcgatattg ctgctccaat cctctcaaga atggtcggaa tgatcagtgg   7860

aactaccaca gaaagggaac tgtgggatga ctgggcacca tatgaagacg tggaaattgg   7920

acccaatgga gttctgagga ccagttcagg atataagttt cctttataca tgattggaca   7980

tggtatgttg gactccgatc ttcatcttag ctcaaaggct caggtgttcg aacatcctca   8040

cattcaagac gctgcttcgc aacttcctga tgatgagagt ttattttttg gtgatactgg   8100

gctatccaaa aatccaatcg agcttgtaga aggttggttc agtagttgga aaagctctat   8160

tgcctctttt ttctttatca tagggttaat cattggacta ttcttggttc tccgagttgg   8220

tatccatctt tgcattaaat taaagcacac caagaaaaga cagatttata cagacataga   8280

gatgaaccga cttggaaagt aactcaaatc ctgctagcca gattcttcat gtttggacca   8340

aatcaacttg tgataccatg ctcaaagagg cctcaattat atttgagttt ttaattttta   8400

tgaaaaaaac taacagcaat catggaagtc cacgattttg agaccgacga gttcaatgat   8460

ttcaatgaag atgactatgc cacaagagaa ttcctgaatc ccgatgagcg catgacgtac   8520

ttgaatcatg ctgattacaa tttgaattct cctctaatta gtgatgatat tgacaatttg   8580
```

-continued

```
atcaggaaat tcaattctct tccgattccc tcgatgtggg atagtaagaa ctgggatgga   8640
gttcttgaga tgttaacatc atgtcaagcc aatcccatct caacatctca gatgcataaa   8700
tggatgggaa gttggttaat gtctgataat catgatgcca gtcaagggta tagtttttta   8760
catgaagtgg acaaagaggc agaaataaca tttgacgtgg tggagacctt catccgcggc   8820
tggggcaaca aaccaattga atacatcaaa aaggaaagat ggactgactc attcaaaatt   8880
ctcgcttatt tgtgtcaaaa gtttttggac ttacacaagt tgacattaat cttaaatgct   8940
gtctctgagg tggaattgct caacttggcg aggactttca aaggcaaagt cagaagaagt   9000
tctcatggaa cgaacatatg caggattagg gttcccagct tgggtcctac ttttatttca   9060
gaaggatggg cttacttcaa gaaacttgat attctaatgg accgaaactt tctgttaatg   9120
gtcaaagatg tgattatagg gaggatgcaa acggtgctat ccatggtatg tagaatagac   9180
aacctgttct cagagcaaga catcttctcc cttctaaata tctacagaat tggagataaa   9240
attgtggaga ggcagggaaa tttttcttat gacttgatta aaatggtgga accgatatgc   9300
aacttgaagc tgatgaaatt agcaagagaa tcaaggcctt tagtcccaca attccctcat   9360
tttgaaaatc atatcaagac ttctgttgat gaaggggcaa aaattgaccg aggtataaga   9420
ttcctccatg atcagataat gagtgtgaaa acagtggatc tcacactggt gatttatgga   9480
tcgttcagac attggggtca tccttttata gattattaca ctggactaga aaaattacat   9540
tcccaagtaa ccatgaagaa agatattgat gtgtcatatg caaaagcact tgcaagtgat   9600
ttagctcgga ttgttctatt tcaacagttc aatgatcata aaaagtggtt cgtgaatgga   9660
gacttgctcc ctcatgatca tccctttaaa agtcatgtta aagaaaatac atggcccaca   9720
gctgctcaag ttcaagattt tggagataaa tggcatgaac ttccgctgat taaatgtttt   9780
gaaataccccg acttactaga cccatcgata atatactctg acaaaagtca ttcaatgaat   9840
aggtcagagg tgttgaaaca tgtccgaatg aatccgaaca ctcctatccc tagtaaaaag   9900
gtgttgcaga ctatgttgga cacaaaggct accaattgga aagaatttct taaagagatt   9960
gatgagaagg gcttagatga tgatgatcta attattggtc ttaaaggaaa ggagagggaa  10020
ctgaagttgg caggtagatt tttctcccta atgtcttgga aattgcgaga atactttgta  10080
attaccgaat atttgataaa gactcatttc gtccctatgt ttaaaggcct gacaatggcg  10140
gacgatctaa ctgcagtcat taaaaagatg ttagattcct catccggcca aggattgaag  10200
tcatatgagg caatttgcat agccaatcac attgattacg aaaaatggaa taaccaccaa  10260
aggaagttat caaacggccc agtgttccga gttatgggcc agttcttagg ttatccatcc  10320
ttaatcgaga gaactcatga attttttgag aaaagtctta tatactacaa tggaagacca  10380
gacttgatgc gtgttcacaa caacacactg atcaattcaa cctcccaacg agtttgttgg  10440
caaggacaag agggtggact ggaaggtcta cggcaaaaag gatggactat cctcaatcta  10500
ctggttattc aaagagaggc taaaatcaga aacactgctg tcaaagtctt ggcacaaggt  10560
gataatcaag ttatttgcac acagtataaa acgaagaaat cgagaaacgt tgtagaatta  10620
cagggtgctc tcaatcaaat ggtttctaat aatgagaaaa ttatgactgc aatcaaaata  10680
gggacaggga agttaggact tttgataaat gacgatgaga ctatgcaatc tgcagattac  10740
ttgaattatg gaaaaatacc gattttccgt ggagtgatta gagggttaga gaccaagaga  10800
tggtcacgag tgacttgtgt caccaatgac caaataccca cttgtgctaa tataatgagc  10860
tcagtttcca caaatgctct caccgtagct cattttgctg agaacccaat caatgccatg  10920
atacagtaca attattttgg gacatttgct agactcttgt tgatgatgca tgatcctgct  10980
```

-continued

```
cttcgtcaat cattgtatga agttcaagat aagataccgg gcttgcacag ttctactttc  11040
aaatacgcca tgttgtattt ggacccttcc attggaggag tgtcgggcat gtctttgtcc  11100
aggtttttga ttagagcctt cccagatccc gtaacagaaa gtctctcatt ctggagattc  11160
atccatgtac atgctcgaag tgagcatctg aaggagatga gtgcagtatt tggaaacccc  11220
gagatagcca agtttcgaat aactcacata gacaagctag tagaagatcc aacctctctg  11280
aacatcgcta tgggaatgag tccagcgaac ttgttaaaga ctgaggttaa aaaatgctta  11340
atcgaatcaa gacaaaccat caggaaccag gtgattaagg atgcaaccat atatttgtat  11400
catgaagagg atcggctcag aagtttctta tggtcaataa atcctctgtt ccctagattt  11460
ttaagtgaat tcaaatcagg cacttttttg ggagtcgcag acgggctcat cagtctattt  11520
caaaattctc gtactattcg gaactccttt aagaaaaagt atcataggga attggatgat  11580
ttgattgtga ggagtgaggt atcctctttg acacatttag ggaaacttca tttgagaagg  11640
ggatcatgta aaatgtggac atgttcagct actcatgctg acacattaag atacaaatcc  11700
tggggccgta cagttattgg gacaactgta ccccatccat tagaaatgtt gggtccacaa  11760
catcgaaaag agactccttg tgcaccatgt aacacatcag ggttcaatta tgtttctgtg  11820
cattgtccag acgggatcca tgacgtcttt agttcacggg gaccattgcc tgcttatcta  11880
gggtctaaaa catctgaatc tacatctatt ttgcagcctt gggaaaggga aagcaaagtc  11940
ccactgatta aaagagctac acgtcttaga gatgctatct cttggtttgt tgaacccgac  12000
tctaaactag caatgactat actttctaac atccactctt taacaggcga agaatggacc  12060
aaaaggcagc atgggttcaa aagaacaggg tctgcccttc ataggttttc gacatctcgg  12120
atgagccatg gtgggttcgc atctcagagc actgcagcat tgaccaggtt gatggcaact  12180
acagacacca tgagggatct gggagatcag aatttcgact tttattccaa agcaacgttg  12240
ctctatgctc aaattaccac cactgttgca agagacggat ggatcaccag ttgtacagat  12300
cattatcata ttgcctgtaa gtcctgtttg agacccatag aagagatcac cctggactca  12360
agtatggact acacgccccc agatgtatcc catgtgctga agacatggag gaatggggaa  12420
ggttcgtggg gacaagagat aaaacagatc tatcctttag aagggaattg gaagaattta  12480
gcacctgctg agcaatccta tcaagtcggc agatgtatag gttttctata tggagacttg  12540
gcgtatagaa aatctactca tgccgaggac agttctctat ttcctctatc tatacaaggt  12600
cgtattagag gtcgaggttt cttaaaaggg ttgctagacg gattaatgag agcaagttgc  12660
tgccaagtaa tacaccggag aagtctggct catttgaaga ggccggccaa cgcagtgtac  12720
ggaggtttga tttacttgat tgataaattg agtgtatcac ctccattcct ttctcttact  12780
agatcaggac ctattagaga cgaattagaa acgattcccc acaagatccc aacctcctat  12840
ccgacaagca accgtgatat gggggtgatt gtcagaaatt acttcaaata ccaatgccgt  12900
ctaattgaaa agggaaaata cagatcacat tattcacaat tatggttatt ctcagatgtc  12960
ttatccatag acttcattgg accattctct atttccacca ccctcttgca aatcctatac  13020
aagccatttt tatctgggaa agataagaat gagttgagag agctggcaaa tctttcttca  13080
ttgctaagat caggagaggg gtgggaagac atacatgtga aattcttcac caaggacata  13140
ttattgtgtc cagaggaaat cagacatgct tgcaagttcg ggattgctaa ggataataat  13200
aaagacatga gctatccccc ttggggaagg gaatccagag ggacaattac aacaatccct  13260
gtttattata cgaccacccc ttacccaaag atgctagaga tgcctccaag aatccaaaat  13320
cccctgctgt ccggaatcag gttgggccaa ttaccaactg gcgctcatta taaaattcgg  13380
```

-continued

```
agtatattac atggaatggg aatccattac agggacttct tgagttgtgg agacggctcc  13440
ggagggatga ctgctgcatt actacgagaa aatgtgcata gcagaggaat attcaatagt  13500
ctgttagaat tatcagggtc agtcatgcga ggcgcctctc ctgagccccc cagtgcccta  13560
gaaactttag gaggagataa atcgagatgt gtaaatggtg aaacatgttg ggaatatcca  13620
tctgacttat gtgacccaag gacttgggac tatttcctcc gactcaaagc aggcttgggg  13680
cttcaaattg atttaattgt aatggatatg gaagttcggg attcttctac tagcctgaaa  13740
attgagacga atgttagaaa ttatgtgcac cggattttgg atgagcaagg agttttaatc  13800
tacaagactt atggaacata tatttgtgag agcgaaaaga atgcagtaac aatccttggt  13860
cccatgttca agacggtcga cttagttcaa acagaattta gtagttctca aacgtctgaa  13920
gtatatatgg tatgtaaagg tttgaagaaa ttaatcgatg aacccaatcc cgattggtct  13980
tccatcaatg aatcctggaa aaacctgtac gcattccagt catcagaaca ggaatttgcc  14040
agagcaaaga aggttagtac atactttacc ttgacaggta ttccctccca attcattcct  14100
gatccttttg taaacattga gactatgcta caaatattcg gagtacccac gggtgtgtct  14160
catgcggctg ccttaaaatc atctgataga cctgcagatt tattgaccat tagccttttt  14220
tatatggcga ttatatcgta ttataacatc aatcatatca gagtaggacc gatacctccg  14280
aacccccccat cagatggaat tgcacaaaat gtggggatcg ctataactgg tataagcttt  14340
tggctgagtt tgatggagaa agacattcca ctatatcaac agtgtttagc agttatccag  14400
caatcattcc cgattaggtg ggaggctgtt tcagtaaaag gaggatacaa gcagaagtgg  14460
agtactagag gtgatgggct cccaaaagat acccgaactt cagactcctt ggccccaatc  14520
gggaactgga tcagatctct ggaattggtc cgaaaccaag ttcgtctaaa tccattcaat  14580
gagatcttgt tcaatcagct atgtcgtaca gtggataatc atttgaaatg gtcaaatttg  14640
cgaagaaaca caggaatgat tgaatggatc aatagacgaa tttcaaaaga agaccggtct  14700
atactgatgt tgaagagtga cctacacgag gaaaactctt ggagagatta aaaaatcatg  14760
aggagactcc aaactttaag tatgaaaaaa actttgatcc ttaagaccct cttgtggttt  14820
ttatttttta tctggttttg tggtcttcgt gggtcggcat ggcatctcca cctcctcgcg  14880
gtccgacctg ggcatccgaa ggaggacgtc gtccactcgg atggctaagg gaggggcccc  14940
cgcggggctg ctaacaaagc ccgaaaggaa gctgagttgg ctgctgccac cgctgagcaa  15000
taactagcat aaccccttgg ggcctctaaa cgggtcttga ggggtttttt gctgaaagga  15060
ggaactatat ccggatcgag acctcgatac tagtgcggtg gagctccagc ttttgttccc  15120
tttagtgagg gttaatttcg agcttggcgt aatcatggtc atagctgttt cctgtgtgaa  15180
attgttatcc gctcacaatt ccacacaaca tacgagccgg aagcataaag tgtaaagcct  15240
ggggtgccta atgagtgagc taactcacat taattgcgtt gcgctcactg cccgctttcc  15300
agtcgggaaa cctgtcgtgc cagctgcatt aatgaatcgg ccaacgcgcg gggagaggcg  15360
gtttgcgtat tgggcgctct tccgcttcct cgctcactga ctcgctgcgc tcggtcgttc  15420
ggctgcggcg agcggtatca gctcactcaa aggcggtaat acggttatcc acagaatcag  15480
gggataacgc aggaaagaac atgtgagcaa aaggccagca aaaggccagg aaccgtaaaa  15540
aggccgcgtt gctggcgttt ttccataggc tccgcccccc tgacgagcat cacaaaaatc  15600
gacgctcaag tcagaggtgg cgaaacccga caggactata aagataccag gcgtttcccc  15660
ctggaagctc cctcgtgcgc tctcctgttc cgaccctgcc gcttaccgga tacctgtccg  15720
cctttctccc ttcgggaagc gtggcgcttt ctcatagctc acgctgtagg tatctcagtt  15780
```

```
cggtgtaggt cgttcgctcc aagctgggct gtgtgcacga acccccgtt cagcccgacc  15840

gctgcgcctt atccggtaac tatcgtcttg agtccaaccc ggtaagacac gacttatcgc  15900

cactggcagc agccactggt aacaggatta gcagagcgag gtatgtaggc ggtgctacag  15960

agttcttgaa gtggtggcct aactacggct acactagaag gacagtattt ggtatctgcg  16020

ctctgctgaa gccagttacc ttcggaaaaa gagttggtag ctcttgatcc ggcaaacaaa  16080

ccaccgctgg tagcggtggt ttttttgttt gcaagcagca gattacgcgc agaaaaaaag  16140

gatctcaaga agatcctttg atcttttcta cggggtctga cgctcagtgg aacgaaaact  16200

cacgttaagg gattttggtc atgagattat caaaaaggat cttcacctag atccttttaa  16260

attaaaaatg aagttttaaa tcaatctaaa gtatatatga gtaaacttgg tctgacagtt  16320

accaatgctt aatcagtgag gcacctatct cagcgatctg tctatttcgt tcatccatag  16380

ttgcctgact ccccgtcgtg tagataacta cgatacggga gggcttacca tctggcccca  16440

gtgctgcaat gataccgcga gacccacgct caccggctcc agatttatca gcaataaacc  16500

agccagccgg aagggccgag cgcagaagtg gtcctgcaac tttatccgcc tccatccagt  16560

ctattaattg ttgccgggaa gctagagtaa gtagttcgcc agttaatagt ttgcgcaacg  16620

ttgttgccat tgctacaggc atcgtggtgt cacgctcgtc gtttggtatg gcttcattca  16680

gctccggttc ccaacgatca aggcgagtta catgatcccc catgttgtgc aaaaaagcgg  16740

ttagctcctt cggtcctccg atcgttgtca gaagtaagtt ggccgcagtg ttatcactca  16800

tggttatggc agcactgcat aattctctta ctgtcatgcc atccgtaaga tgcttttctg  16860

tgactggtga gtactcaacc aagtcattct gagaatagtg tatgcggcga ccgagttgct  16920

cttgcccggc gtcaatacgg gataataccg cgccacatag cagaacttta aaagtgctca  16980

tcattggaaa acgttcttcg gggcgaaaac tctcaaggat cttaccgctg ttgagatcca  17040

gttcgatgta acccactcgt gcacccaact gatcttcagc atcttttact ttcaccagcg  17100

tttctgggtg agcaaaaaca ggaaggcaaa atgccgcaaa aaagggaata agggcgacac  17160

ggaaatgttg aatactcata ctcttccttt ttcaatatta ttgaagcatt tatcagggtt  17220

attgtctcat gagcggatac atatttgaat gtatttagaa aaataaacaa ataggggttc  17280

cgcgcacatt tccccgaaaa gtgc                                          17304
```

<210> SEQ ID NO 2
<211> LENGTH: 15104
<212> TYPE: DNA
<213> ORGANISM: Artificial Sequence
<220> FEATURE:
<223> OTHER INFORMATION: pVSV-GFP

<400> SEQUENCE: 2

```
cacctaaatt gtaagcgtta atattttgtt aaaattcgcg ttaaattttt gttaaatcag     60

ctcatttttt aaccaatagg ccgaaatcgg caaaatccct tataaatcaa aagaatagac    120

cgagataggg ttgagtgttg ttccagtttg gaacaagagt ccactattaa agaacgtgga    180

ctccaacgtc aaagggcgaa aaaccgtcta tcagggcgat ggcccactac gtgaaccatc    240

accctaatca agttttttgg ggtcgaggtg ccgtaaagca ctaaatcgga accctaaagg    300

gagcccccga tttagagctt gacggggaaa gccggcgaac gtggcgagaa aggaagggaa    360

gaaagcgaaa ggagcgggcg ctagggcgct ggcaagtgta gcggtcacgc tgcgcgtaac    420

caccacaccc gccgcgctta atgcgccgct acagggcgcg tcccattcgc cattcaggct    480

gcgcaactgt tgggaagggc gatcggtgcg ggcctcttcg ctattacgcc agctggcgaa    540
```

-continued

```
agggggatgt gctgcaaggc gattaagttg ggtaacgcca gggttttccc agtcacgacg    600
ttgtaaaacg acggccagtg aattgtaata cgactcacta tagggcgaat tgggtaccgg    660
gcccccccctc gagttgtaat acgactcact atagggacga agacaaacaa accattatta    720
tcattaaaag gctcaggaga aactttaaca gtaatcaaaa tgtctgttac agtcaagaga    780
atcattgaca acacagtcat agttccaaaa cttcctgcaa atgaggatcc agtggaatac    840
ccggcagatt acttcagaaa atcaaaggag attcctcttt acatcaatac tacaaaaagt    900
ttgtcagatc taagaggata tgtctaccaa ggcctcaaat ccggaaatgt atcaatcata    960
catgtcaaca gctacttgta tggagcatta aaggacatcc ggggtaagtt ggataaagat   1020
tggtcaagtt tcggaataaa catcgggaaa gcaggggata caatcggaat atttgacctt   1080
gtatccttga aagccctgga cggcgtactt ccagatggag tatcggatgc ttccagaacc   1140
agcgcagatg acaaatggtt gcctttgtat ctacttggct tatacagagt gggcagaaca   1200
caaatgcctg aatacagaaa aaagctcatg gatgggctga caaatcaatg caaaatgatc   1260
aatgaacagt ttgaacctct tgtgccagaa ggtcgtgaca tttttgatgt gtggggaaat   1320
gacagtaatt acacaaaaat tgtcgctgca gtggacatgt tcttccacat gttcaaaaaa   1380
catgaatgtg cctcgttcag atacggaact attgtttcca gattcaaaga ttgtgctgca   1440
ttggcaacat ttggacacct ctgcaaaata accggaatgt ctacagaaga tgtaacgacc   1500
tggatcttga accgagaagt tgcagatgaa atggtccaaa tgatgcttcc aggccaagaa   1560
attgacaagg ccgattcata catgccttat ttgatcgact ttggattgtc ttctaagtct   1620
ccatattctt ccgtcaaaaa ccctgccttc cacttctggg ggcaattgac agctcttctg   1680
ctcagatcca ccagagcaag gaatgcccga cagcctgatg acattgagta tacatctctt   1740
actacagcag gtttgttgta cgcttatgca gtaggatcct ctgccgactt ggcacaacag   1800
ttttgtgttg gagataacaa atacactcca gatgatagta ccggaggatt gacgactaat   1860
gcaccgccac aaggcagaga tgtggtcgaa tggctcggat ggtttgaaga tcaaaacaga   1920
aaaccgactc ctgatatgat gcagtatgcg aaaagagcag tcatgtcact gcaaggccta   1980
agagagaaga caattggcaa gtatgctaag tcagaatttg acaaatgacc ctataattct   2040
cagatcacct attatatatt atgctacata tgaaaaaaac taacagatat catggataat   2100
ctcacaaaag ttcgtgagta tctcaagtcc tattctcgtc tggatcaggc ggtaggagag   2160
atagatgaga tcgaagcaca acgagctgaa aagtccaatt atgagttgtt ccaagaggat   2220
ggagtggaag agcatactaa gccctcttat tttcaggcag cagatgattc tgacacagaa   2280
tctgaaccag aaattgaaga caatcaaggt ttgtatgcac cagatccaga agctgagcaa   2340
gttgaaggct ttatacaggg gcctttagat gactatgcag atgaggaagt ggatgttgta   2400
tttacttcgg actggaaaca gcctgagctt gaatctgacg agcatggaaa gaccttacgg   2460
ttgacatcgc cagagggttt aagtggagag cagaaatccc agtggctttc gacgattaaa   2520
gcagtcgtgc aaagtgccaa atactggaat ctggcagagt gcacatttga agcatcggga   2580
gaaggggtca ttatgaagga gcgccagata actccggatg tatataaggt cactccagtg   2640
atgaacacac atccgtccca atcagaagca gtatcagatg tttggtctct ctcaaagaca   2700
tccatgactt tccaacccaa gaaagcaagt cttcagcctc tcaccatatc cttggatgaa   2760
ttgttctcat ctagaggaga gttcatctct gtcggaggtg acggacgaat gtctcataaa   2820
gaggccatcc tgctcggcct gagatacaaa aagttgtaca atcaggcgag agtcaaatat   2880
tctctgtaga ctatgaaaaa aagtaacaga tatcacgatc taagtgttat cccaatccat   2940
```

-continued

```
tcatcatgag ttccttaaag aagattctcg gtctgaaggg gaaaggtaag aaatctaaga   3000
aattagggat cgcaccaccc ccttatgaag aggacactag catggagtat gctccgagcg   3060
ctccaattga caaatcctat tttggagttg acgagatgga cacctatgat ccgaatcaat   3120
taagatatga gaaattcttc tttacagtga aaatgacggt tagatctaat cgtccgttca   3180
gaacatactc agatgtggca gccgctgtat cccattggga tcacatgtac atcggaatgg   3240
cagggaaacg tcccttctac aaaatcttgg ctttttttggg ttcttctaat ctaaaggcca   3300
ctccagcggt attggcagat caaggtcaac cagagtatca cactcactgc gaaggcaggg   3360
cttatttgcc acataggatg ggaagaccc ctcccatgct caatgtacca gagcacttca   3420
gaagaccatt caatataggt ctttacaagg gaacgattga gctcacaatg accatctacg   3480
atgatgagtc actggaagca gctcctatga tctgggatca tttcaattct tccaaatttt   3540
ctgatttcag agagaaggcc ttaatgtttg gcctgattgt cgagaaaaag gcatctggag   3600
cgtgggtcct ggattctatc agccacttca aatgagctag tctaacttct agcttctgaa   3660
caatccccgg tttactcagt ctctcctaat tccagcctct cgaacaacta atatcctgtc   3720
ttttctatcc ctatgaaaaa aactaacaga gatcgatccc ctagtggatc cccgcggatg   3780
gtgagcaagg gcgaggagct gttcaccggg gtggtgccca tcctggtcga gctggacggc   3840
gacgtaaacg gccacaagtt cagcgtgtcc ggcgagggcg agggcgatgc cacctacggc   3900
aagctgaccc tgaagttcat ctgcaccacc ggcaagctgc ccgtgccctg gcccaccctc   3960
gtgaccaccc tgacctacgg cgtgcagtgc ttcagccgct accccgacca catgaagcag   4020
cacgacttct tcaagtccgc catgcccgaa ggctacgtcc aggagcgcac catcttcttc   4080
aaggacgacg gcaactacaa gacccgcgcc gaggtgaagt tcgagggcga caccctggtg   4140
aaccgcatcg agctgaaggg catcgacttc aaggaggacg gcaacatcct ggggcacaag   4200
ctggagtaca actacaacag ccacaacgtc tatatcatgg ccgacaagca gaagaacggc   4260
atcaaggtga acttcaagat ccgccacaac atcgaggacg gcagcgtgca gctcgccgac   4320
cactaccagc agaacacccc catcggcgac ggccccgtgc tgctgcccga caaccactac   4380
ctgagcaccc agtccgccct gagcaaagac cccaacgaga agcgcgatca catggtcctg   4440
ctggagttcg tgaccgccgc cgggatcact ctcggcatgg acgagctgta caagtaagaa   4500
ttcgatggga ccatggaaca cgtgtatgaa aaaaactaac agagatcgat ctgtttacgc   4560
gtcactatga agtgcctttt gtacttagcc tttttattca ttggggtgaa ttgcaagttc   4620
accatagttt ttccacacaa ccaaaaagga aactggaaaa atgttccttc taattaccat   4680
tattgcccgt caagctcaga tttaaattgg cataatgact taataggcac agccatacaa   4740
gtcaaaatgc ccaagagtca caaggctatt caagcagacg gttggatgtg tcatgcttcc   4800
aaatgggtca ctacttgtga tttccgctgg tatggaccga agtatataac acagtccatc   4860
cgatccttca ctccatctgt agaacaatgc aaggaaagca ttgaacaaac gaaacaagga   4920
acttggctga atccaggctt ccctcctcaa agttgtggat atgcaactgt gacggatgcc   4980
gaagcagtga ttgtccaggt gactcctcac catgtgctgg ttgatgaata cacaggagaa   5040
tgggttgatt cacagttcat caacggaaaa tgcagcaatt acatatgccc cactgtccat   5100
aactctacaa cctggcattc tgactataag gtcaaagggc tatgtgattc taacctcatt   5160
tccatggaca tcaccttctt ctcagaggac ggagagctat catccctggg aaaggagggc   5220
acagggttca gaagtaacta ctttgcttat gaaactggag gcaaggcctg caaaatgcaa   5280
tactgcaagc attggggagt cagactccca tcaggtgtct ggttcgagat ggctgataag   5340
```

```
gatctctttg ctgcagccag attccctgaa tgcccagaag ggtcaagtat ctctgctcca   5400

tctcagacct cagtggatgt aagtctaatt caggacgttg agaggatctt ggattattcc   5460

ctctgccaag aaacctggag caaaatcaga gcgggtcttc caatctctcc agtggatctc   5520

agctatcttg ctcctaaaaa cccaggaacc ggtcctgctt tcaccataat caatggtacc   5580

ctaaaatact ttgagaccag atacatcaga gtcgatattg ctgctccaat cctctcaaga   5640

atggtcggaa tgatcagtgg aactaccaca gaaagggaac tgtgggatga ctgggcacca   5700

tatgaagacg tggaaattgg acccaatgga gttctgagga ccagttcagg atataagttt   5760

cctttataca tgattggaca tggtatgttg gactccgatc ttcatcttag ctcaaaggct   5820

caggtgttcg aacatcctca cattcaagac gctgcttcgc aacttcctga tgatgagagt   5880

ttatttttg gtgatactgg gctatccaaa aatccaatcg agcttgtaga aggttggttc   5940

agtagttgga aaagctctat tgcctctttt ttctttatca tagggttaat cattggacta   6000

ttcttggttc tccgagttgg tatccatctt tgcattaaat taaagcacac caagaaaaga   6060

cagatttata cagacataga gatgaaccga cttggaaagt aactcaaatc ctgctagcca   6120

gattcttcat gtttggacca aatcaacttg tgataccatg ctcaaagagg cctcaattat   6180

atttgagttt ttaattttta tgaaaaaaac taacagcaat catggaagtc cacgattttg   6240

agaccgacga gttcaatgat ttcaatgaag atgactatgc cacaagagaa ttcctgaatc   6300

ccgatgagcg catgacgtac ttgaatcatg ctgattacaa tttgaattct cctctaatta   6360

gtgatgatat tgacaatttg atcaggaaat tcaattctct tccgattccc tcgatgtggg   6420

atagtaagaa ctgggatgga gttcttgaga tgttaacatc atgtcaagcc aatcccatct   6480

caacatctca gatgcataaa tggatgggaa gttggttaat gtctgataat catgatgcca   6540

gtcaagggta tagtttttta catgaagtgg acaaagaggc agaaataaca tttgacgtgg   6600

tggagacctt catccgcggc tggggcaaca aaccaattga atacatcaaa aaggaaagat   6660

ggactgactc attcaaaatt ctcgcttatt tgtgtcaaaa gtttttggac ttacacaagt   6720

tgacattaat cttaaatgct gtctctgagg tggaattgct caacttggcg aggactttca   6780

aaggcaaagt cagaagaagt tctcatggaa cgaacatatg caggattagg gttcccagct   6840

tgggtcctac ttttatttca gaaggatggg cttacttcaa gaaacttgat attctaatgg   6900

accgaaactt tctgttaatg gtcaaagatg tgattatagg gaggatgcaa acggtgctat   6960

ccatggtatg tagaatagac aacctgttct cagagcaaga catcttctcc cttctaaata   7020

tctacagaat tggagataaa attgtggaga ggcagggaaa tttttcttat gacttgatta   7080

aaatggtgga accgatatgc aacttgaagc tgatgaaatt agcaagagaa tcaaggcctt   7140

tagtcccaca attccctcat tttgaaaatc atatcaagac ttctgttgat gaaggggcaa   7200

aaattgaccg aggtataaga ttcctccatg atcagataat gagtgtgaaa acagtggatc   7260

tcacactggt gatttatgga tcgttcagac attggggtca tccttttata gattattaca   7320

ctggactaga aaaattacat tcccaagtaa ccatgaagaa agatattgat gtgtcatatg   7380

caaaagcact tgcaagtgat ttagctcgga ttgttctatt tcaacagttc aatgatcata   7440

aaaagtggtt cgtgaatgga gacttgctcc ctcatgatca tccctttaaa agtcatgtta   7500

aagaaaatac atggcccaca gctgctcaag ttcaagattt tggagataaa tggcatgaac   7560

ttccgctgat taaatgtttt gaaatacccg acttactaga cccatcgata atatactctg   7620

acaaaagtca ttcaatgaat aggtcagagg tgttgaaaca tgtccgaatg aatccgaaca   7680

ctcctatccc tagtaaaaag gtgttgcaga ctatgttgga cacaaaggct accaattgga   7740
```

```
aagaatttct taaagagatt gatgagaagg gcttagatga tgatgatcta attattggtc   7800
ttaaaggaaa ggagagggaa ctgaagttgg caggtagatt tttctcccta atgtcttgga   7860
aattgcgaga atactttgta attaccgaat atttgataaa gactcatttc gtccctatgt   7920
ttaaaggcct gacaatggcg gacgatctaa ctgcagtcat taaaaagatg ttagattcct   7980
catccggcca aggattgaag tcatatgagg caatttgcat agccaatcac attgattacg   8040
aaaaatggaa taaccaccaa aggaagttat caaacggccc agtgttccga gttatgggcc   8100
agttcttagg ttatccatcc ttaatcgaga gaactcatga attttttgag aaaagtctta   8160
tatactacaa tggaagacca gacttgatgc gtgttcacaa caacacactg atcaattcaa   8220
cctcccaacg agtttgttgg caaggacaag agggtggact ggaaggtcta cggcaaaaag   8280
gatggactat cctcaatcta ctggttattc aaagagaggc taaaatcaga aacactgctg   8340
tcaaagtctt ggcacaaggt gataatcaag ttatttgcac acagtataaa acgaagaaat   8400
cgagaaacgt tgtagaatta cagggtgctc tcaatcaaat ggtttctaat aatgagaaaa   8460
ttatgactgc aatcaaaata gggacaggga agttaggact tttgataaat gacgatgaga   8520
ctatgcaatc tgcagattac ttgaattatg gaaaaatacc gattttccgt ggagtgatta   8580
gagggttaga gaccaagaga tggtcacgag tgacttgtgt caccaatgac caaataccca   8640
cttgtgctaa tataatgagc tcagtttcca caaatgctct caccgtagct cattttgctg   8700
agaacccaat caatgccatg atacagtaca attattttgg gacatttgct agactcttgt   8760
tgatgatgca tgatcctgct cttcgtcaat cattgtatga agttcaagat aagataccgg   8820
gcttgcacag ttctactttc aaatacgcca tgttgtattt ggacccttcc attggaggag   8880
tgtcgggcat gtctttgtcc aggtttttga ttagagcctt cccagatccc gtaacagaaa   8940
gtctctcatt ctggagattc atccatgtac atgctcgaag tgagcatctg aaggagatga   9000
gtgcagtatt tggaaacccc gagatagcca agtttcgaat aactcacata gacaagctag   9060
tagaagatcc aacctctctg aacatcgcta tgggaatgag tccagcgaac ttgttaaaga   9120
ctgaggttaa aaaatgctta atcgaatcaa gacaaaccat caggaaccag gtgattaagg   9180
atgcaaccat atatttgtat catgaagagg atcggctcag aagtttctta tggtcaataa   9240
atcctctgtt ccctagattt ttaagtgaat tcaaatcagg cacttttttg ggagtcgcag   9300
acgggctcat cagtctattt caaaattctc gtactattcg gaactccttt aagaaaaagt   9360
atcataggga attggatgat ttgattgtga ggagtgaggt atcctctttg acacatttag   9420
ggaaacttca tttgagaagg ggatcatgta aaatgtggac atgttcagct actcatgctg   9480
acacattaag atacaaatcc tggggccgta cagttattgg gacaactgta ccccatccat   9540
tagaaatgtt gggtccacaa catcgaaaag agactccttg tgcaccatgt aacacatcag   9600
ggttcaatta tgtttctgtg cattgtccag acgggatcca tgacgtcttt agttcacggg   9660
gaccattgcc tgcttatcta gggtctaaaa catctgaatc tacatctatt ttgcagcctt   9720
gggaaaggga aagcaaagtc ccactgatta aaagagctac acgtcttaga gatgctatct   9780
cttggtttgt tgaacccgac tctaaactag caatgactat actttctaac atccactctt   9840
taacaggcga agaatggacc aaaaggcagc atgggttcaa aagaacaggg tctgcccttc   9900
ataggttttc gacatctcgg atgagccatg gtgggttcgc atctcagagc actgcagcat   9960
tgaccaggtt gatggcaact acagacacca tgagggatct gggagatcag aatttcgact  10020
ttttattcca agcaacgttg ctctatgctc aaattaccac cactgttgca agagacggat  10080
ggatcaccag ttgtacagat cattatcata ttgcctgtaa gtcctgtttg agacccatag  10140
```

```
aagagatcac cctggactca agtatggact acacgccccc agatgtatcc catgtgctga  10200
agacatggag gaatggggaa ggttcgtggg gacaagagat aaaacagatc tatcctttag  10260
aagggaattg gaagaattta gcacctgctg agcaatccta tcaagtcggc agatgtatag  10320
gttttctata tggagacttg gcgtatagaa aatctactca tgccgaggac agttctctat  10380
ttcctctatc tatacaaggt cgtattagag gtcgaggttt cttaaaaggg ttgctagacg  10440
gattaatgag agcaagttgc tgccaagtaa tacaccggag aagtctggct catttgaaga  10500
ggccggccaa cgcagtgtac ggaggtttga tttacttgat tgataaattg agtgtatcac  10560
ctccattcct ttctcttact agatcaggac ctattagaga cgaattagaa acgattcccc  10620
acaagatccc aacctcctat ccgacaagca accgtgatat gggggtgatt gtcagaaatt  10680
acttcaaata ccaatgccgt ctaattgaaa agggaaaata cagatcacat tattcacaat  10740
tatggttatt ctcagatgtc ttatccatag acttcattgg accattctct atttccacca  10800
ccctcttgca aatcctatac aagccatttt tatctgggaa agataagaat gagttgagag  10860
agctggcaaa tctttcttca ttgctaagat caggagaggg gtgggaagac atacatgtga  10920
aattcttcac caaggacata ttattgtgtc cagaggaaat cagacatgct tgcaagttcg  10980
ggattgctaa ggataataat aaagacatga gctatccccc ttggggaagg gaatccagag  11040
ggacaattac aacaatccct gtttattata cgaccacccc ttacccaaag atgctagaga  11100
tgcctccaag aatccaaaat cccctgctgt ccggaatcag gttgggccaa ttaccaactg  11160
gcgctcatta taaaattcgg agtatattac atggaatggg aatccattac agggacttct  11220
tgagttgtgg agacggctcc ggagggatga ctgctgcatt actacgagaa aatgtgcata  11280
gcagaggaat attcaatagt ctgttagaat tatcagggtc agtcatgcga ggcgcctctc  11340
ctgagccccc cagtgcccta gaaactttag gaggagataa atcgagatgt gtaaatggtg  11400
aaacatgttg ggaatatcca tctgacttat gtgacccaag gacttgggac tatttcctcc  11460
gactcaaagc aggcttgggg cttcaaattg atttaattgt aatggatatg gaagttcggg  11520
attcttctac tagcctgaaa attgagacga atgttagaaa ttatgtgcac cggattttgg  11580
atgagcaagg agttttaatc tacaagactt atggaacata tatttgtgag agcgaaaaga  11640
atgcagtaac aatccttggt cccatgttca agacggtcga cttagttcaa acagaattta  11700
gtagttctca aacgtctgaa gtatatatgg tatgtaaagg tttgaagaaa ttaatcgatg  11760
aacccaatcc cgattggtct tccatcaatg aatcctggaa aaacctgtac gcattccagt  11820
catcagaaca ggaatttgcc agagcaaaga aggttagtac atactttacc ttgacaggta  11880
ttccctccca attcattcct gatccttttg taaacattga gactatgcta caaatattcg  11940
gagtacccac gggtgtgtct catgcggctg ccttaaaatc atctgataga cctgcagatt  12000
tattgaccat tagccttttt tatatggcga ttatatcgta ttataacatc aatcatatca  12060
gagtaggacc gatacctccg aacccccat cagatggaat tgcacaaaat gtggggatcg  12120
ctataactgg tataagcttt tggctgagtt tgatggagaa agacattcca ctatatcaac  12180
agtgtttagc agttatccag caatcattcc cgattaggtg ggaggctgtt tcagtaaaag  12240
gaggatacaa gcagaagtgg agtactagag gtgatgggct cccaaaagat acccgaactt  12300
cagactcctt ggccccaatc gggaactgga tcagatctct ggaattggtc cgaaaccaag  12360
ttcgtctaaa tccattcaat gagatcttgt tcaatcagct atgtcgtaca gtggataatc  12420
atttgaaatg gtcaaatttg cgaagaaaca caggaatgat tgaatggatc aatagacgaa  12480
tttcaaaaga agaccggtct atactgatgt tgaagagtga cctacacgag gaaaactctt  12540
```

```
ggagagatta aaaaatcatg aggagactcc aaactttaag tatgaaaaaa actttgatcc 12600
ttaagaccct cttgtggttt ttattttttta tctggttttg tggtcttcgt gggtcggcat 12660
ggcatctcca cctcctcgcg gtccgacctg ggcatccgaa ggaggacgtc gtccactcgg 12720
atggctaagg gaggggcccc cgcggggctg ctaacaaagc ccgaaaggaa gctgagttgg 12780
ctgctgccac cgctgagcaa taactagcat aaccccttgg ggcctctaaa cgggtcttga 12840
ggggtttttt gctgaaagga ggaactatat ccggatcgag acctcgatac tagtgcggtg 12900
gagctccagc ttttgttccc tttagtgagg gttaatttcg agcttggcgt aatcatggtc 12960
atagctgttt cctgtgtgaa attgttatcc gctcacaatt ccacacaaca tacgagccgg 13020
aagcataaag tgtaaagcct ggggtgccta atgagtgagc taactcacat taattgcgtt 13080
gcgctcactg cccgctttcc agtcgggaaa cctgtcgtgc cagctgcatt aatgaatcgg 13140
ccaacgcgcg gggagaggcg gtttgcgtat tgggcgctct tccgcttcct cgctcactga 13200
ctcgctgcgc tcggtcgttc ggctgcggcg agcggtatca gctcactcaa aggcggtaat 13260
acggttatcc acagaatcag gggataacgc aggaaagaac atgtgagcaa aaggccagca 13320
aaaggccagg aaccgtaaaa aggccgcgtt gctggcgttt ttccataggc tccgcccccc 13380
tgacgagcat cacaaaaatc gacgctcaag tcagaggtgg cgaaacccga caggactata 13440
aagataccag gcgtttcccc ctggaagctc cctcgtgcgc tctcctgttc cgaccctgcc 13500
gcttaccgga tacctgtccg cctttctccc ttcgggaagc gtggcgcttt ctcatagctc 13560
acgctgtagg tatctcagtt cggtgtaggt cgttcgctcc aagctgggct gtgtgcacga 13620
accccccgtt cagcccgacc gctgcgcctt atccggtaac tatcgtcttg agtccaaccc 13680
ggtaagacac gacttatcgc cactggcagc agccactggt aacaggatta gcagagcgag 13740
gtatgtaggc ggtgctacag agttcttgaa gtggtggcct aactacggct acactagaag 13800
gacagtattt ggtatctgcg ctctgctgaa gccagttacc ttcggaaaaa gagttggtag 13860
ctcttgatcc ggcaaacaaa ccaccgctgg tagcggtggt ttttttgttt gcaagcagca 13920
gattacgcgc agaaaaaaag gatctcaaga agatcctttg atcttttcta cggggtctga 13980
cgctcagtgg aacgaaaact cacgttaagg gattttggtc atgagattat caaaaaggat 14040
cttcacctag atccttttaa attaaaaatg aagttttaaa tcaatctaaa gtatatatga 14100
gtaaacttgg tctgacagtt accaatgctt aatcagtgag gcacctatct cagcgatctg 14160
tctatttcgt tcatccatag ttgcctgact ccccgtcgtg tagataacta cgatacggga 14220
gggcttacca tctggcccca gtgctgcaat gataccgcga gacccacgct caccggctcc 14280
agatttatca gcaataaacc agccagccgg aagggccgag cgcagaagtg gtcctgcaac 14340
tttatccgcc tccatccagt ctattaattg ttgccgggaa gctagagtaa gtagttcgcc 14400
agttaatagt ttgcgcaacg ttgttgccat tgctacaggc atcgtggtgt cacgctcgtc 14460
gtttggtatg gcttcattca gctccggttc ccaacgatca aggcgagtta catgatcccc 14520
catgttgtgc aaaaaagcgg ttagctcctt cggtcctccg atcgttgtca gaagtaagtt 14580
ggccgcagtg ttatcactca tggttatggc agcactgcat aattctctta ctgtcatgcc 14640
atccgtaaga tgcttttctg tgactggtga gtactcaacc aagtcattct gagaatagtg 14700
tatgcggcga ccgagttgct cttgcccggc gtcaatacgg gataataccg cgccacatag 14760
cagaacttta aaagtgctca tcattggaaa acgttcttcg gggcgaaaac tctcaaggat 14820
cttaccgctg ttgagatcca gttcgatgta acccactcgt gcacccaact gatcttcagc 14880
atcttttact ttcaccagcg tttctgggtg agcaaaaaca ggaaggcaaa atgccgcaaa 14940
```

```
aaagggaata agggcgacac ggaaatgttg aatactcata ctcttccttt ttcaatatta  15000

ttgaagcatt tatcagggtt attgtctcat gagcggatac atatttgaat gtatttagaa  15060

aaataaacaa ataggggttc cgcgcacatt tccccgaaaa gtgc                   15104


<210> SEQ ID NO 3
<211> LENGTH: 6033
<212> TYPE: DNA
<213> ORGANISM: Artificial Sequence
<220> FEATURE:
<223> OTHER INFORMATION: pTM1-GFP

<400> SEQUENCE: 3

aagcttttgc gatcaataaa tggatcacaa ccagtatctc ttaacgatgt tcttcgcaga     60

tgatgattca ttttttaagt atttggctag tcaagatgat gaatcttcat tatctgatat    120

attgcaaatc actcaatatc tagactttct gttattatta ttgatccaat caaaaaataa    180

attagaagcc gtgggtcatt gttatgaatc tctttcagag gaatacagac aattgacaaa    240

attcacagac tttcaagatt ttaaaaaact gtttaacaag gtccctattg ttacagatgg    300

aagggtcaaa cttaataaag gatatttgtt cgactttgtg attagtttga tgcgattcaa    360

aaaagaatcc tctctagcta ccaccgcaat agatcctgtt agatacatag atcctcgtcg    420

caatatcgca ttttctaacg tgatggatat attaaagtcg aataaagtga acaataatta    480

attctttatt gtcatcatga acggcggaca tattcagttg ataatcggcc ccatgttttc    540

aggtaaaagt acagaattaa ttagacgagt tagacgttat caaatagctc aatataaatg    600

cgtgactata aaatattcta acgataatag atacggaacg ggactatgga cgcatgataa    660

gaataatttt gaagcattgg aagcaactaa actatgtgat gtcttggaat caattacaga    720

tttctccgtg ataggtatcg atgaaggaca gttctttcca gacattgttg aattgatctc    780

gatcccgcga aattaatacg actcactata gggagaccac aacggtttcc ctctagcggg    840

atcaattccg cccctctccc tcccccccc ctaacgttac tggccgaagc cgcttggaat    900

aaggccggtg tgcgtttgtc tatatgttat tttccaccat attgccgtct tttggcaatg    960

tgagggcccg gaaacctggc cctgtcttct tgacgagcat tcctaggggt ctttcccctc   1020

tcgccaaagg aatgcaaggt ctgttgaatg tcgtgaagga agcagttcct ctggaagctt   1080

cttgaagaca aacaacgtct gtagcgaccc tttgcaggca gcggaacccc ccacctggcg   1140

acaggtgcct ctgcggccaa aagccacgtg tataagatac acctgcaaag gcggcacaac   1200

cccagtgcca cgttgtgagt tggatagttg tggaaagagt caaatggctc tcctcaagcg   1260

tattcaacaa ggggctgaag gatgcccaga aggtacccca ttgtatggga tctgatctgg   1320

ggcctcggtg cacatgcttt acatgtgttt agtcgaggtt aaaaaacgtc taggcccccc   1380

gaaccacggg gacgtggttt tcctttgaaa aacacgataa taccatggtg agcaagggcg   1440

aggagctgtt caccggggtg gtgcccatcc tggtcgagct ggacggcgac gtaaacggcc   1500

acaagttcag cgtgtccggc gagggcgagg gcgatgccac ctacggcaag ctgaccctga   1560

agttcatctg caccaccggc aagctgcccg tgccctggcc caccctcgtg accaccctga   1620

cctacggcgt gcagtgcttc agccgctacc ccgaccacat gaagcagcac gacttcttca   1680

agtccgccat gcccgaaggc tacgtccagg agcgcaccat cttcttcaag gacgacggca   1740

actacaagac ccgcgccgag gtgaagttcg agggcgacac cctggtgaac cgcatcgagc   1800

tgaagggcat cgacttcaag gaggacggca acatcctggg gcacaagctg gagtacaact   1860

acaacagcca caacgtctat atcatggccg acaagcagaa gaacggcatc aaggtgaact   1920
```

-continued

```
tcaagatccg ccacaacatc gaggacggca gcgtgcagct cgccgaccac taccagcaga   1980
acacccccat cggcgacggc cccgtgctgc tgcccgacaa ccactacctg agcacccagt   2040
ccgccctgag caaagacccc aacgagaagc gcgatcacat ggtcctgctg gagttcgtga   2100
ccgccgccgg gatcactctc ggcatggacg agctgtacaa gtaagaattc gatatcaagc   2160
ttgtcgacga tccggctgct aacaaagccc gaaaggaagc tgagttggct gctgccaccg   2220
ctgagcaata actagcataa ccccttgggg cctctaaacg ggtcttgagg ggtttttttgc  2280
tgaaaggagg aactatatcc ggatcgagat caattctgtg agcgtatggc aaacgaagga   2340
aaaatagtta tagtagccgc actcgatggg acatttcaac gtaaaccgtt taataatatt   2400
ttgaatctta ttccattatc tgaaatggtg gtaaaactaa ctgctgtgtg tatgaaatgc   2460
tttaaggagg cttccttttc taaacgattg ggtgaggaaa ccgagataga aataatagga   2520
ggtaatgata tgtatcaatc ggtgtgtaga aagtgttaca tcgactcata atattatatt   2580
ttttatctaa aaaactaaaa ataaacattg attaaatttt aatataatac ttaaaaatgg   2640
atgttgtgtc gttagataaa ccgtttatgt attttgagga aattgataat gagttagatt   2700
acgaaccaga aagtgcaaat gaggtcgcaa aaaaactgcc gtatcaagga cagttaaaac   2760
tattactagg agaattattt tttcttagta agttacagcg acacggtata ttagatggtg   2820
ccaccgtagt gtatatagga tctgctcccg gtacacatat acgttatttg agagatcatt   2880
tctataattt aggagtgatc atcaaatgga tgctaattga cggccgccat catgatccta   2940
ttttaaatgg attgcgtgat gtgactctag tgactcggtt cgttgatgag gaatatctac   3000
gatccatcaa aaaacaactg catccttcta agattatttt aatttctgat gtgagatcca   3060
aacgaggagg aaatgaacct agtacggcgg atttactaag taattacgct ctacaaaatg   3120
tcatgattag tattttaaac cccgtggcgt ctagtcttaa atggagatgc ccgtttccag   3180
atcaatggat caaggacttt tatatcccac acggtaataa aatgttacaa cctttttgctc  3240
cttcatattc agggccgtcg ttttacaacg tcgtgactgg gaaaaccctg gcgttaccca   3300
acttaatcgc cttgcagcac atccccccttt cgccagctgg cgtaatagcg aagaggcccg  3360
caccgatcgc ccttcccaac agttgcgcag cctgaatggc gaatggcgcg acgcgccctg   3420
tagcggcgca ttaagcgcgg cgggtgtggt ggttacgcgc agcgtgaccg ctacacttgc   3480
cagcgcccta gcgcccgctc ctttcgcttt cttcccttcc tttctcgcca cgttcgccgg   3540
ctttccccgt caagctctaa atcgggggct ccctttaggg ttccgattta gtgctttacg   3600
gcacctcgac cccaaaaaac ttgattaggg tgatggttca cgtagtgggc catcgccctg   3660
atagacggtt tttcgccctt tgacgttgga gtccacgttc tttaatagtg gactcttgtt   3720
ccaaactgga acaacactca accctatctc ggtctattct tttgatttat aagggatttt   3780
gccgatttcg gcctattggt taaaaaatga gctgatttaa caaaaattta acgcgaattt   3840
taacaaaata ttaacgttta caatttccca ggtggcactt ttcggggaaa tgtgcgcgga   3900
acccctattt gtttattttt ctaaatacat tcaaatatgt atccgctcat gagacaataa   3960
ccctgataaa tgcttcaata atattgaaaa aggaagagta tgagtattca acatttccgt   4020
gtcgccctta ttcccttttt tgcggcattt tgccttcctg tttttgctca cccagaaacg   4080
ctggtgaaag taaaagatgc tgaagatcag ttgggtgcac gagtgggtta catcgaactg   4140
gatctcaaca gcggtaagat ccttgagagt tttcgccccg aagaacgttt tccaatgatg   4200
agcactttta aagttctgct atgtggcgcg gtattatccc gtattgacgc cgggcaagag   4260
caactcggtc gccgcataca ctattctcag aatgacttgg ttgagtactc accagtcaca   4320
```

```
gaaaagcatc ttacggatgg catgacagta agagaattat gcagtgctgc cataaccatg   4380

agtgataaca ctgcggccaa cttacttctg acaacgatcg gaggaccgaa ggagctaacc   4440

gcttttttgc acaacatggg ggatcatgta actcgccttg atcgttggga accggagctg   4500

aatgaagcca taccaaacga cgagcgtgac accacgatgc ctgtagcaat ggcaacaacg   4560

ttgcgcaaac tattaactgg cgaactactt actctagctt cccggcaaca attaatagac   4620

tggatggagg cggataaagt tgcaggacca cttctgcgct cggcccttcc ggctggctgg   4680

tttattgctg ataaatctgg agccggtgag cgtgggtctc gcggtatcat tgcagcactg   4740

gggccagatg gtaagccctc ccgtatcgta gttatctaca cgacggggag tcaggcaact   4800

atggatgaac gaaatagaca gatcgctgag ataggtgcct cactgattaa gcattggtaa   4860

ctgtcagacc aagtttactc atatatactt tagattgatt taaaacttca tttttaattt   4920

aaaaggatct aggtgaagat cctttttgat aatctcatga ccaaaatccc ttaacgtgag   4980

ttttcgttcc actgagcgtc agaccccgta gaaaagatca aaggatcttc ttgagatcct   5040

tttttctgc gcgtaatctg ctgcttgcaa acaaaaaaac caccgctacc agcggtggtt   5100

tgtttgccgg atcaagagct accaactctt tttccgaagg taactggctt cagcagagcg   5160

cagataccaa atactgtcct tctagtgtag ccgtagttag gccaccactt caagaactct   5220

gtagcaccgc ctacatacct cgctctgcta atcctgttac cagtggctgc tgccagtggc   5280

gataagtcgt gtcttaccgg gttggactca agacgatagt taccggataa ggcgcagcgg   5340

tcgggctgaa cggggggttc gtgcacacag cccagcttgg agcgaacgac ctacaccgaa   5400

ctgagatacc tacagcgtga gctatgagaa agcgccacgc ttcccgaagg gagaaaggcg   5460

gacaggtatc cggtaagcgg cagggtcgga acaggagagc gcacgaggga gcttccaggg   5520

ggaaacgcct ggtatcttta tagtcctgtc gggtttcgcc acctctgact tgagcgtcga   5580

tttttgtgat gctcgtcagg ggggcggagc ctatggaaaa acgccagcaa cgcggccttt   5640

ttacggttcc tggccttttg ctggcctttt gctcacatgt tctttcctgc gttatcccct   5700

gattctgtgg ataaccgtat taccgccttt gagtgagctg ataccgctcg ccgcagccga   5760

acgaccgagc gcagcgagtc agtgagcgag gaagcggaag agcgcccaat acgcaaaccg   5820

cctctccccg cgcgttggcc gattcattaa tgcagctggc acgacaggtt tcccgactgg   5880

aaagcgggca gtgagcgcaa cgcaattaat gtgagttagc tcactcatta ggcaccccag   5940

gctttacact ttatgcttcc ggctcgtatg ttgtgtggaa ttgtgagcgg ataacaattt   6000

cacacaggaa acagctatga ccatgattac gcc                                6033


<210> SEQ ID NO 4
<211> LENGTH: 3228
<212> TYPE: DNA
<213> ORGANISM: Artificial Sequence
<220> FEATURE:
<223> OTHER INFORMATION: pSP73-GFP

<400> SEQUENCE: 4

gaaccagatc tgatatcatc gatgaattct tacttgtaca gctcgtccat gccgagagtg     60

atcccggcgg cggtcacgaa ctccagcagg accatgtgat cgcgcttctc gttggggtct    120

ttgctcaggg cggactgggt gctcaggtag tggttgtcgg gcagcagcac ggggccgtcg    180

ccgatggggg tgttctgctg gtagtggtcg gcgagctgca cgctgccgtc ctcgatgttg    240

tggcggatct tgaagttcac cttgatgccg ttcttctgct tgtcggccat gatatagacg    300

ttgtggctgt tgtagttgta ctccagcttg tgccccagga tgttgccgtc ctccttgaag    360
```

-continued

```
tcgatgccct tcagctcgat gcggttcacc agggtgtcgc cctcgaactt cacctcggcg    420
cgggtcttgt agttgccgtc gtccttgaag aagatggtgc gctcctggac gtagccttcg    480
ggcatggcgg acttgaagaa gtcgtgctgc ttcatgtggt cggggtagcg gctgaagcac    540
tgcacgccgt aggtcagggt ggtcacgagg gtgggccagg gcacgggcag cttgccggtg    600
gtgcagatga acttcagggt cagcttgccg taggtggcat cgccctcgcc ctcgccggac    660
acgctgaact tgtggccgtt tacgtcgccg tccagctcga ccaggatggg caccaccccg    720
gtgaacagct cctcgccctt gctcaccatc cgcggggatc cactagttct agagcggccg    780
cctgcaggaa ttcgagctcg gtacccgggg atcctctaga gtcgacctgc aggcatgcaa    840
gcttcagctg ctcgaggccg gtctccctat agtgagtcgt attaatttcg ataagccagg    900
ttaacctgca ttaatgaatc ggccaacgcg cggggagagg cggtttgcgt attgggcgct    960
cttccgcttc ctcgctcact gactcgctgc gctcggtcgt tcggctgcgg cgagcggtat   1020
cagctcactc aaaggcggta atacggttat ccacagaatc aggggataac gcaggaaaga   1080
acatgtgagc aaaaggccag caaaaggcca ggaaccgtaa aaaggccgcg ttgctggcgt   1140
ttttccatag gctccgcccc cctgacgagc atcacaaaaa tcgacgctca agtcagaggt   1200
ggcgaaaccc gacaggacta taaagatacc aggcgtttcc ccctggaagc tccctcgtgc   1260
gctctcctgt tccgaccctg ccgcttaccg gatacctgtc cgcctttctc ccttcgggaa   1320
gcgtggcgct ttctcaatgc tcacgctgta ggtatctcag ttcggtgtag gtcgttcgct   1380
ccaagctggg ctgtgtgcac gaaccccccg ttcagcccga ccgctgcgcc ttatccggta   1440
actatcgtct tgagtccaac ccggtaagac acgacttatc gccactggca gcagccactg   1500
gtaacaggat tagcagagcg aggtatgtag gcggtgctac agagttcttg aagtggtggc   1560
ctaactacgg ctacactaga aggacagtat ttggtatctg cgctctgctg aagccagtta   1620
ccttcggaaa aagagttggt agctcttgat ccggcaaaca aaccaccgct ggtagcggtg   1680
gtttttttgt ttgcaagcag cagattacgc gcagaaaaaa aggatctcaa gaagatcctt   1740
tgatcttttc tacggggtct gacgctcagt ggaacgaaaa ctcacgttaa gggattttgg   1800
tcatgagatt atcaaaaagg atcttcacct agatcctttt aaattaaaaa tgaagtttta   1860
aatcaatcta aagtatatat gagtaaactt ggtctgacag ttaccaatgc ttaatcagtg   1920
aggcacctat ctcagcgatc tgtctatttc gttcatccat agttgcctga ctccccgtcg   1980
tgtagataac tacgatacgg gagggcttac catctggccc cagtgctgca atgataccgc   2040
gagacccacg ctcaccggct ccagatttat cagcaataaa ccagccagcc ggaagggccg   2100
agcgcagaag tggtcctgca actttatccg cctccatcca gtctattaat tgttgccggg   2160
aagctagagt aagtagttcg ccagttaata gtttgcgcaa cgttgttgcc attgctacag   2220
gcatcgtggt gtcacgctcg tcgtttggta tggcttcatt cagctccggt tcccaacgat   2280
caaggcgagt tacatgatcc cccatgttgt gcaaaaaagc ggttagctcc ttcggtcctc   2340
cgatcgttgt cagaagtaag ttggccgcag tgttatcact catggttatg gcagcactgc   2400
ataattctct tactgtcatg ccatccgtaa gatgcttttc tgtgactggt gagtactcaa   2460
ccaagtcatt ctgagaatag tgtatgcggc gaccgagttg ctcttgcccg gcgtcaatac   2520
gggataatac cgcgccacat agcagaactt taaaagtgct catcattgga aaacgttctt   2580
cggggcgaaa actctcaagg atcttaccgc tgttgagatc cagttcgatg taacccactc   2640
gtgcacccaa ctgatcttca gcatctttta ctttcaccag cgtttctggg tgagcaaaaa   2700
caggaaggca aaatgccgca aaaaagggaa taagggcgac acggaaatgt tgaatactca   2760
```

```
tactcttcct ttttcaatat tattgaagca tttatcaggg ttattgtctc atgagcggat   2820

acatatttga atgtatttag aaaaataaac aaataggggt tccgcgcaca tttccccgaa   2880

aagtgccacc tgacgtctaa gaaaccatta ttatcatgac attaacctat aaaaataggc   2940

gtatcacgag gccctttcgt ctcgcgcgtt tcggtgatga cggtgaaaac ctctgacaca   3000

tgcagctccc ggagacggtc acagcttgtc tgtaagcgga tgccgggagc agacaagccc   3060

gtcagggcgc gtcagcgggt gttggcgggt gtcggggctg gcttaactat gcggcatcag   3120

agcagattgt actgagagtg caccatatgg acatattgtc gttagaacgc ggctacaatt   3180

aatacataac cttatgtatc atacacatac gatttaggtg acactata                3228
```

<210> SEQ ID NO 5
<211> LENGTH: 7830
<212> TYPE: DNA
<213> ORGANISM: Artificial Sequence
<220> FEATURE:
<223> OTHER INFORMATION: pTM1-D1

<400> SEQUENCE: 5

```
aagcttttgc gatcaataaa tggatcacaa ccagtatctc ttaacgatgt tcttcgcaga     60

tgatgattca ttttttaagt atttggctag tcaagatgat gaatcttcat tatctgatat    120

attgcaaatc actcaatatc tagactttct gttattatta ttgatccaat caaaaaataa    180

attagaagcc gtgggtcatt gttatgaatc tctttcagag gaatacagac aattgacaaa    240

attcacagac tttcaagatt ttaaaaaact gtttaacaag gtccctattg ttacagatgg    300

aagggtcaaa cttaataaag gatatttgtt cgactttgtg attagtttga tgcgattcaa    360

aaaagaatcc tctctagcta ccaccgcaat agatcctgtt agatacatag atcctcgtcg    420

caatatcgca ttttctaacg tgatggatat attaaagtcg aataaagtga acaataatta    480

attctttatt gtcatcatga acggcggaca tattcagttg ataatcggcc ccatgttttc    540

aggtaaaagt acagaattaa ttagacgagt tagacgttat caaatagctc aatataaatg    600

cgtgactata aaatattcta acgataatag atacggaacg ggactatgga cgcatgataa    660

gaataatttt gaagcattgg aagcaactaa actatgtgat gtcttggaat caattacaga    720

tttctccgtg ataggtatcg atgaaggaca gttctttcca gacattgttg aattgatctc    780

gatcccgcga aattaatacg actcactata gggagaccac aacggtttcc ctctagcggg    840

atcaattccg cccctctccc tccccccccc ctaacgttac tggccgaagc cgcttggaat    900

aaggccggtg tgcgtttgtc tatatgttat tttccaccat attgccgtct tttggcaatg    960

tgagggcccg gaaacctggc cctgtcttct tgacgagcat tcctaggggt ctttcccctc   1020

tcgccaaagg aatgcaaggt ctgttgaatg tcgtgaagga agcagttcct ctggaagctt   1080

cttgaagaca aacaacgtct gtagcgaccc tttgcaggca gcggaacccc ccacctggcg   1140

acaggtgcct ctgcggccaa aagccacgtg tataagatac acctgcaaag gcggcacaac   1200

cccagtgcca cgttgtgagt tggatagttg tggaaagagt caaatggctc tcctcaagcg   1260

tattcaacaa ggggctgaag gatgcccaga aggtacccca ttgtatggga tctgatctgg   1320

ggcctcggtg cacatgcttt acatgtgttt agtcgaggtt aaaaaacgtc taggcccccc   1380

gaaccacggg gacgtggttt tcctttgaaa aacacgataa taccatggat gccaacgtag   1440

tatcatcttc tactattgcg acgtatatag acgctttagc gaagaatgct tcggaattag   1500

aacagaggtc taccgcatac gaaataaata atgaattgga actagtattt attaagccgc   1560

cattgattac tttgacaaat gtagtgaata tctctacgat tcaggaatcg tttattcgat   1620
```

```
ttaccgttac taataaggaa ggtgttaaaa ttagaactaa gattccatta tctaaggtac   1680
atggtctaga tgtaaaaaat gtacagttag tagatgctat agataacata gtttgggaaa   1740
agaaatcatt agtgacggaa aatcgtcttc acaaagaatg cttgttgaga ctatcgacag   1800
aggaacgtca tatattttg gattacaaga aatatggatc ctctatccga ctagaattag   1860
tcaatcttat tcaagcaaaa acaaaaaact ttacgataga ctttaagcta aaatattttc   1920
taggatccgg tgcccagtct aaaagttctt tattacacgc tattaatcat ccaaagtcaa   1980
ggcctaatac atctctggaa atagaattta cacctagaga caatgaaaca gttccatatg   2040
atgaactaat aaaggaattg acgactctct cgcgtcatat atttatggct tctccagaga   2100
atgtaattct ttctccgcct attaacgcgc ctataaaaac ctttatgttg cctaaacaag   2160
atatagtagg tttggatctg gaaaatctat atgccgtaac taagactgac ggcattccta   2220
taactatcag agttacatca aacgggttgt attgttattt tacacatctt ggttatatta   2280
ttagatatcc tgttaagaga ataatagatt ccgaagtagt agtctttggt gaggcagtta   2340
aggataagaa ctggaccgta tatctcatta agctaataga gcctgtgaat gcaatcaatg   2400
atagactaga agaaagtaag tatgttgaat ctaaactagt ggatatttgt gatcggatag   2460
tattcaagtc aaagaaatac gaaggtccgt ttactacaac tagtgaagtc gtcgatatgt   2520
tatctacata tttaccaaag caaccagaag gtgttattct gttctattca aagggaccta   2580
aatctaacat tgattttaaa attaaaaagg aaaatactat agaccaaact gcaaatgtag   2640
tatttaggta catgtccagt gaaccaatta tctttggaga gtcgtctatc tttgtagagt   2700
ataagaaatt tagcaacgat aaaggctttc ctaaagaata tggttctggt aagattgtgt   2760
tatataacgg cgttaattat ctaaataata tctattgttt ggaatatatt aatacacata   2820
atgaagtggg tattaagtcc gtggttgtac ctattaagtt tatagcagaa ttcttagtta   2880
atggagaaat acttaaacct agaattgata aaaccatgaa atatattaac tcagaagatt   2940
attatggaaa tcaacataat atcatagtcg aacatttaag agatcaaagc atcaaaatag   3000
gagatatctt taacgaggat aaactatcgg atgtgggaca tcaatacgcc aataatgata   3060
aatttagatt aaatccagaa gttagttatt ttacgaataa acgaactaga ggaccgttgg   3120
gaattttatc aaactacgtc aagactcttc ttatttctat gtattgttcc aaaacatttt   3180
tagacgattc caacaaacga aaggtattgg cgattgattt tggaaacggt gctgacctgg   3240
aaaaatactt ttatggagag attgcgttat tggtagcgac ggatccggat gctgatgcta   3300
tagctagagg aaatgaaaga tacaacaaat taaactctgg aattaaaacc aagtactaca   3360
aatttgacta cattcaggaa actattcgat ccgatacatt tgtctctagt gtcagagaag   3420
tattctattt tggaaagttt aatatcatcg actggcagtt tgctatccat tattcttttc   3480
atccgagaca ttatgctacc gtcatgaata acttatccga actaactgct tctggaggca   3540
aggtattaat cactaccatg gacggagaca aattatcaaa attaacagat aaaaagactt   3600
ttataattca taagaattta cctagtagcg aaaactatat gtctgtagaa aaaatagctg   3660
atgatagaat agtggtatat aatccatcaa caatgtctac tccaatgact gaatacatta   3720
tcaaaaagaa cgatatagtc agagtgttta acgaatacgg atttgttctt gtagataacg   3780
ttgatttcgc tacaattata gaacgaagta aaaagtttat taatggcgca tctacaatgg   3840
aagatagacc atctacaaga aactttttcg aactaaatag aggagccatt aaatgtgaag   3900
gtttagatgt cgaagactta cttagttact atgttgttta tgtcttttct aagcggtaag   3960
tcgacgatcc ggctgctaac aaagcccgaa aggaagctga gttggctgct gccaccgctg   4020
```

-continued

```
agcaataact agcataaccc cttggggcct ctaaacgggt cttgaggggt tttttgctga   4080
aaggaggaac tatatccgga tcgagatcaa ttctgtgagc gtatggcaaa cgaaggaaaa   4140
atagttatag tagccgcact cgatgggaca tttcaacgta aaccgtttaa taatattttg   4200
aatcttattc cattatctga aatggtggta aaactaactg ctgtgtgtat gaaatgcttt   4260
aaggaggctt ccttttctaa acgattgggt gaggaaaccg agatagaaat aataggaggt   4320
aatgatatgt atcaatcggt gtgtagaaag tgttacatcg actcataata ttatattttt   4380
tatctaaaaa actaaaaata aacattgatt aaattttaat ataatactta aaaatggatg   4440
ttgtgtcgtt agataaaccg tttatgtatt ttgaggaaat tgataatgag ttagattacg   4500
aaccagaaag tgcaaatgag gtcgcaaaaa aactgccgta tcaaggacag ttaaaactat   4560
tactaggaga attatttttt cttagtaagt tacagcgaca cggtatatta gatggtgcca   4620
ccgtagtgta tataggatct gctcccggta cacatatacg ttatttgaga gatcatttct   4680
ataatttagg agtgatcatc aaatggatgc taattgacgg ccgccatcat gatcctattt   4740
taaatggatt gcgtgatgtg actctagtga ctcggttcgt tgatgaggaa tatctacgat   4800
ccatcaaaaa acaactgcat ccttctaaga ttattttaat ttctgatgtg agatccaaac   4860
gaggaggaaa tgaacctagt acggcggatt tactaagtaa ttacgctcta caaaatgtca   4920
tgattagtat tttaaacccc gtggcgtcta gtcttaaatg gagatgcccg tttccagatc   4980
aatggatcaa ggacttttat atcccacacg gtaataaaat gttacaacct tttgctcctt   5040
catattcagg gccgtcgttt tacaacgtcg tgactgggaa aaccctggcg ttacccaact   5100
taatcgcctt gcagcacatc ccccttcgc cagctggcgt aatagcgaag aggcccgcac   5160
cgatcgccct tcccaacagt tgcgcagcct gaatggcgaa tggcgcgacg cgccctgtag   5220
cggcgcatta agcgcggcgg gtgtggtggt tacgcgcagc gtgaccgcta cacttgccag   5280
cgccctagcg cccgctcctt tcgctttctt cccttccttt ctcgccacgt tcgccggctt   5340
tccccgtcaa gctctaaatc gggggctccc tttagggttc cgatttagtg ctttacggca   5400
cctcgacccc aaaaaacttg attagggtga tggttcacgt agtgggccat cgccctgata   5460
gacggttttt cgccctttga cgttggagtc cacgttcttt aatagtggac tcttgttcca   5520
aactggaaca acactcaacc ctatctcggt ctattctttt gatttataag ggattttgcc   5580
gatttcggcc tattggttaa aaaatgagct gatttaacaa aaatttaacg cgaattttaa   5640
caaaatatta acgtttacaa tttcccaggt ggcacttttc ggggaaatgt gcgcggaacc   5700
cctatttgtt tatttttcta aatacattca aatatgtatc cgctcatgag acaataaccc   5760
tgataaatgc ttcaataata ttgaaaaagg aagagtatga gtattcaaca tttccgtgtc   5820
gcccttattc ccttttttgc ggcattttgc cttcctgttt ttgctcaccc agaaacgctg   5880
gtgaaagtaa aagatgctga agatcagttg ggtgcacgag tgggttacat cgaactggat   5940
ctcaacagcg gtaagatcct tgagagtttt cgccccgaag aacgttttcc aatgatgagc   6000
acttttaaag ttctgctatg tggcgcggta ttatcccgta ttgacgccgg gcaagagcaa   6060
ctcggtcgcc gcatacacta ttctcagaat gacttggttg agtactcacc agtcacagaa   6120
aagcatctta cggatggcat gacagtaaga gaattatgca gtgctgccat aaccatgagt   6180
gataacactg cggccaactt acttctgaca acgatcggag gaccgaagga gctaaccgct   6240
tttttgcaca acatgggggga tcatgtaact cgccttgatc gttgggaacc ggagctgaat   6300
gaagccatac caaacgacga gcgtgacacc acgatgcctg tagcaatggc aacaacgttg   6360
cgcaaactat taactggcga actacttact ctagcttccc ggcaacaatt aatagactgg   6420
```

```
atggaggcgg ataaagttgc aggaccactt ctgcgctcgg cccttccggc tggctggttt   6480

attgctgata aatctggagc cggtgagcgt gggtctcgcg gtatcattgc agcactgggg   6540

ccagatggta agccctcccg tatcgtagtt atctacacga cggggagtca ggcaactatg   6600

gatgaacgaa atagacagat cgctgagata ggtgcctcac tgattaagca ttggtaactg   6660

tcagaccaag tttactcata tatactttag attgatttaa aacttcattt ttaatttaaa   6720

aggatctagg tgaagatcct ttttgataat ctcatgacca aaatccctta acgtgagttt   6780

tcgttccact gagcgtcaga ccccgtagaa aagatcaaag gatcttcttg agatcctttt   6840

tttctgcgcg taatctgctg cttgcaaaca aaaaaaccac cgctaccagc ggtggtttgt   6900

ttgccggatc aagagctacc aactcttttt ccgaaggtaa ctggcttcag cagagcgcag   6960

ataccaaata ctgtccttct agtgtagccg tagttaggcc accacttcaa gaactctgta   7020

gcaccgccta catacctcgc tctgctaatc ctgttaccag tggctgctgc cagtggcgat   7080

aagtcgtgtc ttaccgggtt ggactcaaga cgatagttac cggataaggc gcagcggtcg   7140

ggctgaacgg ggggttcgtg cacacagccc agcttggagc gaacgaccta caccgaactg   7200

agatacctac agcgtgagct atgagaaagc gccacgcttc ccgaagggag aaaggcggac   7260

aggtatccgg taagcggcag ggtcggaaca ggagagcgca cgagggagct tccaggggga   7320

aacgcctggt atctttatag tcctgtcggg tttcgccacc tctgacttga gcgtcgattt   7380

ttgtgatgct cgtcaggggg gcggagccta tggaaaaacg ccagcaacgc ggccttttta   7440

cggttcctgg ccttttgctg gccttttgct cacatgttct ttcctgcgtt atcccctgat   7500

tctgtggata accgtattac cgcctttgag tgagctgata ccgctcgccg cagccgaacg   7560

accgagcgca gcgagtcagt gagcgaggaa gcggaagagc gcccaatacg caaaccgcct   7620

ctccccgcgc gttggccgat tcattaatgc agctggcacg acaggtttcc cgactggaaa   7680

gcgggcagtg agcgcaacgc aattaatgtg agttagctca ctcattaggc accccaggct   7740

ttacacttta tgcttccggc tcgtatgttg tgtggaattg tgagcggata acaatttcac   7800

acaggaaaca gctatgacca tgattacgcc                                    7830
```

```
<210> SEQ ID NO 6
<211> LENGTH: 6193
<212> TYPE: DNA
<213> ORGANISM: Artificial Sequence
<220> FEATURE:
<223> OTHER INFORMATION: pTM1-D12

<400> SEQUENCE: 6

aagcttttgc gatcaataaa tggatcacaa ccagtatctc ttaacgatgt tcttcgcaga     60

tgatgattca ttttttaagt atttggctag tcaagatgat gaatcttcat tatctgatat    120

attgcaaatc actcaatatc tagactttct gttattatta ttgatccaat caaaaaataa    180

attagaagcc gtgggtcatt gttatgaatc tctttcagag gaatacagac aattgacaaa    240

attcacagac tttcaagatt ttaaaaaact gtttaacaag gtccctattg ttacagatgg    300

aagggtcaaa cttaataaag gatatttgtt cgactttgtg attagtttga tgcgattcaa    360

aaaagaatcc tctctagcta ccaccgcaat agatcctgtt agatacatag atcctcgtcg    420

caatatcgca ttttctaacg tgatggatat attaaagtcg aataaagtga acaataatta    480

attctttatt gtcatcatga acggcggaca tattcagttg ataatcggcc ccatgttttc    540

aggtaaaagt acagaattaa ttagacgagt tagacgttat caaatagctc aatataaatg    600

cgtgactata aaatattcta acgataatag atacggaacg ggactatgga cgcatgataa    660
```

```
gaataatttt gaagcattgg aagcaactaa actatgtgat gtcttggaat caattacaga    720
tttctccgtg ataggtatcg atgaaggaca gttctttcca gacattgttg aattgatctc    780
gatcccgcga aattaatacg actcactata gggagaccac aacggtttcc ctctagcggg    840
atcaattccg cccctctccc tccccccccc ctaacgttac tggccgaagc cgcttggaat    900
aaggccggtg tgcgtttgtc tatatgttat tttccaccat attgccgtct tttggcaatg    960
tgagggcccg gaaacctggc cctgtcttct tgacgagcat tcctaggggt ctttcccctc   1020
tcgccaaagg aatgcaaggt ctgttgaatg tcgtgaagga agcagttcct ctggaagctt   1080
cttgaagaca aacaacgtct gtagcgaccc tttgcaggca gcggaacccc ccacctggcg   1140
acaggtgcct ctgcggccaa aagccacgtg tataagatac acctgcaaag gcggcacaac   1200
cccagtgcca cgttgtgagt tggatagttg tggaaagagt caaatggctc tcctcaagcg   1260
tattcaacaa ggggctgaag gatgcccaga aggtacccca ttgtatggga tctgatctgg   1320
ggcctcggtg cacatgcttt acatgtgttt agtcgaggtt aaaaaacgtc taggcccccc   1380
gaaccacggg gacgtggttt tcctttgaaa aacacgataa taccatggat gaaattgtaa   1440
aaaatatccg ggagggaacg catgtccttc ttccatttta tgaaacattg ccagaactta   1500
atctgtctct aggtaaaagc ccattaccta gtctggaata cggagctaat tactttcttc   1560
agatttctag agttaatgat ctaaatagaa tgccgaccga catgttaaaa ctttttacac   1620
atgatatcat gttaccagaa agcgatctag ataaagtcta tgaaatttta aagattaata   1680
gcgtaaagta ttatgggagg agtactaaag cggacgccgt agttgccgac ctcagcgcac   1740
gcaataaact gttcaaacgt gaacgagatg ctattaaatc taataatcat ctcactgaaa   1800
acaatctata cattagcgat tataagatgt taaccttcga cgtgtttcga ccattatttg   1860
attttgtaaa cgaaaaatat tgtattatta aacttccaac tttattcggt agaggtgtaa   1920
tcgatactat gagaatatat tgtagtctct ttaaaaatgt tagactgcta aaatgcgtaa   1980
gcgatagctg gttaaaagat agcgccatta tggtggctag tgatgtttgt aaaaaaaatt   2040
tggatttatt tatgtctcat gttaagtccg tcactaagtc ttcttcttgg aaggatgtga   2100
acagtgttca atttagtatt ttaaacaatc cagtggatac ggaattcatt aataagttct   2160
tagagttttc gaatagagta tacgaagctc tctattacgt tcactcgttg ctttattcta   2220
gtatgacttc tgattcaaaa agtatcgaaa acaaacatca gagaagacta gttaaactac   2280
tgctgtgagg atccctgcag ctcgagaggc ctaattaatt aagtcgacga tccggctgct   2340
aacaaagccc gaaaggaagc tgagttggct gctgccaccg ctgagcaata actagcataa   2400
ccccttgggg cctctaaacg ggtcttgagg ggttttttgc tgaaaggagg aactatatcc   2460
ggatcgagat caattctgtg agcgtatggc aaacgaagga aaaatagtta tagtagccgc   2520
actcgatggg acatttcaac gtaaaccgtt taataatatt ttgaatctta ttccattatc   2580
tgaaatggtg gtaaaactaa ctgctgtgtg tatgaaatgc tttaaggagg cttccttttc   2640
taaacgattg ggtgaggaaa ccgagataga aataatagga ggtaatgata tgtatcaatc   2700
ggtgtgtaga aagtgttaca tcgactcata atattatatt ttttatctaa aaaactaaaa   2760
ataaacattg attaaatttt aatataatac ttaaaaatgg atgttgtgtc gttagataaa   2820
ccgtttatgt attttgagga aattgataat gagttagatt acgaaccaga aagtgcaaat   2880
gaggtcgcaa aaaaactgcc gtatcaagga cagttaaaac tattactagg agaattattt   2940
tttcttagta agttacagcg acacggtata ttagatggtg ccaccgtagt gtatatagga   3000
tctgctcccg gtacacatat acgttatttg agagatcatt tctataattt aggagtgatc   3060
```

-continued

```
atcaaatgga tgctaattga cggccgccat catgatccta ttttaaatgg attgcgtgat   3120

gtgactctag tgactcggtt cgttgatgag gaatatctac gatccatcaa aaaacaactg   3180

catccttcta agattatttt aatttctgat gtgagatcca aacgaggagg aaatgaacct   3240

agtacggcgg atttactaag taattacgct ctacaaaatg tcatgattag tattttaaac   3300

cccgtggcgt ctagtcttaa atggagatgc ccgtttccag atcaatggat caaggacttt   3360

tatatcccac acggtaataa aatgttacaa ccttttgctc cttcatattc agggccgtcg   3420

ttttacaacg tcgtgactgg gaaaaccctg gcgttaccca acttaatcgc cttgcagcac   3480

atccccctttt cgccagctgg cgtaatagcg aagaggcccg caccgatcgc ccttcccaac   3540

agttgcgcag cctgaatggc gaatggcgcg acgcgccctg tagcggcgca ttaagcgcgg   3600

cgggtgtggt ggttacgcgc agcgtgaccg ctacacttgc cagcgcccta gcgcccgctc   3660

ctttcgcttt cttcccttcc tttctcgcca cgttcgccgg ctttccccgt caagctctaa   3720

atcgggggct ccctttaggg ttccgattta gtgctttacg gcacctcgac cccaaaaaac   3780

ttgattaggg tgatggttca cgtagtgggc catcgccctg atagacggtt tttcgccctt   3840

tgacgttgga gtccacgttc tttaatagtg gactcttgtt ccaaactgga acaacactca   3900

accctatctc ggtctattct tttgatttat aagggatttt gccgatttcg gcctattggt   3960

taaaaaatga gctgatttaa caaaaattta acgcgaattt taacaaaata ttaacgttta   4020

caatttccca ggtggcactt ttcggggaaa tgtgcgcgga acccctattt gtttattttt   4080

ctaaatacat tcaaatatgt atccgctcat gagacaataa ccctgataaa tgcttcaata   4140

atattgaaaa aggaagagta tgagtattca acatttccgt gtcgccctta ttcccttttt   4200

tgcggcattt tgccttcctg tttttgctca cccagaaacg ctggtgaaag taaaagatgc   4260

tgaagatcag ttgggtgcac gagtgggtta catcgaactg gatctcaaca gcggtaagat   4320

ccttgagagt tttcgccccg aagaacgttt tccaatgatg agcactttta aagttctgct   4380

atgtggcgcg gtattatccc gtattgacgc cgggcaagag caactcggtc gccgcataca   4440

ctattctcag aatgacttgg ttgagtactc accagtcaca gaaaagcatc ttacggatgg   4500

catgacagta agagaattat gcagtgctgc cataaccatg agtgataaca ctgcggccaa   4560

cttacttctg acaacgatcg gaggaccgaa ggagctaacc gcttttttgc acaacatggg   4620

ggatcatgta actcgccttg atcgttggga accggagctg aatgaagcca taccaaacga   4680

cgagcgtgac accacgatgc ctgtagcaat ggcaacaacg ttgcgcaaac tattaactgg   4740

cgaactactt actctagctt cccggcaaca attaatagac tggatggagg cggataaagt   4800

tgcaggacca cttctgcgct cggcccttcc ggctggctgg tttattgctg ataaatctgg   4860

agccggtgag cgtgggtctc gcggtatcat tgcagcactg gggccagatg gtaagccctc   4920

ccgtatcgta gttatctaca cgacggggag tcaggcaact atggatgaac gaaatagaca   4980

gatcgctgag ataggtgcct cactgattaa gcattggtaa ctgtcagacc aagtttactc   5040

atatatactt tagattgatt taaaacttca tttttaattt aaaaggatct aggtgaagat   5100

cctttttgat aatctcatga ccaaaatccc ttaacgtgag ttttcgttcc actgagcgtc   5160

agaccccgta gaaaagatca aaggatcttc ttgagatcct ttttttctgc gcgtaatctg   5220

ctgcttgcaa acaaaaaaac caccgctacc agcggtggtt tgtttgccgg atcaagagct   5280

accaactctt tttccgaagg taactggctt cagcagagcg cagataccaa atactgtcct   5340

tctagtgtag ccgtagttag gccaccactt caagaactct gtagcaccgc ctacatacct   5400

cgctctgcta atcctgttac cagtggctgc tgccagtggc gataagtcgt gtcttaccgg   5460
```

-continued

```
gttggactca agacgatagt taccggataa ggcgcagcgg tcgggctgaa cggggggttc   5520

gtgcacacag cccagcttgg agcgaacgac ctacaccgaa ctgagatacc tacagcgtga   5580

gctatgagaa agcgccacgc ttcccgaagg gagaaaggcg gacaggtatc cggtaagcgg   5640

cagggtcgga acaggagagc gcacgaggga gcttccaggg ggaaacgcct ggtatcttta   5700

tagtcctgtc gggtttcgcc acctctgact tgagcgtcga tttttgtgat gctcgtcagg   5760

ggggcggagc ctatggaaaa acgccagcaa cgcggccttt ttacggttcc tggccttttg   5820

ctggcctttt gctcacatgt tctttcctgc gttatcccct gattctgtgg ataaccgtat   5880

taccgccttt gagtgagctg ataccgctcg ccgcagccga acgaccgagc gcagcgagtc   5940

agtgagcgag gaagcggaag agcgcccaat acgcaaaccg cctctccccg cgcgttggcc   6000

gattcattaa tgcagctggc acgacaggtt tcccgactgg aaagcgggca gtgagcgcaa   6060

cgcaattaat gtgagttagc tcactcatta ggcaccccag gctttacact ttatgcttcc   6120

ggctcgtatg ttgtgtggaa ttgtgagcgg ataacaattt cacacaggaa acagctatga   6180

ccatgattac gcc                                                      6193
```

EXPRESSION SYSTEM

CROSS-REFERENCE TO RELATED APPLICATIONS

This application is a divisional of U.S. application Ser. No. 11/628,374, filed Oct. 17, 2007, which is a National Stage application under 35 U.S.C. §371 of International Application. No. PCT/US2005/019371, filed Jun. 1, 2005, which claims benefit of priority from U.S. Provisional Application Ser. No. 60/576,169, filed Jun. 1, 2004. The disclosures of the prior applications are considered part of (and are incorporated by reference in) the disclosure of this application.

TECHNICAL FIELD

The present invention relates generally to methods and compositions for a novel expression system. The system may be used for the expression of polypeptides in various cell types or to deliver interfering RNAs.

BACKGROUND

DNA cloning technology provides a readily amplifiable source of genes encoding any protein of interest. When the recombinant protein itself is needed, genes are cloned in expression vectors that are introduced into appropriate cell types where protein synthesis can take place. To produce large amounts of these proteins, two general types of transient gene expression vectors have been used: plasmid DNA vectors which are introduced directly into cells and viral vectors that express foreign genes as part of their genetic material. The latter type of vector is generally more efficient in higher eukaryotic cells because all cells can be infected simultaneously and many viruses can express proteins at very high levels. Plasmid vector preparation is less labor intensive but DNA transfection can be inherently less efficient and amounts of protein synthesized are generally lower.

High-level recombinant protein expression is crucial for the biopharmaceutical industry as well as for basic research. Large amounts of specific proteins are very often required for general biochemical characterization, structural studies, drug discovery development, gene therapy, subunit vaccine production, and reagent use. Different uses dictate which particular protein expression system provides the best combination of properties. For example, high-level transient protein expression in mammalian cells most often makes use of viral vectors (e.g., adenovirus, baculovirus, poxvirus, alphavirus). In most applications, the gene of interest is cloned into the virus genome or a derivative replicon which is labor intensive and time consuming. Plasmid vectors are also used for transient protein expression but efficiency is generally much lower. Another method employs recombinant viruses that express the T7 RNA polymerase to drive expression of desired proteins from plasmids under control of a T7 promoter. This latter approach is very efficient using a vaccinia-T7 recombinant virus especially when incorporating an internal ribosome entry sequence (IRES) in the T7 transcript. However, high level protein production using the vaccinia-T7 system is limited to host cells that grow the virus efficiently. Moreover, the use of an infectious virus related to the smallpox vaccine strain raises biosafety concerns.

In the last few years, advances in nucleic acid chemistry and gene transfer have inspired new approaches to engineer specific interference with gene expression. Antisense technology has been the most commonly described approach in protocols to achieve gene-specific interference. For antisense strategies, stoichiometric amounts of single-stranded nucleic acid complementary to the messenger RNA for the gene of interest are introduced into the cell. Some difficulties with antisense-based approaches relate to delivery, stability, and dose requirements. In general, cells do not have an uptake mechanism for single-stranded nucleic acids, hence uptake of unmodified single-stranded material is extremely inefficient. While waiting for uptake into cells, the single-stranded material is subject to degradation. Because antisense interference requires that the interfering material accumulate at a relatively high concentration (at or above the concentration of endogenous mRNA), the amount required to be delivered is a major constraint on efficacy. As a consequence, much of the effort in developing antisense technology has been focused on the production of modified nucleic acids that are both stable to nuclease digestion and able to diffuse readily into cells.

Double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis. Recent work suggests that RNA fragments are the sequence-specific mediators of RNAi (Elbashir et al., Nature 2001 411:494; Elbashir et al., Genes and Development 2001, 15:188). Interference of gene expression by these small interfering RNA (siRNA) is now recognized as a naturally occurring strategy for silencing genes in *C. elegans, Drosophila*, plants, and in mouse embryonic stem cells, oocytes and early embryos (Cogoni et al., Antonie Van Leeuwenhoek 1994, 65:205; Baulcombe, Plant Mol. Biol., 1996, 32:79; Kennerdell and Carthew, Cell 1998, 95:1017; Timmons and Fire, Nature 1998, 395:854; Waterhouse et al., Proc. Natl. Acad. Sci. U.S.A. 1998, 95:13959; Wianny and Zernicka-Goetz, Nat. Cell Biol. 2000, 2:70; Yang et al., Mol. Cell Biol. 2001, 21:7807; Svoboda et al., Development 2000, 127:4147 (2000). In mammalian cell culture, a siRNA-mediated reduction in gene expression has been accomplished by transfecting cells with synthetic RNA oligonucleotides (Caplan et al., Proc. Natl. Acad. Sci. U.S.A. 2001, 98:9742; Elbashir et al., 2001, supra). However, as Bass (Nature 2001, 411:428) notes, various issues regarding the use of siRNA in mammalian cells have yet to be addressed, including effective delivery of siRNA to mammalian cells in vivo. Furthermore, if siRNA is to be utilized in in vivo therapy, it will be important in many cases to develop methods to express siRNA in tissues in vivo to achieve extended intracellular transcription of the siRNA.

Vesicular stomatitis virus (VSV), of the genus, *Vesiculovirus*, is the prototypic member of the family Rhabdoviridae, and is an enveloped virus with a negative stranded RNA genome that causes a self-limiting disease in live-stock and is essentially non-pathogenic in humans. Balachandran and Barber (2000, IUBMB Life 50: 135-8). Rhabdoviruses have single, negative-strand RNA genomes of 11,000 to 12,000 nucleotides (Rose and Schubert, 1987, Rhabdovirus genomes and their products, in The Viruses: The Rhabdoviruses, Plenum Publishing Corp., NY, pp. 129-166). The virus particles contain a helical, nucleocapsid core composed of the genomic RNA and protein. Generally, three proteins, termed N (nucleocapsid, which encases the genome tightly), P (formerly termed NS, originally indicating nonstructural), and L (large) are found to be associated with the nucleocapsid. An additional matrix (M) protein lies within the membrane envelope, perhaps interacting both with the membrane and the nucleocapsid core. A single glycoprotein (G) species spans the membrane and forms the spikes on the surface of the virus particle. Glycoprotein G is responsible for binding to cells and membrane fusion. The VSV genome is the negative sense (i.e., complementary to the RNA sequence (positive sense) that functions as mRNA to directly produce encoded protein), and rhabdoviruses must encode and package an RNA-dependent RNA polymerase in the virion (Baltimore et al., 1970, Proc. Natl. Acad. Sci. USA 66: 572-576), composed of the P and L proteins. This enzyme transcribes genomic RNA to make subgenomic mRNAs encoding the 5-6 viral proteins and also replicates full-length positive and negative sense RNAs. The genes are transcribed sequentially, starting at the 3' end of the genomes.

VSV replicates rapidly (<12 hours) and very efficiently in the cytoplasm of almost all vertebrate cells and produces very high levels of infectious virus (titers approaching 20,000 infectious units/cell in some cases) and can also infect insect cells. The sequences of the VSV mRNAs and genome are described in Gallione et al. 1981, R Virol. 39: 529-535; Rose and Gallione, 1981, J. Virol. 39: 519-528; Rose and Schubert, 1987; Rhabdovirus genomes and their products, p. 129-166, in R. R. Wagner (ed.); The Rhabdoviruses, Plenum Publishing Corp., NY; Schubert et al., 1985, Proc. Natl. Acad. Sci. USA 82: 7984-7988). WO96/34625 published Nov. 7, 1996, disclose methods for the production and recovery of replicable vesiculovirus. U.S. Pat. No. 6,168,943, issued Jan. 2, 2001, describe methods for making recombinant vesiculoviruses.

Growth in tissue culture and purification of virus is relatively simple and methods for engineering mutations or additional genes in the virus genome, while retaining very high infectivity, are well established. It is moreover possible to engineer the surface protein of the virus and target infection to specific cell types. Natural hosts include cattle, horses, and pigs where it causes a non-fatal but debilitating disease. Laboratory strains pose very little if any risk of pathogenicity in humans. VSV is currently being explored as a vector for vaccine production, gene replacement therapy, and anticancer therapy.

Expression of the T7 RNA polymerase enzyme by recombinant viruses has been reported (see e.g. Mohammed et al., *Methods Mol Biol.* 2004; 269:41-50; and Eckert et al., J Gen Virol. 1999 June; 80 (Pt 6):1463-9). Recombinant T7-expressing viruses are capable of driving transient expression of proteins from plasmids. The best characterized of these systems is the recombinant vaccinia-T7 virus which yields very high levels or protein. The limitations and uses of any of the virus-T7 expression systems are in large part governed by the properties of the virus. Thus, there is a need for a safe and efficient alternative virus-T7 polypeptide expression system.

SUMMARY

Expression systems comprising a combination of a virus vector and a plasmid that leads to very high transient expression of polynucleotides and polypeptides are provided. The system may also be used to deliver interfering RNAs. Methods for making and using the system are also provided. Vesicular stomatitis virus was engineered to express the prokaryotic T7 RNA polymerase enzyme in the cytoplasm of infected cells. Infected cells were then transfected with a plasmid DNA encoding a gene of interest downstream of a T7 promoter sequence and an internal ribosome entry sequence. This results in cytoplasmic accumulation of large amounts of T7 mRNA transcripts which are efficiently translated into the desired protein. Methods and compositions are also provided bypassing the need for an internal ribosome entry sequence in the transfected plasmid. Provided herein are compositions and methods for a recombinant vesicular stomatitis virus vector expression system. A vesicular stomatitis virus vector particle (VSV) encoding a T7 RNA polymerase is provided and used to infect a cell, such that the T7 polymerase is expressed in the cell. Also provided is a recombinant plasmid vector encoding a heterologous gene under control of a T7 promoter and also encoding an IRES element. Cells infected with VSV-T7 viral particles are subsequently transfected with the recombinant plasmid vector such that a polynucleotide is expressed from the transcripts encoded by the heterologous gene in the cell. A method for producing a polypeptide by contacting cells with the recombinant vesicular stomatitis virus vector expression system is also provided. In one embodiment, the VSV-T7 viral particles include the sequences of polynucleotides as set forth in SEQ ID NO:1. In another embodiment, the M and G genes of the VSV-T7 vector virus vector particle are deleted or mutated such that the virus vector particle is replication-deficient. A recombinant plasmid vector consisting essentially of the polynucleotide sequence as set forth in SEQ ID NO:3 are also provided.

In one aspect, the invention provides a recombinant vesicular stomatitis virus vector expression system comprising:

(a) a vesicular stomatitis virus vector particle (VSV) comprising a polynucleotide encoding a T7 RNA polymerase, the vector particle being used to infect a cell, such that the T7 polymerase is expressed in the cell; and (b) a recombinant plasmid vector comprising a polynucleotide comprising the following elements operably linked 5' to 3':

(i) a bacteriophage promoter, and (ii) a heterologous gene, wherein the heterologous gene comprises a sequence encoding an internal ribosome entry site (IRES), the recombinant plasmid vector being used to transfect said cell so that a polypeptide is expressed from transcripts encoded by said heterologous gene in the cell. The promoter may be a T7 promoter. A method for producing a polypeptide comprising contacting cells with this recombinant vesicular stomatitis virus vector expression system is also provided.

The vesicular stomatitis virus vector particle may comprise the polynucleotide sequence in SEQ ID NO:1, and the M and G genes of the virus vector particle may be deleted or mutated such that the virus vector particle is replication-deficient. The recombinant plasmid vector may comprise a T7 promoter as set forth in SEQ ID NO:3 corresponding to nucleotide positions 794 to 813, and a heterologous gene.

In another aspect, the invention provides a recombinant vesicular stomatitis virus vector expression system comprising:

(a) a vesicular stomatitis virus vector particle (VSV) comprising a polynucleotide encoding a T7 RNA polymerase, the vector particle being used to infect a cell, such that the T7 polymerase is expressed in the cell;

(b) a first recombinant plasmid vector comprising a polynucleotide comprising the following elements operably linked 5' to 3':

(i) a bacteriophage promoter, and (ii) a heterologous gene, the recombinant plasmid vector being used to transfect said cell so that a polypeptide is expressed from transcripts encoded by said heterologous gene in the cell;

(c) a second recombinant plasmid vector comprising the D1 catalytic subunit of vaccinia capping enzyme (D1) as set forth in SEQ ID NO:5; and (d) a third recombinant plasmid vector comprising the D12 subunit of vaccinia capping enzyme (D12) as set forth in SEQ ID NO:6. The promoter may be a T7 promoter. A method for producing a polypeptide comprising contacting cells with this recombinant vesicular stomatitis virus vector expression system is also provided.

The first recombinant plasmid vector may comprise a T7 promoter as set forth in SEQ ID NO:3 corresponding to nucleotide positions 794 to 813, and a heterologous gene, and wherein the IRES polynucleotide encoding sequences are deleted. The vesicular stomatitis virus vector particle may comprise the polynucleotide sequence in SEQ ID NO:1 and the M and G genes of the virus vector particle are deleted or mutated such that the virus vector particle is replication-deficient. The second and third recombinant plasmid vectors may encode the sequences for D1 and D12 catalytic subunits of vaccinia virus-capping enzyme as set forth in SEQ ID NOS:5 and 6.

In yet another aspect, the invention provides a method of producing a vesicular stomatitis virus vector particle, said method comprising:

(a) transfecting a permissive producer cell with a vector comprising a nucleic sequence of at least part of the VSV genome and T7 RNA polymerase; and (b) growing said producer cell under cell culture conditions sufficient to allow producing of vesicular stomatitis virus vector particles in said cell; and (c) collecting said particles from said producer cell. The producer cell may be grown in cell culture medium, and the vector particles may be collected from the medium.

In yet a further aspect, a method for producing replication-defective vesicular stomatitis virus vector particles said method comprising:

(a) transfecting a permissive producer cell with a vector comprising a nucleic acid sequence of at least part of the VSV genome and T7 RNA polymerase wherein the M and G genes are deleted; and (b) growing said producer cell under cell culture conditions sufficient to allow producing of vesicular stomatitis virus vector particles in said cell; and (c) co-transfecting said cell with plasmids encoding M and G genes; and (d) collecting said particles from said producer cell. The producer cell may be grown in cell culture medium, and the replication-defective vector particles may be collected from said medium.

In a still further aspect, the invention provides recombinant vesicular stomatitis virus vector expression system comprising:

(a) a vesicular stomatitis virus vector particle (VSV) comprising a polynucleotide encoding a T7 RNA polymerase, the vector particle being used to infect a cell, such that the T7 polymerase is expressed in the cell; and (b) a recombinant plasmid vector comprising a polynucleotide comprising the following elements operably linked 5' to 3':

(i) a bacteriophage promoter, and (ii) a heterologous gene, wherein the heterologous gene comprises a sequence encoding an internal ribosome entry site (IRES), the recombinant plasmid vector being used to transfect said cell so that an interfering RNA polynucleotide is expressed from said heterologous gene in the cell. The promoter may be a T7 promoter. A method for delivering an interfering RNA polynucleotide into target cells comprising contacting cells with this recombinant vesicular stomatitis virus vector expression system is also provided.

The vesicular stomatitis virus vector particle may comprise the polynucleotide sequence in SEQ ID NO:1, and the M and G genes of the virus vector particle are deleted or mutated such that the virus vector particle is replication-deficient. The recombinant plasmid vector may comprise a T7 promoter as set forth in SEQ ID NO:3 corresponding to nucleotide positions 794 to 813, and a heterologous gene.

Another aspect of the invention provides a recombinant vesicular stomatitis virus vector expression system comprising:

(a) a vesicular stomatitis virus vector particle (VSV) comprising a polynucleotide encoding a T7 RNA polymerase, the vector particle being used to infect a cell, such that the T7 polymerase is expressed in the cell;

(b) a first recombinant plasmid vector comprising a polynucleotide comprising the following elements operably linked 5' to 3':

(i) a bacteriophage promoter, and (ii) a heterologous gene, the recombinant plasmid vector being used to transfect said cell so that an interfering RNA polynucleotide is expressed from said heterologous gene in the cell;

(c) a second recombinant plasmid vector comprising the D1 catalytic subunit of vaccinia capping enzyme (D1) as set forth in SEQ ID NO:5; and (d) a third recombinant plasmid vector comprising the D12 subunit of vaccinia capping enzyme (D12) as set forth in SEQ ID NO:6. The promoter may be a T7 promoter. A method for delivering an interfering RNA polynucleotide into target cells comprising contacting cells with this recombinant vesicular stomatitis virus vector expression system is also provided.

The first recombinant plasmid vector may comprise a T7 promoter as set forth in SEQ ID NO:3 corresponding to nucleotide positions 794 to 813, and a heterologous gene, and wherein the IRES polynucleotide encoding sequences are deleted. The vesicular stomatitis virus vector particle may comprise the polynucleotide sequence in SEQ ID NO:1, and the M and G genes of the virus vector particle are deleted or mutated such that the virus vector particle is replication-deficient. The second and third recombinant plasmid vectors may encode the sequences for D1 and D12 catalytic subunits of vaccinia virus-capping enzyme as set forth in SEQ ID NOS:5 and 6.

The invention also provides any of the above methods for expressing proteins or delivering interfereing RNA wherein the cells are transfected with said recombinant plasmid vectors by a suitable method such as liposome mediated transfer, lipofection, polycation-mediated transfer, or direct DNA transfer or uptake. The expression of a gene product in a cell may be reduced as a result of expression of an interfering RNA polynucleotide.

The details of one or more embodiments of the invention are set forth in the accompanying drawings and the description below. Other features, objects, and advantages of the invention will be apparent from the description and drawings, and from the claims.

DETAILED DESCRIPTION

A. Definitions

Figure 1:
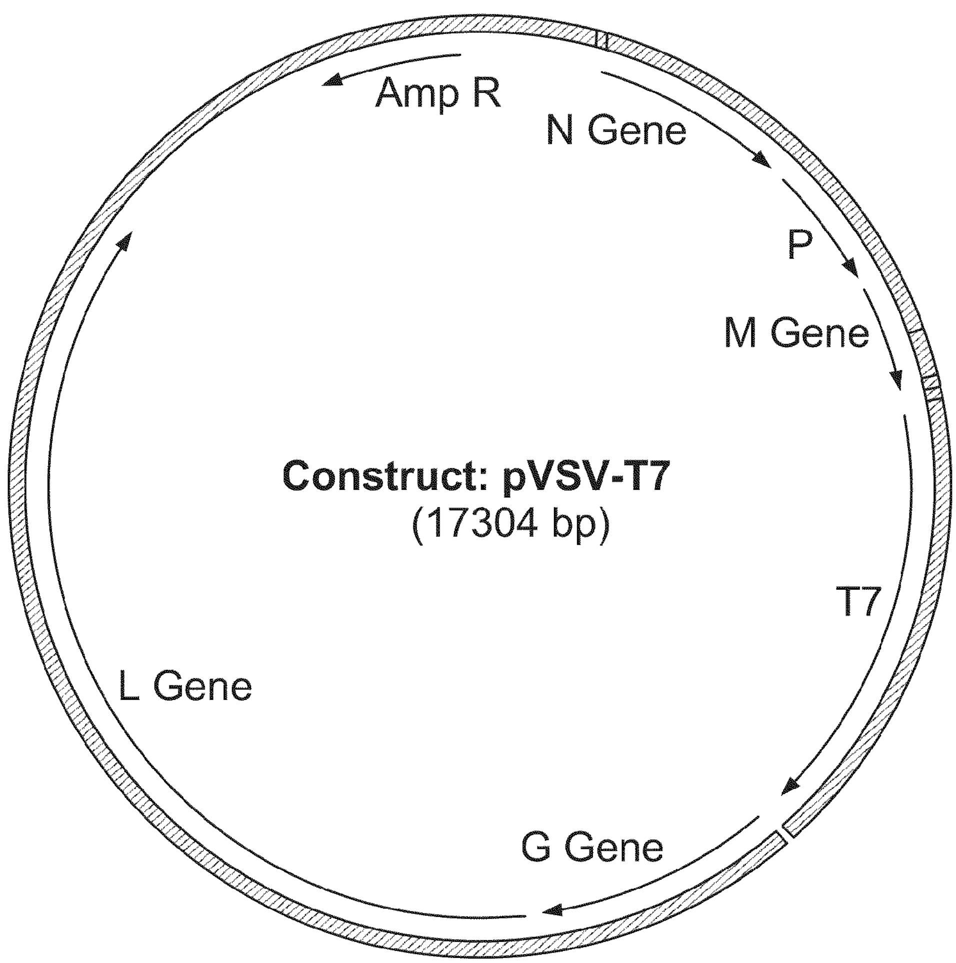
FIG. 1 depicts a pVSV-T7 plasmid map.

Unless defined otherwise, all technical and scientific terms used herein have the same meaning as is commonly understood by one of skill in the art to which the subject matter described herein belongs.

As used herein, the terms "heterologous" or "foreign nucleic acid" are used interchangeably and refer to DNA or RNA that does not occur naturally as part of the genome in which it is present or which is found in a location or locations in the genome that differs from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by the term heterologous DNA. Examples of heterologous DNA include, but are not limited to, DNA that encodes transcriptional and translational regulatory sequences and selectable or traceable marker proteins, such as a protein that confers drug resistance. Heterologous DNA may also encode DNA that mediates or encodes mediators that alter expression of endogenous DNA by affecting transcription, translation, or other regulatable biochemical processes.

As used herein, the term "vector" refers to a polynucleotide construct designed for transduction/transfection of one or more cell types. Selection and use of such vectors are well within the level of skill of the art. Generally, vectors are derived from viruses or plasmids of bacteria and yeasts. As used herein, VSV vectors may be, for example, "cloning vectors" which are designed for isolation, propagation and replication of inserted nucleotides, "expression vectors" which are designed for expression of a nucleotide sequence in a host cell, a "viral vector" which is designed to result in the production of a recombinant virus or virus-like particle, or "shuttle vectors", which comprise the attributes of more than one type of vector. The present invention encompasses VSV vectors that comprise nucleic acid encoding viral structural proteins capable of assembling into virus-like particles. As used herein, in the context of VSV, a "heterologous polynucleotide" or "heterologous gene" or "transgene" is any polynucleotide or gene that is not present in wild-type VSV. As used herein, in the context of VSV, a "heterologous" promoter is one which is not associated with or derived from VSV.

As used herein, "expression" refers to the process by which nucleic acid is transcribed into mRNA and translated into peptides, polypeptides, or proteins. "Expression" may be characterized as follows: a cell is capable of synthesizing many proteins. At any given time, many proteins which the cell is capable of synthesizing are not being synthesized. When a particular polypeptide, coded for by a given gene, is being synthesized by the cell, that gene is said to be expressed. In order to be expressed, the DNA sequence coding for that particular polypeptide must be properly located with respect to the control region of the gene. The function of the control region is to permit the expression of the gene under its control. As used herein, the term "expression vector" includes vectors capable of expressing DNA or RNA fragments that are in operative linkage with regulatory sequences, such as promoter regions, that are capable of effecting expression of such DNA or RNA fragments. Thus, an expression vector refers to a recombinant DNA or RNA construct, such as a plasmid, a phage, recombinant virus or other vector that, upon introduction into an appropriate host cell, results in expression of the cloned DNA or RNA. Appropriate expression vectors are well known to those of skill in the art and include those that are replicable in eukaryotic cells and/or prokaryotic cells and those that remain episomal or may integrate into the host cell genome.

As used herein, the terms "operative linkage" or "operative association" of heterologous DNA to regulatory and effector sequences of nucleotides, such as promoters, enhancers, transcriptional and translational stop sites, and other signal sequences, refer to the functional relationship between such DNA and such sequences of nucleotides. For example, operative linkage of heterologous DNA to a promoter refers to the physical and functional relationship between the DNA and the promoter such that the transcription of such DNA is initiated from the promoter by an RNA polymerase that specifically recognizes, binds to and correctly transcribes the DNA.

As used herein, the term "promoter region" refers to the portion of DNA of a gene that controls transcription of DNA to which it is operatively linked. A portion of the promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated. For use herein, inducible promoters are preferred. The promoters are recognized by an RNA polymerase that is expressed by the host. The promoter may be any bacteriophage promoter that can be recognized by an RNA polymerase that is expressed in the host.

As used herein, "RNA polymerase" may be endogenous to the host or may be introduced by genetic engineering into the host, either as part of the host chromosome or on an episomal element, including a plasmid containing the DNA encoding an RNA polymerase. The RNA polymerase may be a T7 polymerase derived from a prokaryotic source.

As used herein, the term "transcription terminator region" has (a) a subsegment that encodes a polyadenylation signal and polyadenylation site in the transcript, and/or (b) a subsegment that provides a transcription termination signal that terminates transcription by the polymerase that recognizes the selected promoter. The entire transcription terminator may be obtained from a protein-encoding gene, which may be the same or different from the gene, which is the source of the promoter. Transcription terminator regions can be those that are functional in *E. coli*. Transcription terminators are optional components of the expression systems herein, but are employed in preferred embodiments.

As used, the term "nucleotide sequence coding for expression of" a polypeptide refers to a sequence that, upon transcription and subsequent translation of the resultant mRNA, produces the polypeptide.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, maintenance of the correct reading frame of a protein-encoding gene to permit proper translation of the mRNA, and stop codons. In addition, sequences of nucleotides encoding a fluorescent indicator polypeptide, such as a green or blue fluorescent protein, can be included in order to select positive clones (i.e., those host cells expressing the desired polypeptide).

As used herein, "host cells" or "target cells" are cells in which a vector can be propagated and its nucleic acid expressed. The term also includes any progeny of the subject host cell. It is understood that all progeny may not be identical to the parental cell since there may be mutations that occur during replication. Such progeny are included when the term "host cell" is used. A "host cell" includes an individual cell or cell culture which can be or has been a recipient of a VSV vector(s) of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected, (no permanent genetic change is possible in this system) or infected in vivo or in vitro with a VSV vector of this invention.

As used herein, the term "packaging cell" or "packaging cell line" refers to a cell or cell lines that are able to package viral genomes or modified genomes or its equivalents. Thus, packaging cells can provide complementing functions for any genes deleted in a viral genome (e.g. nucleic acids encoding structural genes) and are able to package the viral genomes into viral vector particles. The production of such particles requires that the genome be replicated and that those proteins necessary for assembling a viral particle (infectious or non-infectious) are produced. The particles also can require certain proteins necessary for the maturation of the viral particle. Such proteins can be provided by the vector or by the packaging cell.

As used herein, the term "transfection" refers to the taking up of DNA or RNA by a host cell. Transformation refers to this process performed in a manner such that the DNA is replicable, either as an extrachromosomal element or as part of the chromosomal DNA of the host. Methods and means for effecting transfection and transformation are well known to those of skill in this art (see, e.g., Wigler et al. (1979) Proc. Natl. Acad. Sci. USA 76:1373-1376; Cohen et al. (1972) Proc. Natl. Acad. Sci. USA 69:2110).

As used herein, the term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells, and organisms comprising transgenic cells are referred to as "transgenic organisms".

As used herein, the term "substantially pure" means sufficiently homogeneous to appear free of readily detectable impurities as determined by standard methods of analysis, such as thin layer chromatography (TLC), gel electrophoresis, or high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, the term "isolated substantially" pure DNA refers to DNA fragments purified according to standard techniques employed by those skilled in the art (see, e.g., Maniatis et al. (1982) Molecular Cloning: A Laboratory Manual, Cold Spring Harbor Laboratory Press, Cold Spring Harbor, N.Y. and Sambrook et al. (1989) Molecular Cloning: A Laboratory Manual, Cold Spring Harbor Laboratory Press, Cold Spring Harbor, N.Y.).

As used herein, a "culture" means a propagation of cells in a medium conducive to their growth, and all sub-cultures thereof. The term subculture refers to a culture of cells grown from cells of another culture (source culture), or any subculture of the source culture, regardless of the number of subculturings that have been performed between the subculture of interest and the source culture. The term "to culture" refers to the process by which such culture propagates.

As used herein, the term "peptide" and/or "polypeptide" means a polymer in which the monomers are amino acid residues which are joined together through amide bonds, alternatively referred to as a polypeptide. When the amino acids are alpha-amino acids, either the L-optical isomer or the D-optical isomer can be used, the L-isomers being preferred. Additionally, unnatural amino acids such as beta-alanine, phenylglycine, and homoarginine are meant to be included. Standard single and three letter naming conventions for amino acids are used herein.

As used herein, the term "restriction enzyme digestion" of DNA refers to catalytic cleavage of the DNA with an enzyme that acts only at certain locations in the DNA. Such enzymes are called restriction endonucleases, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 1-2 units of enzyme in about 20 μl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction cleaved ends of a DNA fragment from circularizing or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in Sections 1.56-1.61 of Sambrook, et. al., Molecular Cloning: A Laboratory Manual New York: Cold Spring Harbor Laboratory Press, 1989 (which disclosure is hereby incorporated by reference).

The terms "recovery" or "isolation" of a given fragment of DNA from a restriction digest mean separation of the digest, e.g., on polyacrylamide or agarose gel by electrophoresis, identification of the fragment of interest by comparison of its mobility versus that of marker DNA fragments of known molecular weight, removal of the gel section containing the desired fragment, and separation of the gel from DNA. These procedures are generally well known. For example, see Lawn et al., 1981, Nucleic Acids Res., vol. 9, pp. 6103-6114; and Goeddel et al., 1980, Nucleic Acids Res., vol. 8, p. 4057, which disclosures are hereby incorporated by reference.

As used herein, the term "gene" refers to those DNA sequences which transmit the information for and direct the synthesis of a single protein chain.

As used herein, "gene therapy" refers to genetic therapy that involves the transfer of heterologous DNA to certain cells, target cells, of a mammal, particularly a human, with a disorder or condition for which such a therapy is sought. The DNA is introduced into the selected target cells in a manner such that the heterolgous DNA is expressed and a therapeutic product encoded thereby is produced. Alternatively, the heterolgous DNA can in some manner mediate expression of DNA that encodes the therapeutic product, it can encode a product, such as a peptide or RNA that in some manner mediates, directly or indirectly, expression of a therapeutic product. Gene therapy also can be used to deliver nucleic acid encoding a gene product to replace a defective gene or supplement a gene product produced by the mammal or a cell in which it is introduced. The introduced nucleic acid can encode a therapeutic compound, such as a growth factor or inhibitor thereof, or a tumor necrosis factor or inhibitor thereof, or a receptor thereof, that is not normally produced in the mammalian host or that is not normally produced in therapeutically effective amounts or at a therapeutically useful time. The heterolgous DNA encoding the therapeutic product can be modified prior to introduction into the cells of the afflicted host to enhance or otherwise alter the product or expression thereof.

As used herein, "therapeutic nucleic acid" refers to a nucleic acid that encodes a therapeutic product. The product can be nucleic acid, such as a regulatory sequence or gene, or can be a protein that has a therapeutic activity or effect. For example, a therapeutic nucleic acid can be a ribozyme, antisense, double-stranded RNA, a nucleic acid encoding a protein or otherwise.

As used herein, the term "infection" refers to the invasion by agents (e.g., viruses, viral vector particles, bacteria, etc.) of cells where conditions are favorable for their replication and growth.

As used herein, the term "plasmid" means a vector used to facilitate the transfer of exogenous genetic information, such as the combination of a promoter and a heterologous gene under the regulatory control of that promoter. The plasmid can itself express a heterologous gene inserted therein. "Plasmids" are designated by a lower case p preceded and/or followed by capital letters and/or numbers. The starting plasmids herein are commercially available, are publicly available on an unrestricted basis, or can be constructed form such available plasmids in accord with published procedures. In addition, other equivalent plasmids are known in the art and will be apparent to one of ordinary skill in the art.

The term "ligation" means the process of forming phosphodiester bonds between two nucleic acid fragments. To ligate the DNA fragments together, the ends of the DNA fragments must be compatible with each other. In some cases, the ends will be directly compatible after endonuclease digestion to blunt ends to make them compatible for ligation. To blunt the ends, the DNA is treated in a suitable buffer for at least 15 minutes at 15° C., with about 10 units of the Klenow fragment of DNA polymerase I or T4 DNA polymerase in the presence of the four deoxyribonucleotide triphosphates. The DNA is then purified by phenolchloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 g of DNA. If the DNA is to be ligated into a vector, the vector is first linearized by digestion with the appropriate restriction endonuclease(s). The linearized fragment is then treated with bacterial alkaline phosphatase, or calf intestinal phosphatase to prevent self-ligation during the ligation step.

As used herein, the term "preparation of DNA from cells" means isolating the plasmid DNA from a culture of the host cells. Commonly used methods for DNA preparation are the large and small scale plasmid preparations described in sections 1.25-1.33 of Sambrook et al., supra, which disclosure is hereby incorporated by reference. After preparation of the DNA, it can be purified by methods well known in the art such as that described in section 1.40 of Sambrook et al., supra, which disclosure is hereby incorporated by reference.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, genomic RNA, mRNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate ($P—NH_2$) or a mixed phosphoramidate-phosphodiester oligomer. Peyrottes et al. (1996) Nucleic Acids Res. 24: 1841-8; Chaturvedi et al. (1996) NucleicAcids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NOS:1-6) also includes the complement sequence.

The following are non-limiting examples of polynucleotides: a gene or gene fragment, exons, introns, genomic RNA, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

As used herein, the term "under transcriptional control" refers to a term well understood in the art and indicates that transcription of a polynucleotide sequence depends on its being operably (operatively) linked to an element which contributes to the initiation of, or promotes, transcription. "Operably linked" refers to a juxtaposition wherein the elements are in an arrangement allowing them to function.

"Replication" and "propagation" are used interchangeably and refer to the ability of an VSV vector of the invention to reproduce or proliferate. These terms are well understood in the art. For purposes of this invention, replication involves production of VSV proteins and is generally directed to reproduction of VSV. Replication can be measured using assays standard in the art. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

As used herein, "expression" includes transcription and/or translation of a polynucleotide sequence.

As used herein, "internal ribosome entry sequence" ("IRES") refers to nucleic acid sequences which exhibit IRES activity (IRES elements), i.e. sequences which are capable of providing cap-independent translation of a downstream gene or coding sequence by an internal ribosome entry mechanism.

As used herein, "functional RNA" refers to sense RNA, antisense RNA, ribozyme RNA, siRNA, or other RNA that may not be translated but yet has an effect on at least one cellular process.

As used herein, "altered levels" refers to the level of expression in transgenic cells or organisms that differs from that of normal or untransformed cells or organisms.

As used herein, a first sequence is an "antisense sequence" with respect to a second sequence if a polynucleotide whose sequence is the first sequence specifically binds to, or specifically hybridizes with, the second polynucleotide sequence under physiological conditions.

As used herein, "antisense inhibition" refers to the production of antisense RNA transcripts capable of suppressing the expression of protein from an endogenous gene or a transgene.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent conditions" or "high stringency conditions", as defined herein, are identified by, but not limited to, those that (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., supra, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

As used herein, "RNA interference (RNAi)" is the process of sequence-specific, post-transcriptional gene silencing initiated by double stranded RNA (dsRNA) or siRNA. RNAi is seen in a number of organisms such as *Drosophila*, nematodes, fungi and plants, and is believed to be involved in anti-viral defense, modulation of transposon activity, and regulation of gene expression. During RNAi, dsRNA or siRNA induces degradation of target mRNA with consequent sequence-specific inhibition of gene expression.

As used herein, "interfering RNA" and "small interfering RNA" (siRNA) refer to a RNA duplex of nucleotides that is targeted to a gene of interest. A "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' and/or 5' overhang portions. In some embodiments, the overhang is a 3' and/or a 5' overhang 1, 2, 3, 4 or 5 nucleotides in length.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadelylation signal.

The practice of the present invention will employ, unless otherwise indicated, conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

B. VSV-T7 RNA Polymerase Polypeptide Expression System

1. VSV

For general information related to vesicular stomatitis virus, see, "Fundamental Virology", second edition, 1991, ed. B. N. Fields, Raven Press, New York, pages 489-503; and-"Fields Virology", third edition, 1995, ed. B. N. Fields, vol. 1, pages 1121-1159.

Figure 7:
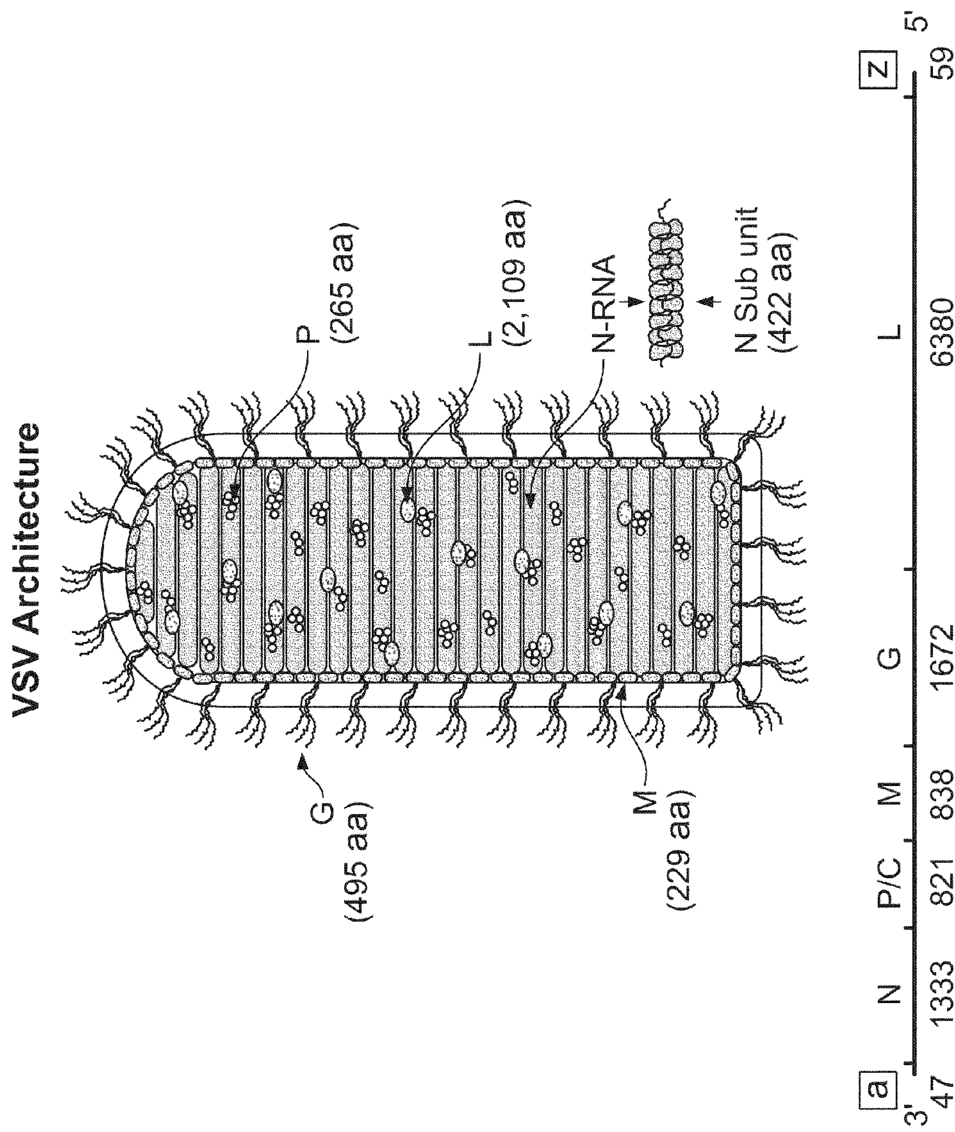
FIG. 7 represents a schematic of a vesicular stomatitis virus; structural genes are shown as is a schematic of the VSV genome.
Figure 8:
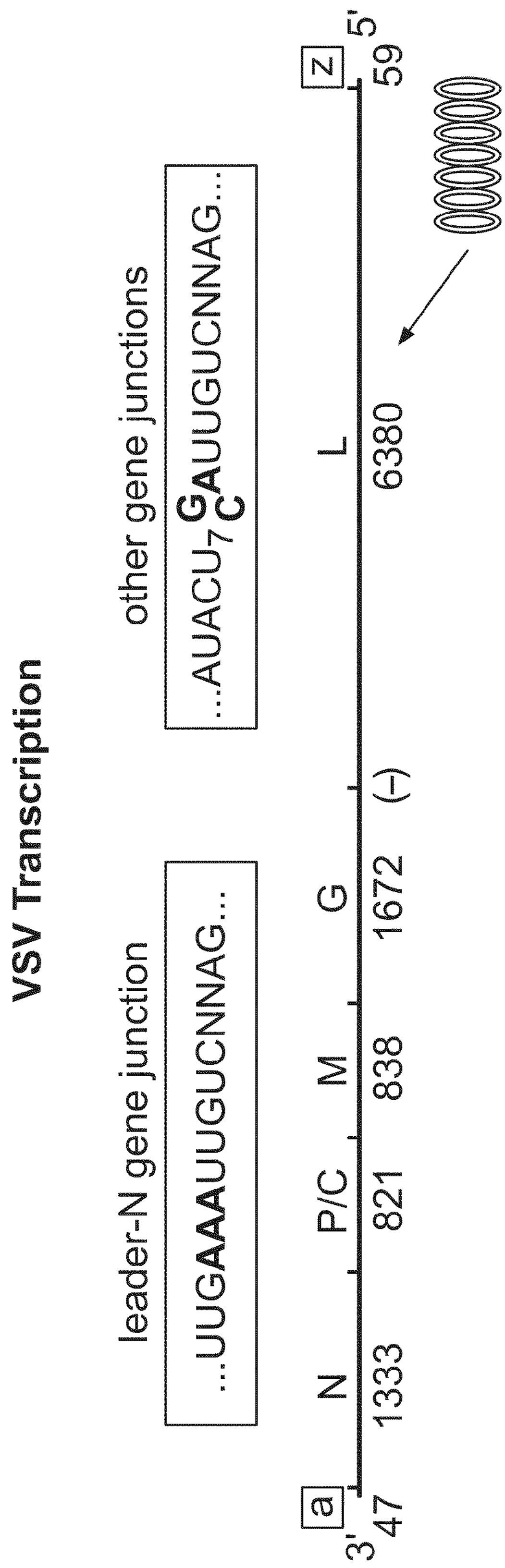
FIG. 8 represents a schematic of the VSV genome, including the sequences of the leader-N gene junction (UUGAAA-UUGUCNNAG; SEQ ID NO:7) and other gene junctions (AUACUUUUUUUG/CAUUGUCNNAG; SEQ ID NO:8). Unique features of VSV transcription are also provided.
Figure 9:
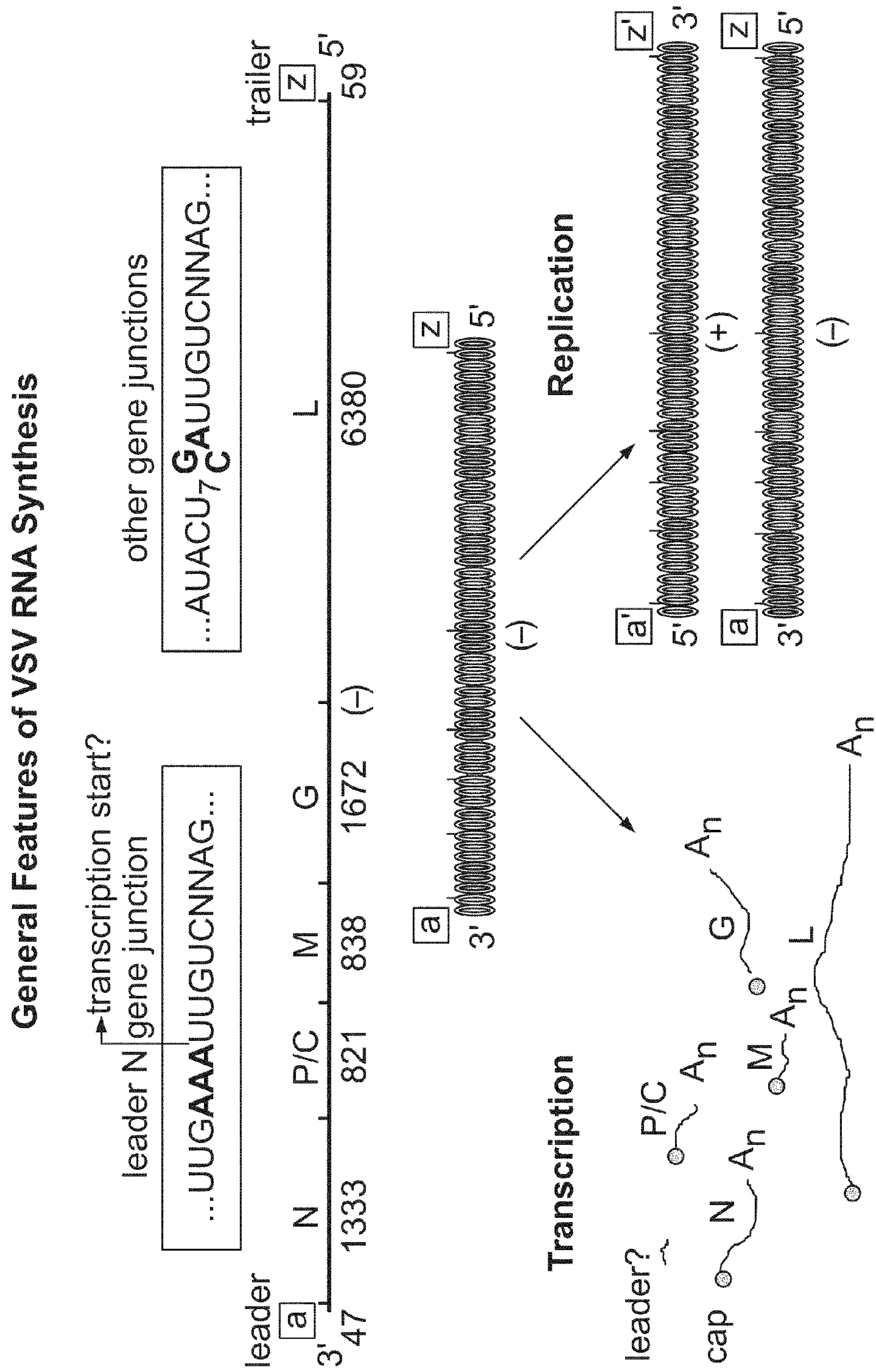
FIG. 9 represents a schematic of general features of VSV RNA synthesis, including a schematic of the VSV genome showing the sequences of the leader-N gene junction (SEQ ID NO:7) and other gene junctions (SEQ ID NO:8).
Figure 10:
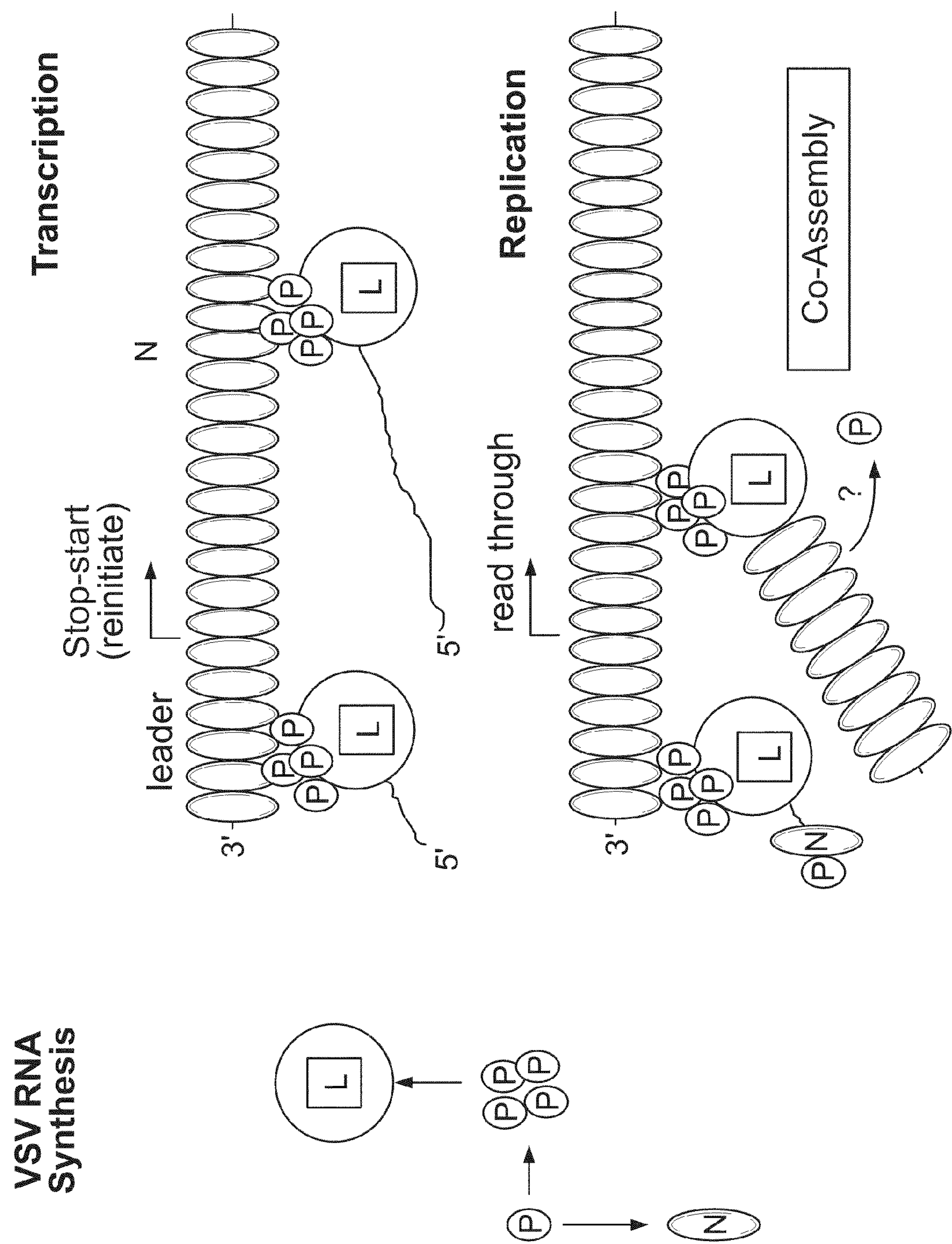
FIG. 10 represents a schematic VSV RNA synthesis emphasizing the role of the P, N and L VSV gene products during transcription.

"VSV" as used herein refers to any strain of VSV or mutant forms of VSV, for example such as those described in WO 01/19380. A VSV construct of this invention may be in any of several forms, including, but not limited to, genomic RNA, mRNA, cDNA, part or all of the VSV RNA encapsulated in the nucleocapsid core, VSV complexed with compounds such as PEG and VSV conjugated to a nonviral protein. VSV vectors provided herein may encompass replication-competent and replication-defective VSV vectors, such as, VSV vectors lacking G glycoprotein of M glycoprotein. Replication-defective VSV vectors can be grown in appropriate cell lines. FIG. 7 represents a schematic of a vesicular stomatitis virus, including a representation of the VSV genome. General features of VSV RNA synthesis are illustrated in FIGS. 9 and 10.

a. VSV Sequences and Constructs

VSV, a member of the Rhabdoviridae family, is a negative-stranded virus that replicates in the cytoplasm of infected cells, does not undergo genetic recombination or reassortment, has no known transforming potential and does not integrate any part of it genome into the host. VSV comprises an about 11 kilobase genome that encodes for five proteins referred to as the nucleocapsid (N), polymerase proteins (L) and (P), surface glycoprotein (G) and a peripheral matrix protein (M). The genome is tightly encased in nucleocapsid (N) protein and also comprises the polymerase proteins (L) and (P). Following infection of the cell, the polymerase proteins initiate the transcription of five subgenomic viral mRNAs, from the negative-sense genome, that encode the viral proteins. The polymerase proteins are also responsible for the replication of the full-length viral genomes that are packaged into progeny virions. The matrix (M) protein binds to the RNA genome/nucleocapsid core (RNP) and also to the glycosylated (G) protein, which extends from the outer surface in an array of spike like projections and is responsible for binding to cell surface receptors and initiating the infectious process.

Following attachment of VSV through the (G) protein to receptor (s) on the host surface, the virus penetrates the host and uncoats to release the RNP particles. The polymerase proteins, which are carried in with the virus, bind to the 3' end of the genome and sequentially synthesize the individual mRNAs encoding N, P, M, G, and L, followed by negative-sense progeny genomes. Newly synthesized N, P and L proteins associate in the cytoplasm and form RNP cores which bind to regions of the plasma membrane rich in both M and G proteins.

Figure 2:
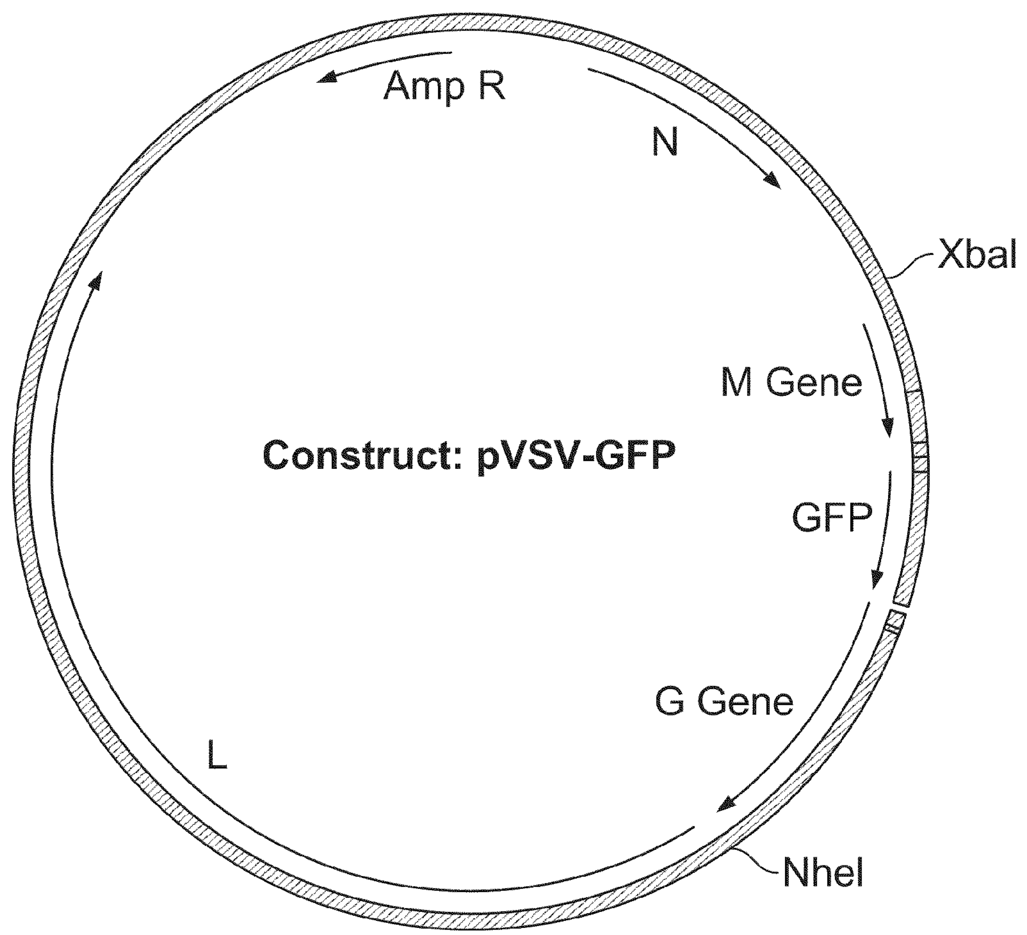
FIG. 2 depicts a pVSV-GFP plasmid map.

FIGS. 1 and 2 depict schematic illustrations of VSV-T7 RNA polymerase plasmids as provided herein and as set forth in SEQ ID NOS:1 and 2, respectively.

b. Viral Particles Form and Budding or Release of Progeny Virus Ensues.

A table of various VSV strains is shown in "Fundamental Virology", second edition, supra, at page 490. WO01/19380 and U.S. Pat. No. 6,168,943 disclose that strains of VSV include Indiana, New Jersey, Piry, Colorado, Coccal, Chandipura and San Juan. The complete nucleotide and deduced protein sequence of a VSV genome is known and is available as Genbank VSVCG, accession number J02428; NCBI Seq ID335873; and is published in Rose and Schubert, 1987, in The Viruses: The Rhabdoviruses, Plenum Press, NY. pp. 129-166. A complete sequence of a VSV strain is shown in U.S. Pat. No. 6,168,943.

VSV New Jersey strain is available from the American Type Culture Collection (ATCC) and has ATCC accession number VR-159. VSV Indiana strain is available from the ATCC and has ATCC accession number VR-1421.

Provided herein are compositions and methods encompassing any form of VSV, including, but not limited to genomic RNA, mRNA, cDNA, and part or all of VSV RNA encapsulated in the nucleocapsid core. The present invention encompasses VSV in the form of a VSV vector construct as well as VSV in the form of viral particles. Also provided herein are nucleic acid encoding specific VSV vectors disclosed herein, such as set forth in SEQ ID NOS:1 and 2. As provided herein, VSV vectors encompass replication-competent as well as replication-defective VSV vectors. Replication-competent VSV viral particles were prepared using standard methodology such as described by Whelan et al. (*Proc Natl Acad Sci USA.* 1995 Aug. 29; 92(18):8388-92).

In certain aspects, the VSV vector lacks a protein function essential for assembly and release of infectious particles, such as G-protein function or M protein function. The VSV vector may lack several protein functions essential for replication. Such vectors are useful in producing VSV-T7 replication-defective viral particles. For example, plasmids encoding the M and G genes (pTM1-M and pTM1-G) can be co-transfected with standard plasmids encoding the L, P, and N proteins into vaccinia-T7 virus-infected BHK-21 cells. The co-transfected template plasmid in this case encodes the replication-defective virus genome, which includes the T7 RNA polymerase gene but not the M and G viral genes. Following initial packaging and release of the defective viral particles, further amplification of the defective particles is accomplished by co-transfection with pTM1-M and pTM1-G plasmids to supply the missing M and G proteins. In the absence of the complementing plasmids, replication-defective viruses replicate the defective genome and express N, P and L proteins in the infected cells, but the defective genomes are neither packaged nor released. Co-transfection of cells infected with VSV-T7 replication-defective viral vectors and with plasmids encoding a transgene leads to efficient protein expression of the transgene in the cell.

Figure 11:
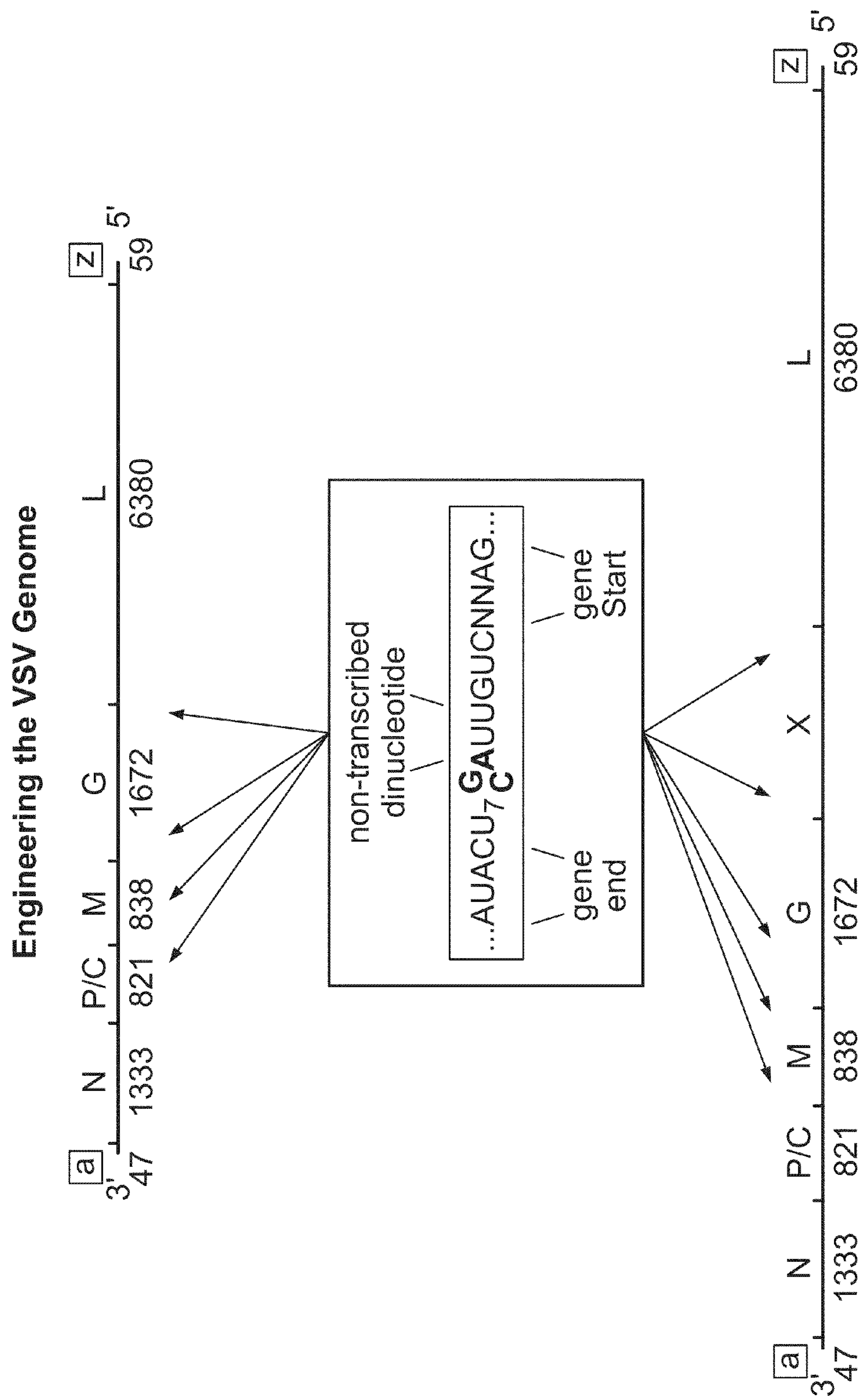
FIG. 11 represents a schematic of an engineered VSV genome showing the sequence of the gene junctions (SEQ ID NO:8); any foreign gene flanked by gene end and start signals are faithfully transcribed by the viral polymerase.
Figure 12:
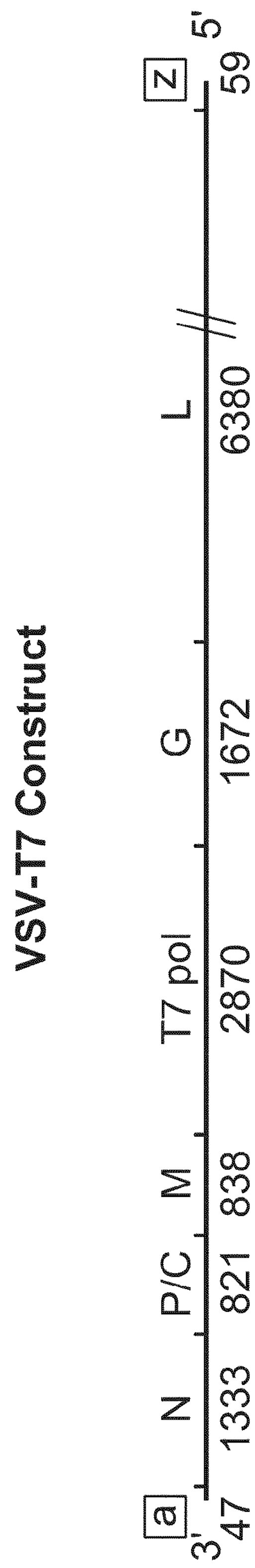
FIG. 12 represents a schematic of the VSV-T7 RNA polymerase construct as described herein.

In certain embodiments, viral particles comprising a VSV vector provided herein encode the polynucleotide sequence for T7 RNA polymerase. Also provided is isolated nucleic acid encoding the recombinant VSV vector, as well as host cells comprising a recombinant VSV vector for producing such particles. Schematic illustrations of engineered VSV-T7 viral particle genomes are shown in FIGS. 11 and 12. Any foreign gene flanked by gene end and start signals are faithfully transcribed by the viral polymerase (see FIG. 11).

2. T7 RNA Polymerase Expression System a. T7 RNA Polymerase and Promoter

As provided herein, the disclosed polypeptide expression system, involves infecting cultured cells with a VSV-T7 recombinant virus and transfecting these infected cells with a plasmid encoding a heterologous DNA sequence under control of the T7 promoter and an IRES element (see FIG. 12). The gene encoding T7 RNA polymerase is derived from a prokaryotic source. In one aspect, the VSV-T7 recombinant virus vector is engineered to express a prokaryotic T7 RNA polymerase enzyme in the cytoplasm of infected cells. The infected cells are then transfected with a recombinant plasmid vector encoding a heterologous DNA downstream of a T7 promoter sequence and an IRES element. This results in cytoplasmic accumulation of large amounts of T7 mRNA transcripts which are efficiently translated into the desired protein.

In another aspect, the T7 RNA polymerase enzyme in the cytoplasm of infected cells is capable of transcription of a heterologous DNA downstream of a T7 promoter sequence, but without an IRES element. In such circumstances, the cell is co-transfected with plasmids expressing the two subunits of the vaccinia virus-capping enzyme under control of the virus, as discussed in detail below.

As provided herein, a T7 promoter sequence facilitates binding of T7 polymerase to a polynucleotide sequence for the initiation of transcription. Also contemplated are any bacteriophage promoter sequences that can be recognized by an RNA polymerase that is expressed in the host.

b. IRES

T7 transcripts synthesized using the VSV-T7 expression system provided herein lack cap structures at their 5' ends and thus require an IRES element for efficient translation. The IRES element is capable of providing cap-independent translation of a downstream gene or coding sequence by an internal ribosome entry mechanism. In certain aspects, recombinant plasmid vectors provided herein encode a T7 promoter sequence, an IRES element and a heterologous polynucleotide sequence for efficient transcription and expression of the desired protein.

c. Vaccinia Virus-Capping Enzymes

To circumvent the requirement for an IRES element in the plasmid encoding the heterologous polynucleotide of interest provided herein are compositions and methods for co-transfecting target cells with plasmid vectors encoding the D1 and D12 subunits of vaccinia virus-capping enzyme, as set forth in SEQ ID NOS:5 and 6. Expression of the vaccinia virus-capping enzyme results in capping of the 5' end of nascent transcripts, thereby facilitating efficient translation. The capping enzyme sequences may be provided as separate plasmid vectors.

3. Recombinant Plasmids

Figure 3:
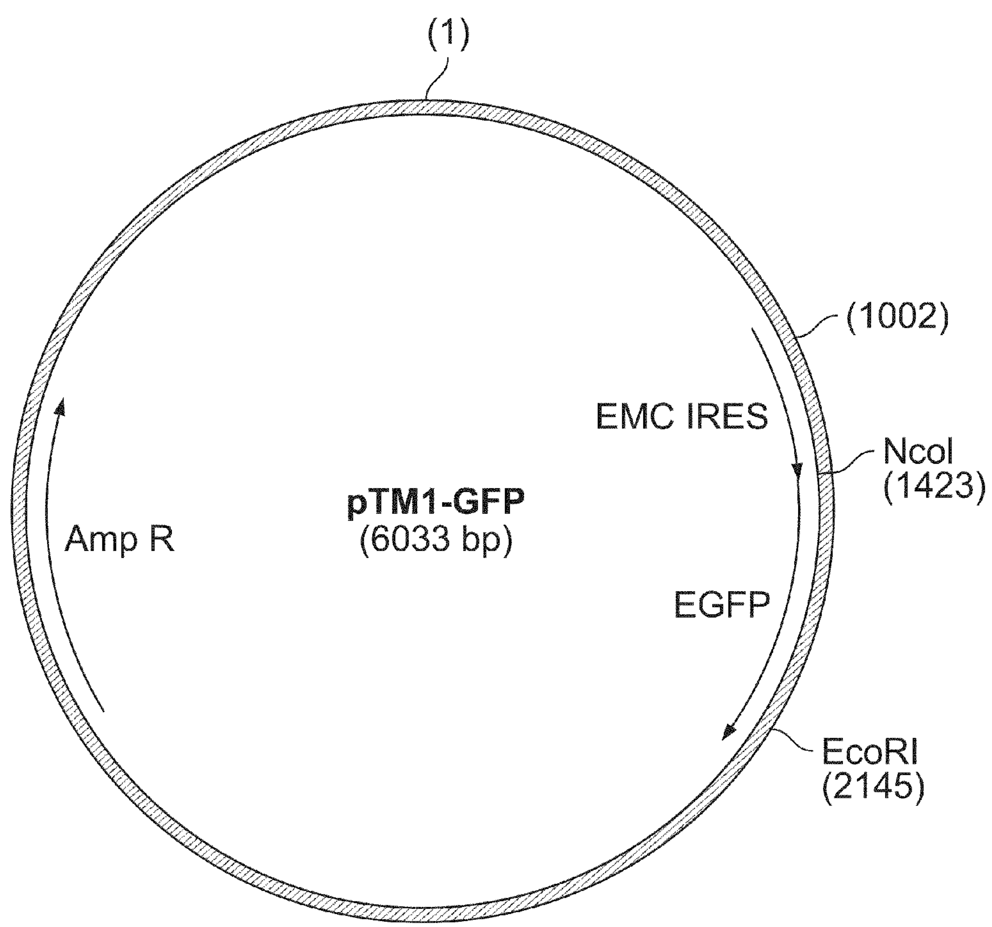
FIG. 3 depicts a pTM1-GFP plasmid map.

Recombinant plasmids provided herein were constructed using standard molecular biology cloning techniques known to those of ordinary skill in the art. Recombinant VSV viruses that express T7 RNA polymerase can drive expression of the desired heterologous polynucleotide sequence encoded on plasmids under control of a T7 promoter. Other bacteriophage promoter sequences may also be used. FIG. 3 illustrates plasmid pTM1-GFP (SEQ ID NO:3) encoding an IRES element and the green fluorescent protein (GFP) reporter gene. The GFP gene from pBI-GFP was inserted into the NcoI site of the pTM-1 vector using standard restriction enzyme cloning techniques. As will be recognized by one of skill in the art, the GFP gene can be replaced by any heterologous polynucleotide sequence using appropriate restriction enzyme recognition sites and standard molecular biology techniques.

Figure 4:
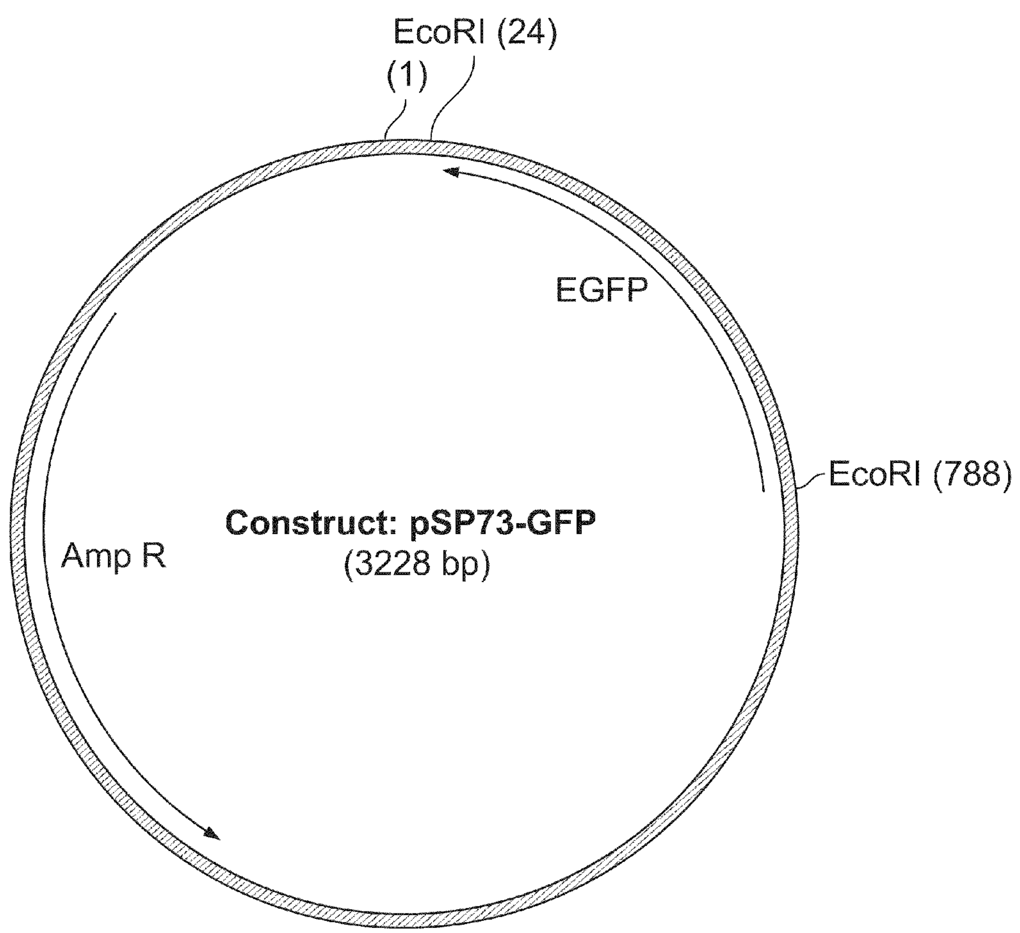
FIG. 4 depicts a pSP73-GFP plasmid map.

FIG. 4 illustrates plasmid pSP73-GFP (SEQ ID NO:4) encoding the GFP reporter gene, but without an IRES element. The GFP gene from pBI-EGFP vector was inserted into the EcoRI site of the pSP73 vector. As noted above, the GFP can be replaced by any heterologous nucleotide sequence using standard restriction enzyme cloning techniques.

4. Expression of Polypeptides

As described herein, the VSV-T7 expression system is used to infect a cell with VSV-T7 viral vector particles followed by transfection of recombinant plasmids encoding a transgene using techniques well known to those of skill in the art (see, e.g., Wigler et al. (1979) Proc. Natl. Acad. Sci. USA 76:1373-1376; Cohen et al. (1972) Proc. Natl. Acad. Sci. USA 69:2110). One embodiment as described herein, involves infecting cultured cells with a VSV-T7 recombinant virus and transfecting these infected cells with a plasmid encoding a heterologous polynucleotide sequence (e.g. transgene) under control of the T7 promoter and an IRES element. Although VSV normally shuts off host cell protein synthesis, it was found that T7 transcripts are efficiently translated under these conditions to yield protein amounts comparable to the vaccinia-T7 system. T7 transcripts synthesized in this VSV-T7 system lack cap structures at their 5' end and thus require an IRES element for translation. In another embodiment provided herein, compositions and methods are provided wherein VSV-T7 infected cells are co-transfected with plasmids encoding the two subunits of the vaccinia virus-capping enzyme (SEQ ID NOS:5 and 6) under control of an IRES element, thereby circumventing the requirement for an IRES element in the plasmid encoding the transgene of interest. Also contemplated is a defective VSV-T7 recombinant virus that lacks virus-encoded host cell shutoff functions for improving expression of the transgene.

4. Expression of Interfering RNAs

Provided herein is a viral vector expression system for delivery of a nucleic acid sequence encoding a small interfering RNA molecule (siRNA) targeted against a gene of interest.

The target gene may be a gene derived from the cell, an endogenous gene, a transgene, or a gene of a pathogen which is present in the cell after infection thereof. Depending on the particular target gene and the dose of double stranded RNA material delivered, the procedure may provide partial or complete loss of function for the target gene. A reduction or loss of gene expression in at least 99% of targeted cells has been shown. Lower doses of injected material and longer times after administration of dsRNA may result in inhibition in a smaller fraction of cells. Quantitation of gene expression in a cell may show similar amounts of inhibition at the level of accumulation of target mRNA or translation of target protein.

The RNA may comprise one or more strands of polymerized ribonucleotide. The double-stranded structure may be formed by a single self-complementary RNA strand, by two complementary RNA strands or by co-transfecting cells with plasmids encoding transgenes or fragments thereof in opposite orientation relative to the T7 promoter. RNA duplex formation may be initiated either inside or outside the cell. The RNA may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. RNA containing a nucleotide sequence identical to a portion of the target gene can be used for inhibition. RNA sequences with insertions, deletions, and single point mutations relative to the target sequence have also been found to be effective for inhibition. Thus, sequence identity may be optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

The cell with the target gene may be derived from or contained in any organism (e.g., plant, animal, protozoan, virus, bacterium, or fungus). RNA may be synthesized either in vivo or in vitro. Cloned RNA polymerase as provided by the VSV-T7 expression system may mediate transcription in vivo. For transcription from a transgene in vivo or an expression construct, a regulatory region, i.e., the T7 promoter, may be used to transcribe the RNA strand (or strands) (the regulatory sequence is the T7 promoter). A method of reducing the expression of a gene product in a cell, comprising contacting a cell with the VSV viral particle encoding T7 RNA polymerase and appropriate recombinant plasmid vector encoding the desired interfering RNA nucleotide sequence are also provided RNA interference is now established as an important biological strategy for gene silencing, but its application to mammalian cells has been limited by nonspecific inhibitory effects of long double-stranded RNA on translation. Provided herein are compositions and methods for a viral mediated delivery mechanism that results in delivery of small interfering RNA (siRNA) into a target cell. This viral mediated strategy is generally useful in reducing expression of target genes in order to model biological processes or to provide therapy for dominant human diseases.

EXAMPLES

Example 1

Vaccinia-T7 Expression System

High level expression of a reporter protein (green fluorescent protein) using an IRES-containing plasmid construct was accomplished using the VSV-T7 expression system provided herein and shown to be comparable in efficiency to the vaccinia-T7 system. Infectious VSV-T7 viral particles were recovered from BHK-321 cells (baby hamster kidneys) transfected with pVSV-T7 (SEQ ID NO:1; FIG. 1) grown in minimal essential medium (MEM) supplemented with 7% newborn calf serum using standard tissue culture techniques. Supernatants containing viral particles were titered by plaque assay and used as inoculae for expression studies. Vaccinia-T7 virus stocks were prepared using similar techniques in BSC-40 cells (monkey kidney). All expression experiments were performed using nearly confluent BHK-21 cells grown in monolayers in 5 cm plates (~$1\times10^6$ cells per plate). All virus adsorptions were performed at a multiplicity of 10 pfu/cell in a volume of 0.3 ml for 1 h at room temperature. Vaccinia-T7 inoculae also included 10 μg/ml of DEAE-dextran and 40 μg/ml Ara-C.

Following adsorption, the virus inoculae were removed before addition of 0.5 ml of the transfection reagents containing 45 μl lipofection reagent (prepared as described by Rose et al. (Biotechniques 1991, 10:520-525)) and 455 μA of MEM containing various amounts of plasmid encoding the reporter gene. After 1 hr, 1.5 ml of fresh MEM plus 7% newborn calf serum was added (containing 40 μg/ml Ara-C for vaccinia-T7 infections) and monolayers were incubated at 37° C. Expression of GFP was examined by fluorescent microscopy at various times.

Figure 13:
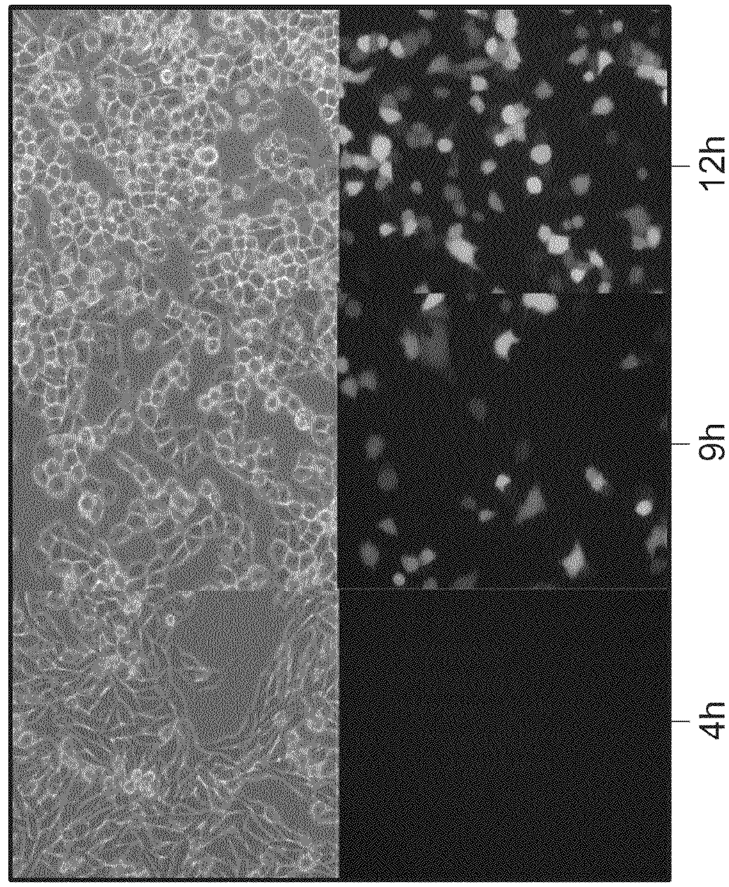
FIG. 13 shows expression of GFP in cells transfected with the vaccinia T7 system and pTM1-GFP plasmid encoding an IRES element.
Figure 14:
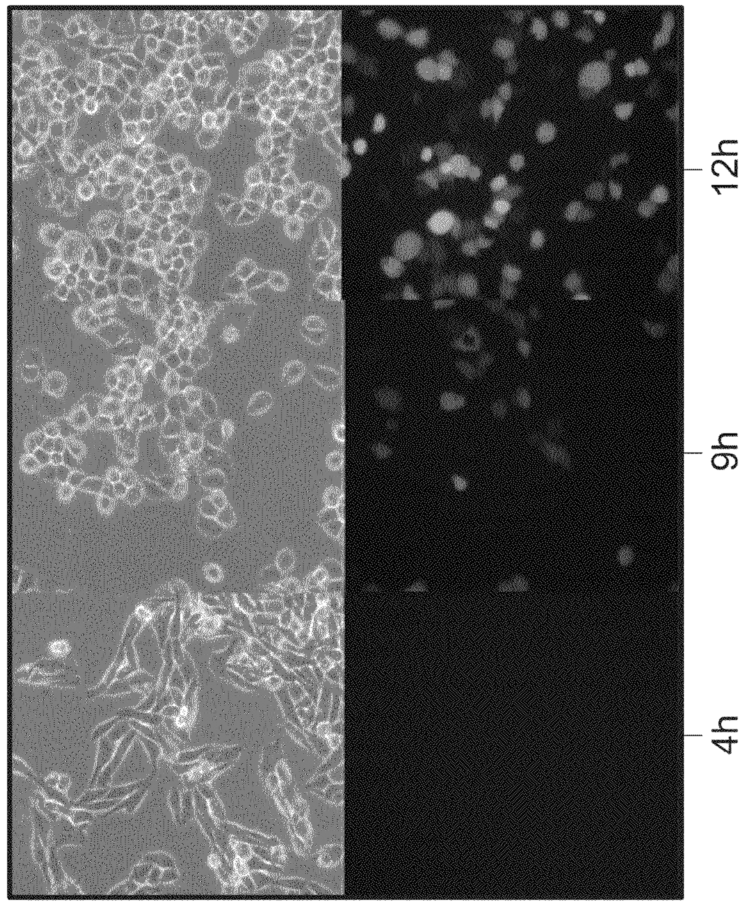
FIG. 14 shows expression of GFP in cells transfected with the vaccinia T7 system and pSP73-GFP plasmid without an IRES element.

FIG. 13 shows expression of GFP in cells infected with vaccinia-T7 viral particles, followed by transfection with 11 μg of pTM1-GFP (with IRES), at 4 h, 9 h, and 12 h, post-transfection (bottom panel). Cells infected with vaccinia-T7 viral particles and then transfected with 11 μg of pSP73-GFP (no IRES) are shown in FIG. 14 (EGF expressing cells shown in the bottom panel). The level of GFP expression is similar with or without an IRES element encoded in the expression plasmid when using a vaccinia-T7 viral expression system.

Example 2

VSV-T7 Expression System

Figure 15:
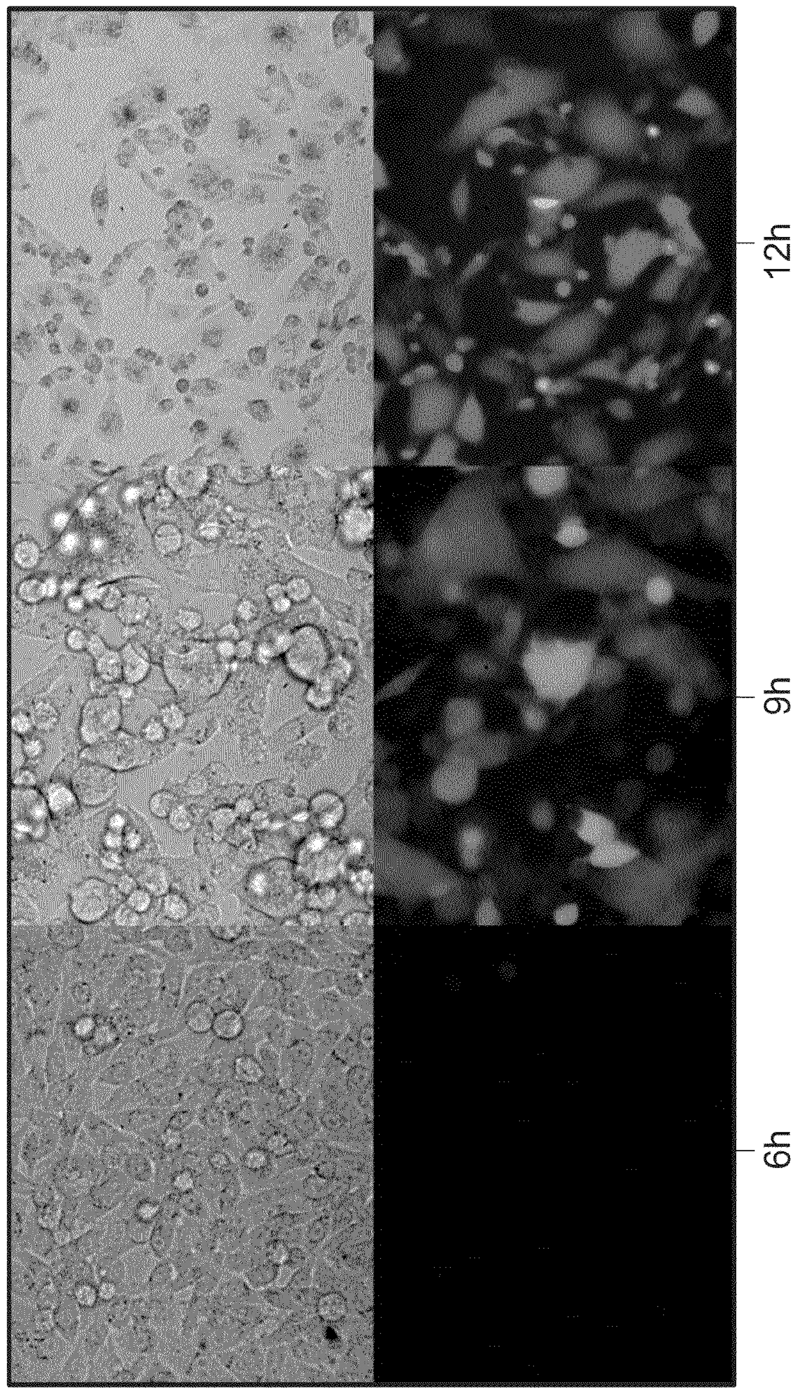
FIG. 15 shows expression of GFP in cells transfected with the VSV-T7 system and pTM1-GFP plasmid encoding an IRES element.
Figure 16:
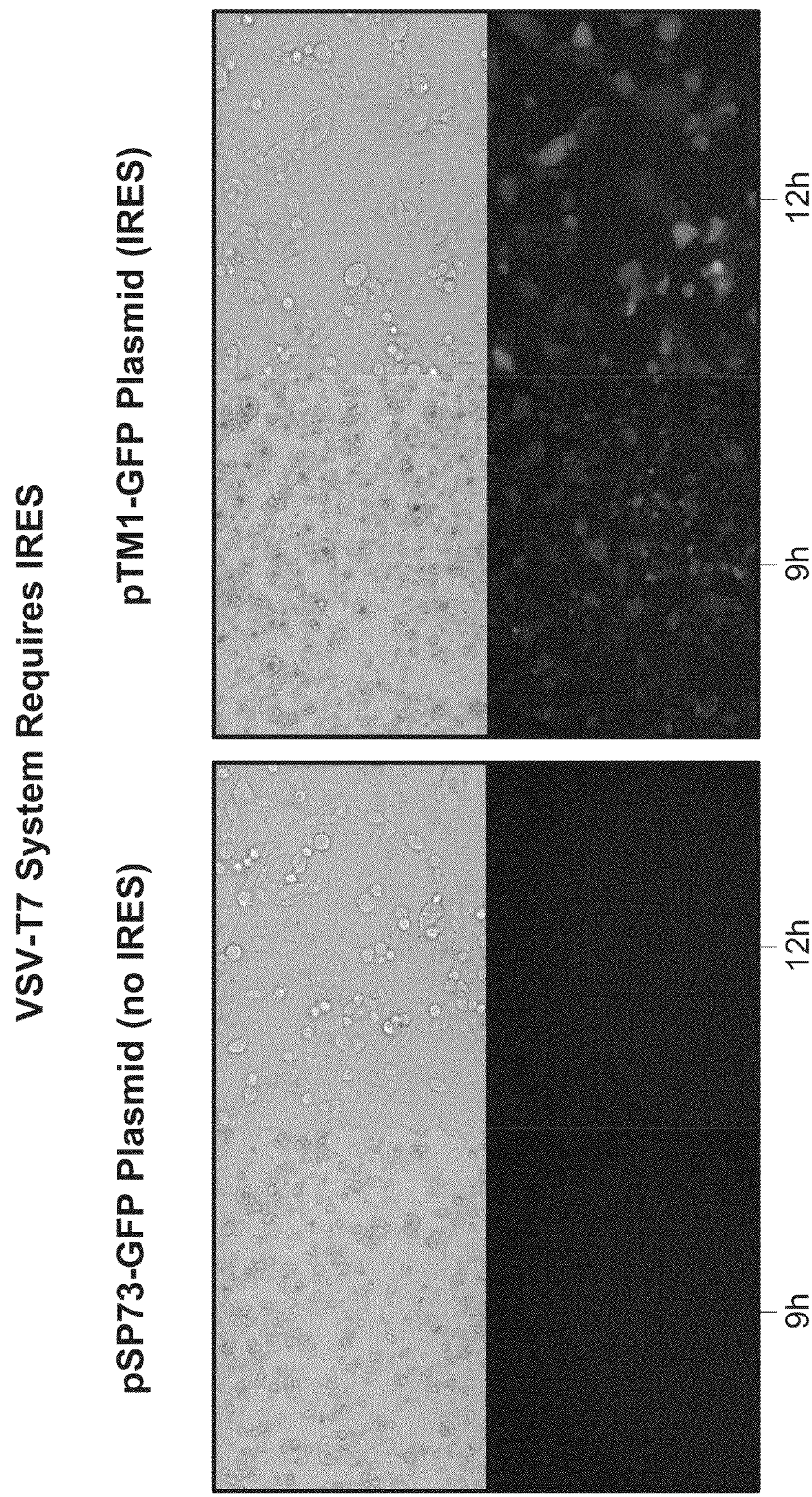
FIG. 16 shows expression of GFP in cells transfected with the VSV-T7 system and either the pSP73-GFP (no IRES) or pTM1-GFP (with IRES) plasmids.

FIG. 15 shows GFP expression in cells infected with VSV-T7 viral particles and transfected with 11 μg of pTM1-GFP (with IRES) at 6 h, 9 h and 12 h post-transfection (bottom panel). Expression of the same reporter gene without an IRES element, as shown in FIG. 16, indicates that the VSV-T7 system requires an IRES element for efficient expression of the transgene if 5' capping enzymes are not provided.

Example 3

Comparison of Vaccinia-T7 and VSV-T7 Expression Systems

Figure 17:
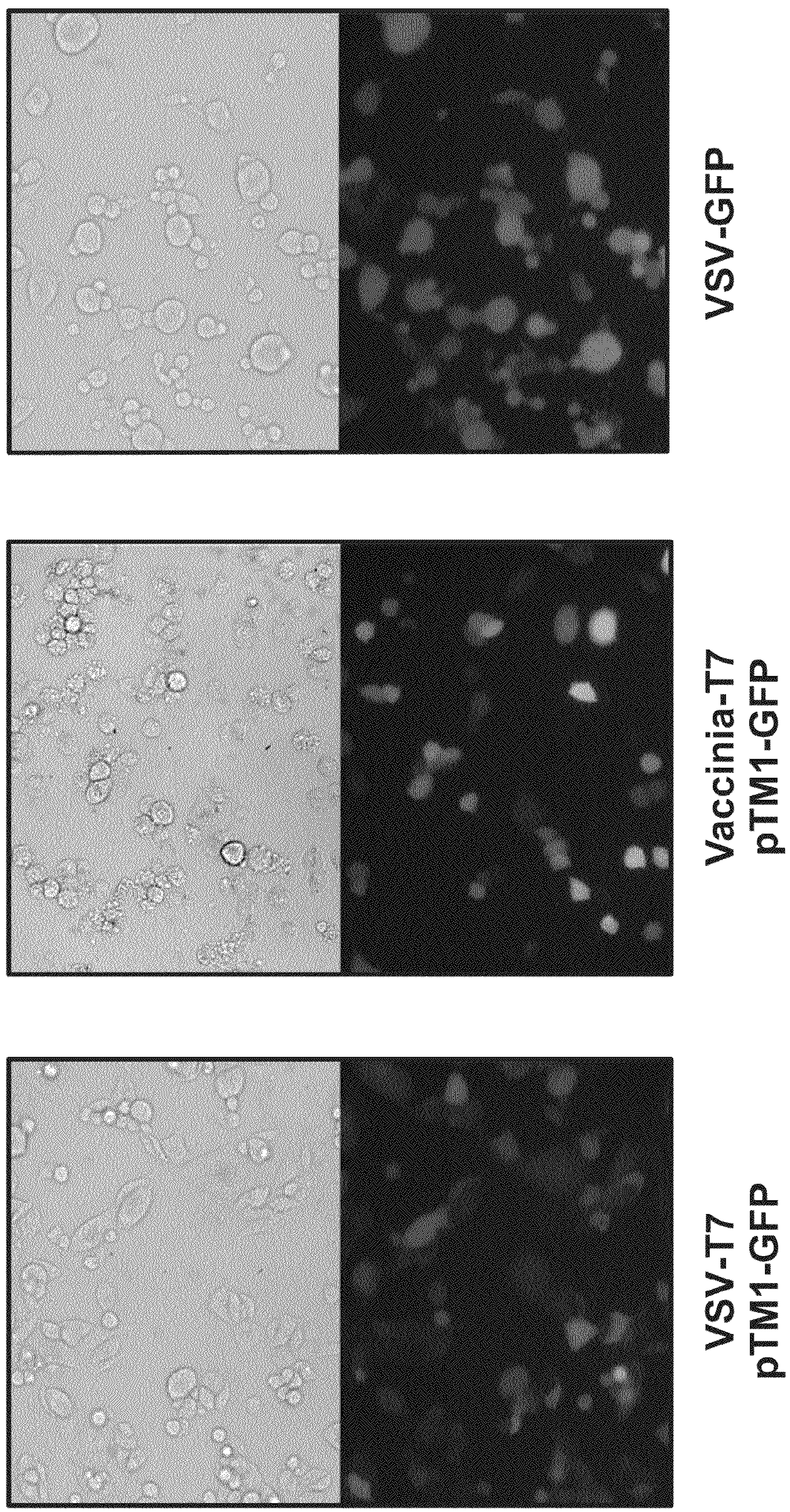
FIG. 17 shows comparison of expression of GFP in cells transformed with either the VSV-T7 or vaccinia-T7 systems.

A comparison of the VSV-T7 expression system with the vaccinia-T7 system indicates similar levels of reporter gene expression when cells are transfected with plasmids encoding an IRES (FIG. 17, bottom panel). As a comparison, cells infected with VSV viral particles encoding GFP instead of T7 RNA polymerase also express GFP at comparable levels (far right panels).

Example 4

VSV-T7 Expression System with Vaccinia Virus-Capping Enzymes

Figure 5:
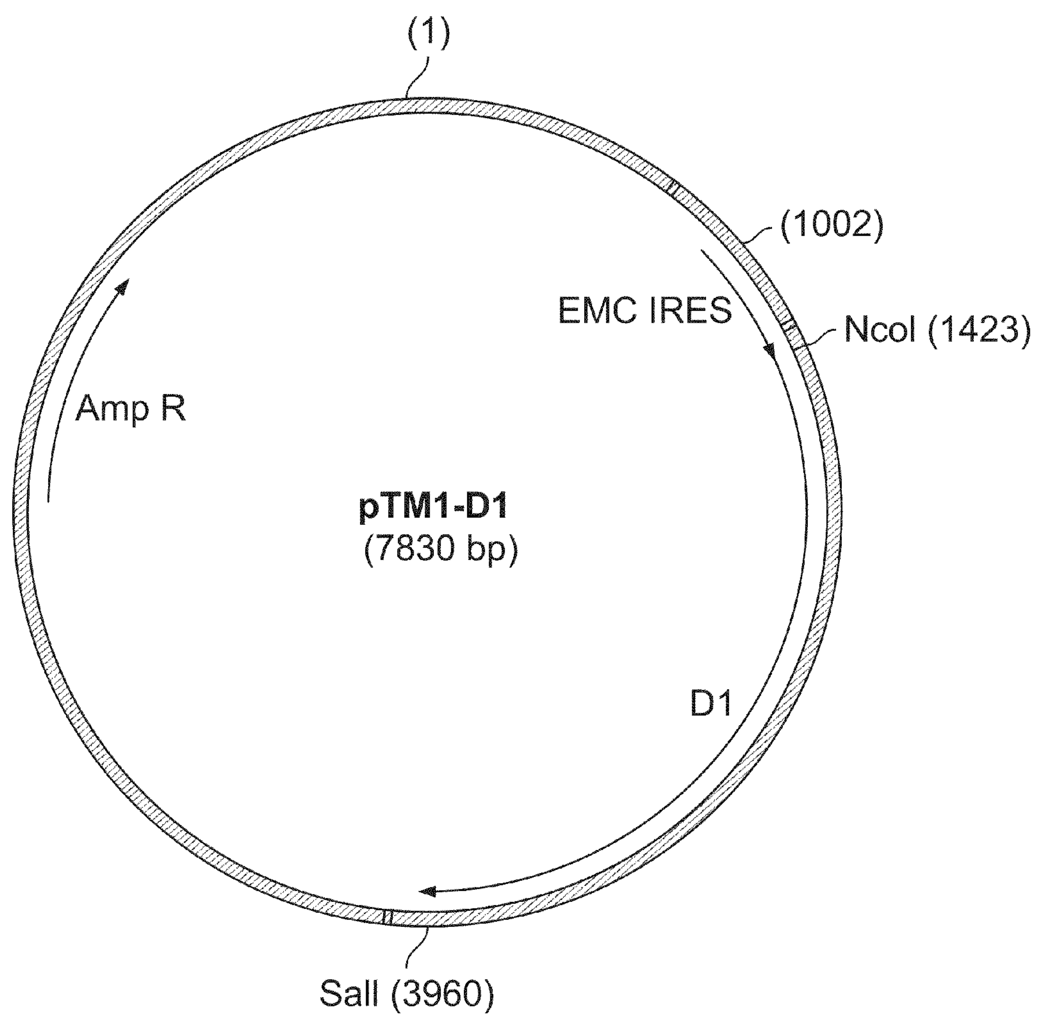
FIG. 5 depicts a pTM1-D1 plasmid map.
Figure 6:
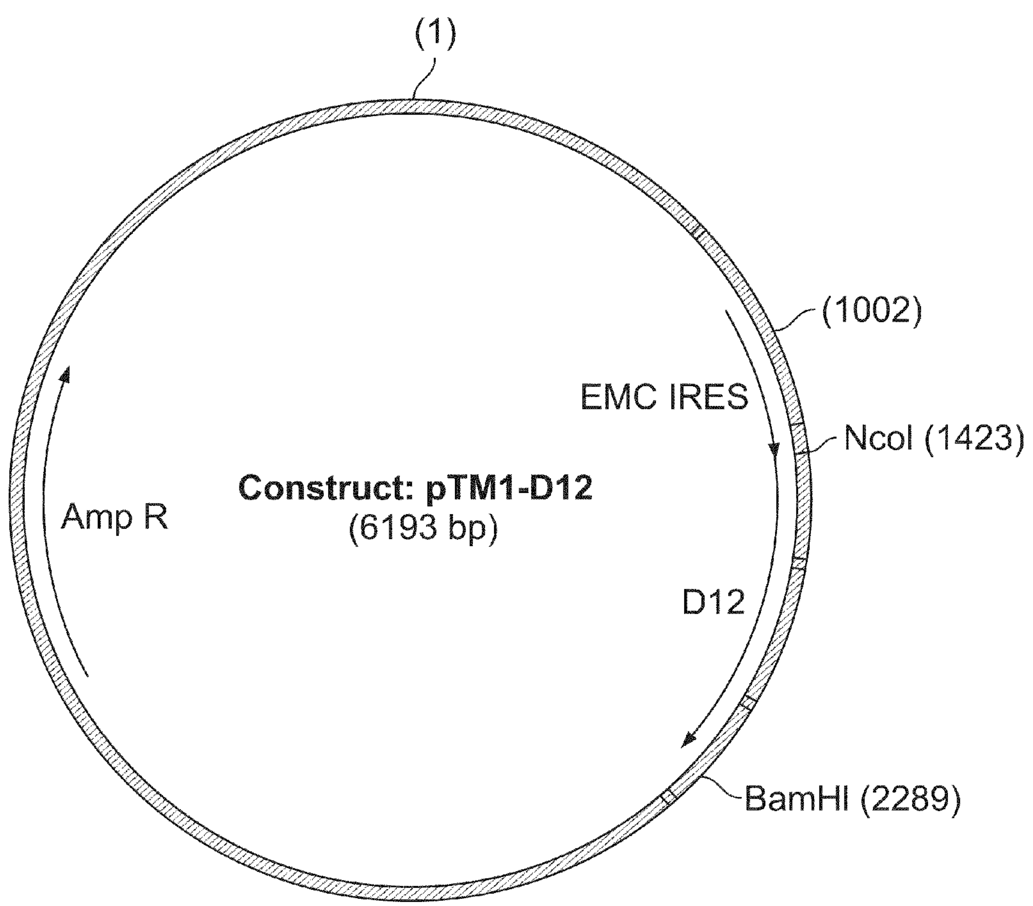
FIG. 6 depicts a pTM1-D12 plasmid map.
Figure 18:
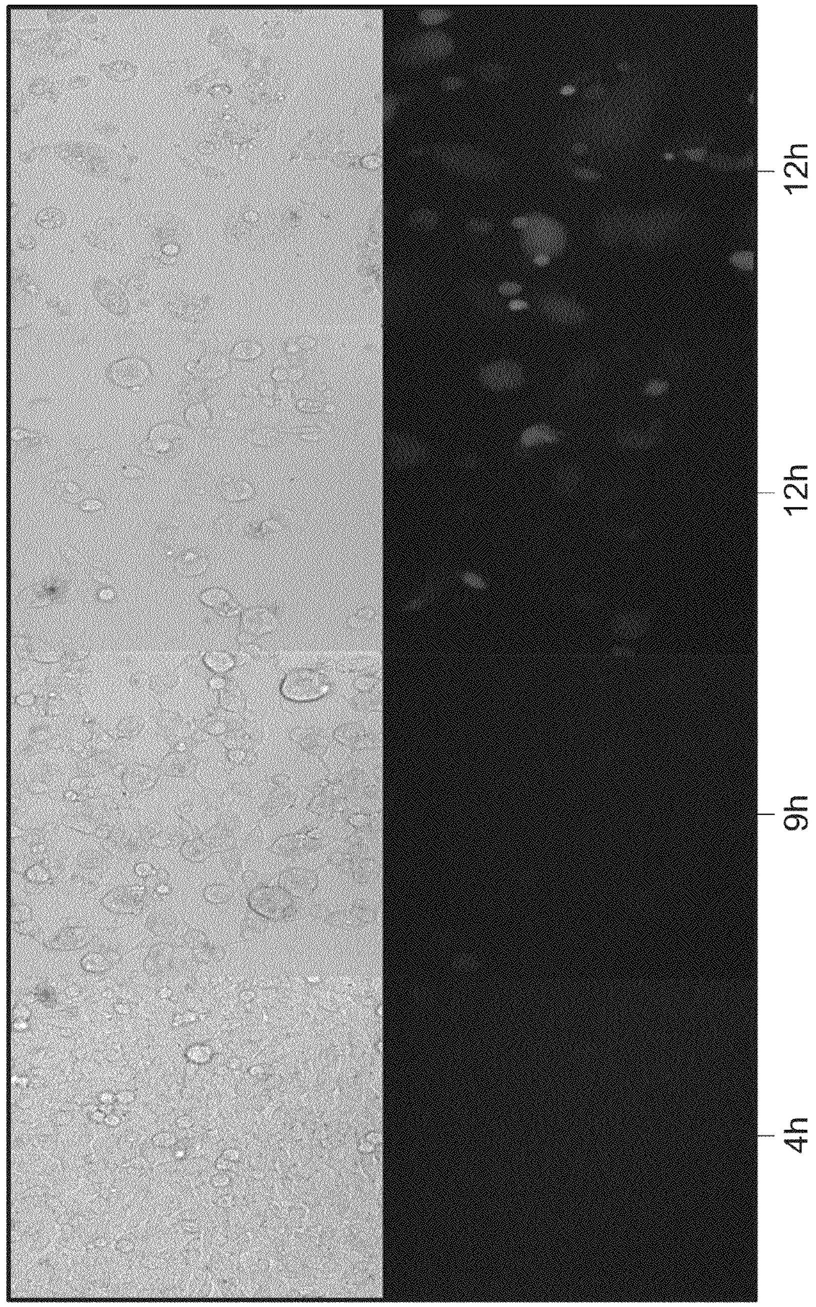
FIG. 18 shows expression of GFP in cells with the VSV-T7 system and co-transfected with plasmids pTM1-D1 and pTM1-D12 that encode the vaccinia capping enzyme.

To circumvent the requirement of an IRES element in the plasmid driving expression of the transgene, cells were co-transfected with plasmids encoding the D1 and D12 subunits of the vaccinia virus-capping enzyme under control of an IRES element (SEQ ID NOS:5 and 6; FIGS. 5 and 6). Capping functions at the 5' end of the transcript are therefore provided in trans, thus bypassing the need for an IRES element. GFP expression of cells infected with VSV-T7 viral particles followed by co-transfection with pSP73-GFP (no IRES), pTM1D1 and pTM1-D12 plasmids is shown in FIG. 18. These results indicate that the VSV-T7 expression system can be used successfully without the requirement of an IRES element if the transgene 5' capping functions are provided in trans.

A number of embodiments of the invention have been described. Nevertheless, it will be understood that various modifications may be made without departing from the spirit and scope of the invention. Accordingly, other embodiments are within the scope of the following claims.

What is claimed:

1. A recombinant vesicular stomatitis virus vector expression system comprising (a) a VSV comprising a polynucleotide encoding a T7 RNA polymerase or other bacteriophage RNA polymerase and the D1 subunit of vaccinia capping enzyme, wherein when the vector is used to infect a cell, the RNA polymerase and the D1 subunit of vaccinia capping enzyme are expressed in the cell;

(b) a recombinant plasmid vector comprising a polynucleotide comprising the following elements operably linked 5' to 3':

(i) a bacteriophage promoter corresponding to the bacteriophage RNA polymerase, and (ii) a heterologous gene, wherein when the recombinant plasmid vector is used to transfect said cell, a polypeptide is expressed from transcripts encoded by said heterologous gene in the cell.

2. The system of claim 1, wherein the VSV comprises a polynucleotide encoding a T7 RNA polymerase and wherein the bacteriophage promoter is a T7 promoter.

3. The system of claim 1, wherein the recombinant plasmid vector comprises a T7 promoter corresponding to residues 794 to 813 of SEQ ID NO:3, and a heterologous gene, with IRES polynucleotide encoding sequences deleted.

4. The system of claim 1, wherein the VSV is encoded by a vector that comprises (a) the polynucleotide sequence set forth in SEQ ID NO:1, and (b) a polynucleotide encoding the sequence for the D1 catalytic subunit of vaccinia virus-capping enzyme as set forth in SEQ ID NO:5.

5. The system of claim 4, with the proviso that the M and/or G genes of the VSV are deleted or mutated such that the VSV is replication-deficient.

6. The system of claim 1, wherein the VSV further comprises a polynucleotide encoding the D12 subunit of vaccinia capping enzyme, wherein when the vector is used to infect a cell, the D12 subunit of vaccinia capping enzyme is expressed in the cell.

7. The system of claim 6, wherein the VSV comprises a polynucleotide encoding the sequences for D1 and D12 catalytic subunits of vaccinia virus-capping enzyme as set forth in SEQ ID NOS:5 and 6.

8. The system of claim 6, with the proviso that the M and/or G genes of the VSV are deleted or mutated such that the VSV is replication-deficient.

9. The system of claim 1, wherein said cells were transfected with said recombinant plasmid vectors by liposome mediated transfer, lipofection, polycation-mediated transfer, or direct DNA transfer or uptake.

* * * * *